(12) United States Patent
Jeannotte et al.

(10) Patent No.: US 10,481,139 B2
(45) Date of Patent: Nov. 19, 2019

(54) DMD BASED UV ABSORPTION DETECTOR FOR LIQUID CHROMATOGRAPHY

(71) Applicant: Waters Technologies Corporation, Milford, MA (US)

(72) Inventors: Anthony C. Jeannotte, Foxborough, MA (US); Daniel Gillund, Wildrose, ND (US); Aditya Shankar Prasad, Ranchi (IN); Saksham Saxena, Gorakhpur (IN)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 15/772,109

(22) PCT Filed: Nov. 3, 2016

(86) PCT No.: PCT/US2016/060323
§ 371 (c)(1),
(2) Date: Apr. 30, 2018

(87) PCT Pub. No.: WO2017/079433
PCT Pub. Date: May 11, 2017

(65) Prior Publication Data
US 2018/0313796 A1    Nov. 1, 2018

Related U.S. Application Data

(60) Provisional application No. 62/250,092, filed on Nov. 3, 2015.

(51) Int. Cl.
*G01N 30/95* (2006.01)
*G01J 1/42* (2006.01)
(Continued)

(52) U.S. Cl.
CPC .............. *G01N 30/95* (2013.01); *G01J 1/429* (2013.01); *G01J 3/00* (2013.01); *G01J 3/021* (2013.01);
(Continued)

(58) Field of Classification Search
CPC .............. G01J 1/429; G01J 3/28; G01N 30/95
See application file for complete search history.

(56) References Cited

U.S. PATENT DOCUMENTS

| | | | |
|---|---|---|---|
| 4,575,243 A | 3/1986 | Witte | |
| 5,148,239 A * | 9/1992 | Magnussen, Jr. | ......... G01J 3/42 356/319 |

(Continued)

OTHER PUBLICATIONS

International Search Report & Written Opinion in PCT/US2016/060323, dated Mar. 16, 2017; 6 pages.

(Continued)

*Primary Examiner* — Marcus H Taningco
(74) *Attorney, Agent, or Firm* — Schmeiser, Olsen & Watts LLP

(57) ABSTRACT

A detector for use in liquid chromatography is provided. The detector includes a light delivery system comprising a light source that emits one or more spectral lines of light of a light spectrum. The detector has an entrance slit configured to receive the one or more spectral lines of light and a wavelength selection module comprising a digital micro-mirror device. The digital micro-mirror device is configured to redirect the one or more spectral lines of light to a flow cell. The flow cell is optically connected to the wavelength selection module.

5 Claims, 58 Drawing Sheets

(51) Int. Cl.
*G01J 3/28* (2006.01)
*G01N 30/74* (2006.01)
*G01J 3/00* (2006.01)
*G01N 21/31* (2006.01)
*G01J 3/02* (2006.01)
*G01J 3/04* (2006.01)
*G01J 3/10* (2006.01)
*G01J 3/18* (2006.01)
*G01J 3/42* (2006.01)
*G01N 21/05* (2006.01)
*G02B 26/08* (2006.01)
*G01J 3/12* (2006.01)

(52) U.S. Cl.
CPC ........... *G01J 3/0208* (2013.01); *G01J 3/0218* (2013.01); *G01J 3/0262* (2013.01); *G01J 3/0286* (2013.01); *G01J 3/0291* (2013.01); *G01J 3/04* (2013.01); *G01J 3/10* (2013.01); *G01J 3/18* (2013.01); *G01J 3/28* (2013.01); *G01J 3/2803* (2013.01); *G01J 3/42* (2013.01); *G01N 21/31* (2013.01); *G01N 30/74* (2013.01); *G01J 2003/1213* (2013.01); *G01J 2003/2866* (2013.01); *G01N 21/05* (2013.01); *G01N 2021/3181* (2013.01); *G02B 26/0841* (2013.01)

(56) References Cited

U.S. PATENT DOCUMENTS

| | | | |
|---|---|---|---|
| 5,883,721 A | 3/1999 | Gilby et al. | |
| 6,783,705 B1 | 8/2004 | Leveille | |
| 7,678,566 B2 | 3/2010 | Miyoshi et al. | |
| 2016/0258913 A1* | 9/2016 | Uchiho | G01N 30/74 |
| 2017/0010157 A1* | 1/2017 | Minato | G01J 3/18 |
| 2017/0183388 A1* | 6/2017 | Stowell | C07K 14/4711 |
| 2017/0212049 A9* | 7/2017 | Lieber | G01N 21/645 |

OTHER PUBLICATIONS

Gillund, Daniel P. "Light Source Selection and Optical Design of a UV Absorption Based Detector for Liquid Chromatography," Thesis, Sep. 2015, Massachusetts Institute of Technology, Cambridge, MA.

Extended European Search Report in European Patent Application No. 16862965.7, dated May 21, 2019; 8 pages.

Prasad, Aditya Shankar, "Mechanical Design of Optics Bench for UV-LED Based Liquid Chromatography Detector," Thesis, Sep. 1, 2015, DSpace@MIT, https://dspace.mit.edu/handle/1721.1/101818, retrieved on May 13, 2019.

* cited by examiner

| Designation | Description |
|---|---|
| LEDs | Bank of modular LED light sources |
| Fiber | 0.22 NA fused silica fibers, 100 μm Ø |
| Entrance Slit | 0.040 x 2 mm aperture |
| Grating | 285 g/mm R curvature= 139.19 ëblaze= 250 nm |
| DMD | Lactive¡Y7 mm Pitch 5.4 μm 12° orthogonal tilt quarts window |
| Mirror | Spherical mirror Lf = 100 mm |
| BS | Beamsplitter plate 0.50 mm |
| L1 | Refractive - reflective lens, FC entrance NA in =.48, NA out = .28 CT = 5.512 mm, 6.60 mm Ø, 3.81 m m Ø CA |
| LGFC | Light guided flow cell Lfluid = 10 mm, 0.275 NA |
| PD1 | Sample photodiode 5.8 mm square active area (PD1 and PD2 are purchased as a matched pair) |
| L2 | Plano -convex lens, reference photodiode ROC = 7.8 mm, CT = 5.25 mm, 12.7 mm Ø |
| PD2 | Reference p photodiode 5.8 mm square active area (PD1 and PD2 are purchased as a matched pair) |
| Light Dump | Aluminum member coated with highly UV absorbing coating |
| ASG | Grating aperture stop 55 mm Ø |
| ASM | Mirror aperture stop 68 mm Ø |
| ASR | Reference photodiode aperture stop 2 mm Ø |

FIG. 24C

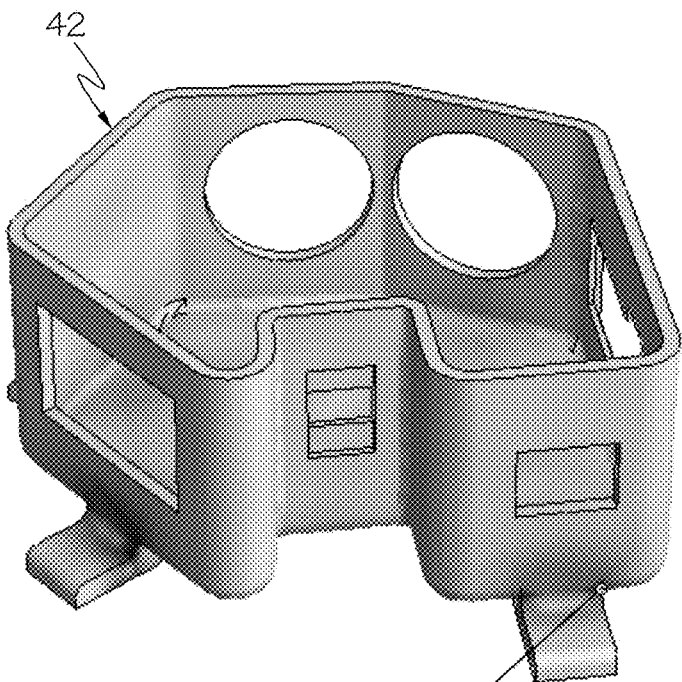
(c) 6mm wall thickness
FIG. 37C
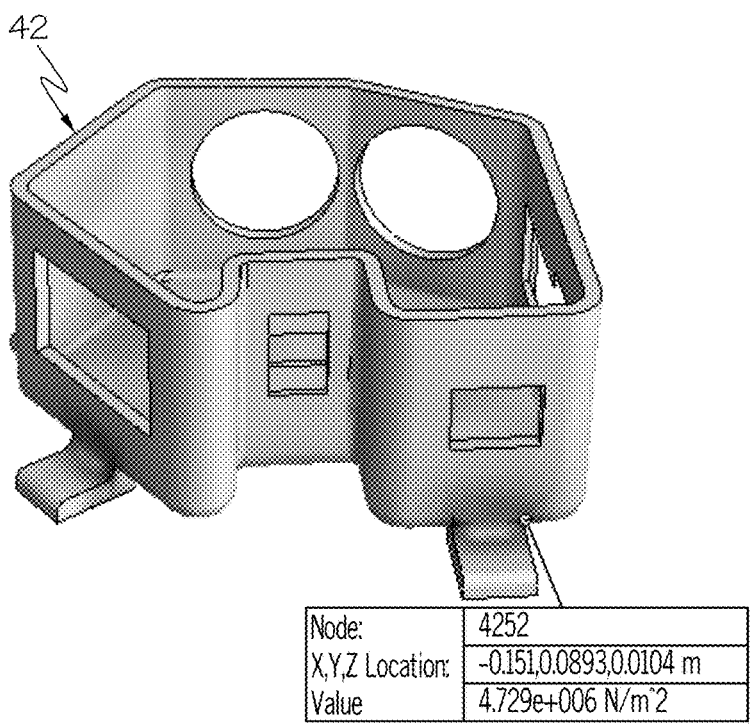
FIG. 37D (d) 7mm wall thickness (e) 8mm wall thickness (a) Mode 1

(b) Mode 2

(c) Mode 3

(d) Mode 4

ALL DIMENSIONS IN MM

82 Dry gas purge filler valve

| | Microchip | Product Chassis | Temperature Sensor | Microcontroller | Fans | Power Chord | Power Supply Unit | Analogue to Digital Converter | Cluster 2 ||||||| | Cluster 1 || |
| | | | | | | | | | Mirror | Sample Photodiode | Optical Bench | Defraction Grating | Beam Splitter | Flow Cell | Digital Micromirror Device | Reference Photodiode | Slit | Optical Fibers | Mecury Lamp | UV LEDs |
|---|---|---|---|---|---|---|---|---|---|---|---|---|---|---|---|---|---|---|---|---|
| Microchip | ■ | | | | | | | | | | | | | | | | | | | |
| Product Chassis | | ■ | | | | | | | | | | | | | | | | | | |
| Temperature Sensor | | | ■ | | | | | | | | | | | | | | | | | |
| Microcontroller | | | | ■ | | | | | | | | | | | | | | | | |
| Fans | | | | | ■ | | | | | | | | | | | | | | | |
| Power Chord | | | | | | ■ | | | | | | | | | | | | | | |
| Power Supply Unit | | | | | | | ■ | | | | | | | | | | | | | |
| Analogue to Digital Converter | | | | | | | | ■ | | | | | | | | | | | | |
| Mirror | | | | | | | | | ■ | | | | | | □ | | | | | |
| Sample Photodiode | | | | | | | | | | ■ | | | | | | | | | | |
| Optical Bench | | | | | | | | | | | ■ | | | | | | | | | |
| Defraction Grating | | | | | | | | | | | | ■ | | | | □ | | | | |
| Beam Splitter | | | | | | | | | | | | | ■ | | | □ | | □ | | |
| Flow Cell | | | | | | | | | | □ | | | | ■ | | | | | | |
| Digital Micromirror Device | | | | | | | | | | □ | | | | | ■ | | | | | |
| Reference Photodiode | | | | | | | | | | | | | | | | ■ | | | | |
| Slit | | | | | | | | | | | | | □ | | | □ | ■ | | | |
| Optical Fibers | | | | | | | | | | | | | | | | | | ■ | | |
| Mecury Lamp | | | | | | | | | | | | | | | | | | □ | ■ | |
| UV LEDs | | | | | | | | | | | | | | | | | | | □ | ■ |

DMD BASED UV ABSORPTION DETECTOR FOR LIQUID CHROMATOGRAPHY

CROSS REFERENCE TO RELATED APPLICATIONS

This application claims priority to U.S. Provisional Patent Application No. 62/250,092 filed Nov. 3, 2015, incorporated herein by reference.

BACKGROUND OF THE INVENTION

In a liquid chromatography ultraviolet detector, resolution can directly impact the capabilities of the instrument to uniquely identify substances. Resolution is the measure, in nanometers, of how far apart in wavelength two light signals are so that the detector can accurately be distinguished one from the other. Many variables can impact resolution, however. For example, two factors that set the maximum theoretical resolution are slit width and linear dispersion of the diffraction grating. Thevenon, J. M. L. and A., *A Tutorial on Spectroscopy*, 2003.

Other factors that can impact the ultraviolet detector include optical bandwidth, wavelength range and dynamic capability. The optical bandwidth of a detector is the breadth of the minimum spectra that a machine is capable of detecting. It can be equal to, or more often, greater than the resolution of the detector. For example, if an instrument has a resolution of 1 nm and an optical bandwidth of 5 nm, the detector can detect absorption between 250 nm and 255 nm or between 251 nm and 256 nm. Wavelength range is the portion of the electromagnetic spectrum in which a detector can operate and is set either by the spectral distribution of the light source or the design of the optical system. Methods for absorption spectroscopy are often designed around a specific wavelength or set of wavelengths. Therefore, a range of wavelengths over which a detector can operate often determines its useful application.

Likewise, the noise arising from the quantized nature of light, called the shot noise, often dominates the signal to noise ratio ("SNR") in UV detectors. Yariv, A., *Introduction to Optical Electronics Holt, Rinehart & Winston Series in Electrical Engineering, Electronics, and Systems,* 2nd ed. Holt, Rinehart and Winston, 1976. Often liquid chromatography is used as a method to determine not what a sample is composed of, but rather how much of a given substance is present in the sample. Yet, nearly every component of the detector and its environment has the potential to add some amount of noise to the signal. The addition of a reference can reduce or eliminate many forms of noise.

Furthermore, dynamic capabilities of a detector, or the set of features which can be used while samples are running, such as reference-based noise canceling, baseline adjustments, on-the-fly self-calibration, timesharing among multiple wavelengths, and actively modulating the source or entrance slit, often are lacking in the device. Dynamic features add flexibility and robustness to a detector, and provide a device for backwards and forwards compatibility.

A need exists for the liquid chromatography detector that is efficient, compact having low heat generation and dynamic in nature, having both backwards and forwards compatibility.

SUMMARY OF THE INVENTION

A detector for use in liquid chromatography is provided. The detector includes a light delivery system comprising a light source that emits one or more spectral lines of light of a light spectrum. The detector has a wavelength selection module comprising a digital micro-mirror device. The entrance slit of the detector receives the one or more spectral lines of light and the digital micro-mirror device redirects the one or more spectral lines of light to a flow cell. The flow cell is optically connected to the wavelength selection module.

BRIEF DESCRIPTION OF THE DRAWINGS

FIGS. 24A, 24B and 24C are an embodiment of the optical layout for the UVC LED detector of the present invention.

FIG. 29A shows the top view of the optics bench assembly and FIG. 29B shows the isometric view of the optics bench assembly.

FIGS. 37A, 37B, 37C, 37D and 37E show drop test analysis of an embodiment of the optics bench assembly with shock mounts for choosing an optimal wall thickness.

FIG. 74 shows clustered design structure matrices ("DSM") for light interactions.

FIG. 75 shows clustered DSM for spatial interactions.

DETAIL DESCRIPTION

Liquid chromatography ("LC") is a technique in analytical chemistry used to separate, identify and quantify compounds in a mixture. Liquid chromatography techniques can be broadly classified into planar and columnar techniques. In both of the techniques, the sample can be first dissolved in liquid that is then transported to a liquid chromatography system.

In the column technique, pressurized liquid solvent containing a sample mixture can be passed through a column 22 filled with a solid adsorbent material. As the sample mixture is passed though the column 22, constituents of the mixture will interact differently with the column absorbent. In the mobile phase, compounds in the sample distribute or partition differently between moving solvent. The column particles are referred to as the stationary phase. Because constituents (also referred to herein as compounds) move at different speeds, different colored bands relating to different compounds can be generated. Arsenault, J. et al., *Beginners Guide to Liquid Chromatography*, 2nd ed. Waters Corporation, 2009.

In early liquid chromatography systems, high pressure of about 35 bar was used to generate the flow in packed columns. These systems were known as High-Pressure Liquid Chromatography ("HPLC"). The 1970s saw improvement in HPLC technology in developing pressures up to 400 bar and incorporating improved injectors, detectors and columns. With continued advances in performance with technologies such as smaller particles and higher pressures the acronym remained the same but the name was changed to High-Performance Liquid Chromatography (also referred to as "HPLC"). Furthermore, advancements in instrumentation and column technology have led to increases in resolution, speed and sensitivity in liquid chromatography. High performance can be achieved through the use of columns having particles as small as 1.7 microns and instrumentation with specialized capabilities can deliver the mobile phase at about 1000 bar and referred to as Ultra-Performance Liquid Chromatography ("UPLC").

Today, LC systems can identify compounds in trace concentrations as low as parts per trillion (ppt). Many variations exist in relation to the pressure with which the solvent is pumped through the LC system, i.e., low pressure liquid chromatography (approximately at 3 bar), high pressure chromatography (approximate 400 bar) and more recently ultra-high pressure liquid chromatography (approximate 1000 bar). HPLC and UPLC have application in many industries including pharmaceuticals, food, cosmetics, environmental matrices, forensic samples and industrial chemicals.

Figure 1:
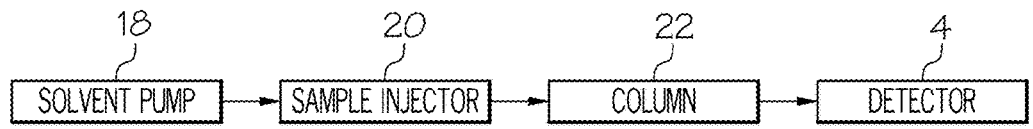
FIG. 1 represents a basic liquid chromatography process and set up, and components.

In its simplest representation a liquid chromatography system comprises four components: a solvent pump (not shown), a sample injector (not shown), a column 22 (stationary phase), and a detector 4. A general LC process and set up is generally represented in FIG. 1. Sample is pumped to the required pressure and injected into the stream of solvent. The mixture is then passed through the column 22, where the constituents of the sample are separated and the detector 4 is used to measure the quantity of constituent. A liquid chromatography system 2 can also include a sample manager (not shown), a solvent manager (not shown), a column heater (not shown) and/or a column manager (not shown). In the liquid chromatography system 2, the detector 4 is identifies constituents (compounds) in the mixture eluted from the chromatography column 22 by measuring a light absorbing property or other property of the column eluent.

Figure 78:
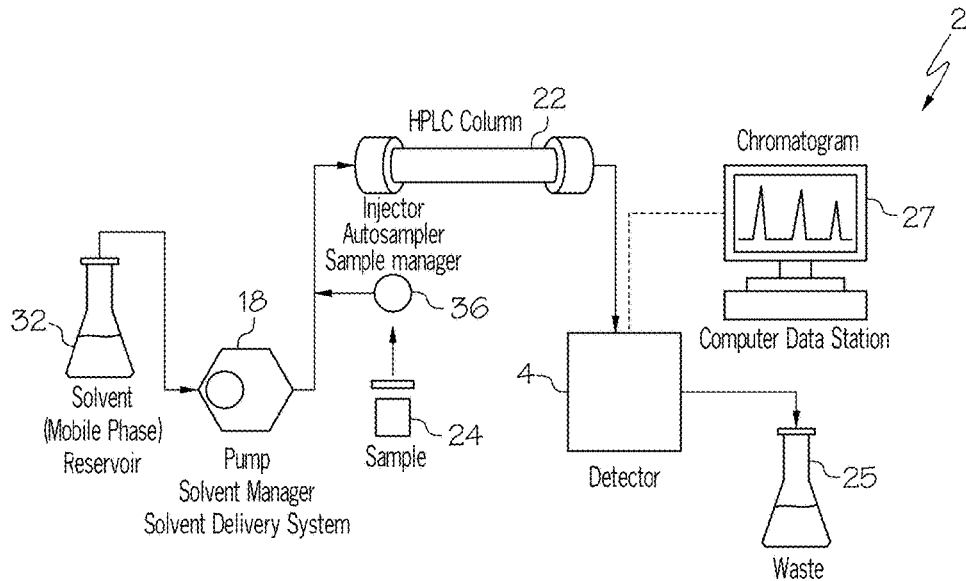
FIG. 78 depicts the components of a HPLC system.

The components of the liquid chromatography system 2 ("LC System") are shown in the FIG. 78. In FIG. 78, a reservoir 32 holds the solvent (also referred to as "the mobile phase"). A high-pressure solvent pump 18 in a solvent delivery system (not shown) or in the solvent manager (not shown) is used to generate and meter a specified flow rate of the mobile phase, typically milliliters per minute. An injector 36 in the sample manager 24 (also referred to as an autosampler) is able to introduce (inject) the sample into the continuously flowing mobile phase that carries the sample into the HPLC column 22. As noted herein, the column 22 contains the chromatographic packing material (not shown) required to effect the separation. This packing material is called the stationary phase because it is held in place by column hardware. The sample manager 24 directs flow of sample through the flow cell 66.

The detector 4 is needed to "see" the separated compound bands as they elute from the HPLC column 22. The mobile phase exits the detector 4 and can be sent to waste, or collected, as desired. When the mobile phase contains a separated compound band, LC system 2 provides the ability to collect this fraction of the eluate containing that purified compound for further study. This is called preparative chromatography. High-pressure tubing (not shown) and fittings (not shown) are used to interconnect the pump 18, injector 36, column 22, and other detector components to form the conduit for the mobile phase, sample, and separated compound bands.

The detector 4 is a component of the LC system 2 that identifies and quantitates the concentration of the sample constituents (see FIG. 78). The detector 4 records an electrical signal needed to generate the chromatogram on its display. Since sample compound characteristics can be different, several types of detectors have been developed as described herein. For example, if a compound can absorb ultraviolet light, a UV-absorbance detector is used. If the compound fluoresces, a fluorescence detector is used. If the compound does not have either of these characteristics, a more universal type of detector is used, such as an evaporative-light-scattering detector (ELSD). A powerful approach is the use multiple detectors in series. For example, a UV and/or ELSD detector may be used in combination with a mass spectrometer (MS) to analyze the results of the chromatographic separation. This provides, from a single injection, more comprehensive information about an analyte. The practice of coupling a mass spectrometer to an HPLC system is called LC/MS.

HPLC Operation

Figure 79A:
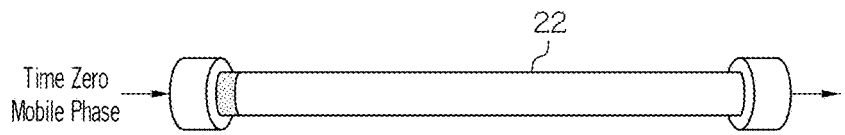
FIGS. 79A & 79B illustrates how a chromatographic column works—bands.
Figure 79B:
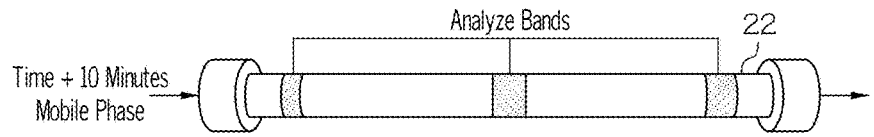

As shown in FIGS. 79A and 79B, mobile phase enters the column 22 from the left, passes through the particle bed, and exits at the right. Flow direction is represented by the arrows. As shown in G1, the column 22 at time zero (the moment of injection) when the sample enters the column 22 begins to form a band. The sample shown here, a mixture of yellow, red, and blue dyes, appears at the inlet of the column 22 as a single black band. In practice, this sample could be anything that can be dissolved in a solvent. Typically, the compounds would be colorless and the column 22 wall opaque, so the detector 4 is needed to see the separated compounds as they elute. After a few minutes, during which mobile phase flows continuously and steadily past the packing material particles, we can see that the individual dyes have moved in separate bands at different speeds. This is because there is a competition between the mobile phase and the stationary phase for attracting each of the dyes or analytes. Notice that the yellow dye band moves the fastest and is about to exit the column 22. The yellow dye likes (is attracted to) the mobile phase more than the other dyes. Therefore, it moves at a faster speed, closer to that of the mobile phase. The blue dye band likes the packing material more than the mobile phase. Its stronger attraction to the particles causes it to move significantly slower. In other words, it is the most retained compound in this sample mixture. The red dye band has an intermediate attraction for the mobile phase and therefore moves at an intermediate speed through the column 22. Since each dye band moves at a different speed, we are able to separate it chromatographically.

Figure 80:
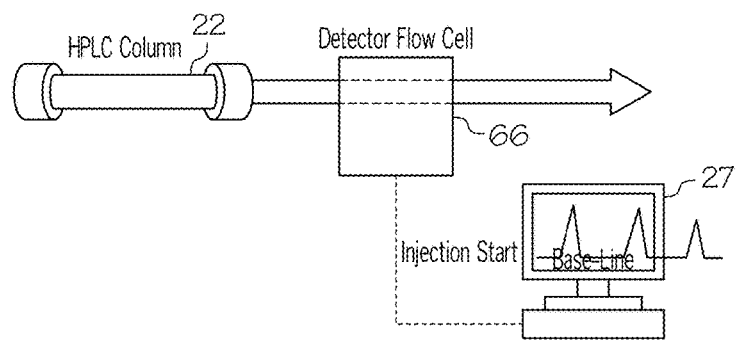
FIG. 80 shows an illustration of how peaks are created in the liquid chromatography system.

As the separated dye bands leave the column 22, they pass immediately into the detector 4. The detector 4 contains a flow cell 66 that sees or detects each separated compound band of the mobile phase (FIG. 80). As noted above, solutions of many compounds at typical HPLC analytical concentrations are colorless. The detector 4 has the ability to sense the presence of a compound and send its corresponding electrical signal to a computer data station 27. A choice can be made among many different types of detectors 4, depending upon the characteristics and concentrations of the compounds that need to be separated and analyzed, as discussed herein.

A chromatogram is a representation of the separation that has chemically (chromatographically) occurred in the LC system 2. A series of peaks rising from a baseline is drawn on a time axis. Each peak represents the detector 4 response for a different compound. The chromatogram is plotted by the computer data station 27. (FIG. 80). In FIG. 80, the yellow band has completely passed through the flow cell 66; the electrical signal generated has been sent to the computer data station 27. The resulting chromatogram has begun to appear on screen of the computer data station 27. Note that the chromatogram begins when the sample was first injected and starts as a straight line set near the bottom of the screen. This is called the baseline; it represents pure mobile phase passing through the flow cell 66 over time. As the yellow analyte band passes through the flow cell 66, a stronger signal is sent to the computer. The line curves, first upward, and then downward, in proportion to the concentration of the yellow dye in the sample band. This creates a peak in the chromatogram. After the yellow band passes completely out of the detector cell, the signal level returns to the baseline; the flow cell 66 now has, once again, only pure mobile phase in it. Since the yellow band moves fastest, eluting first from the column 22, it is the first peak drawn.

When the red band reaches the flow cell 66, the signal rises up from the baseline as the red band first enters the cell, and the peak representing the red band begins to be drawn. In this diagram, the red band has not fully passed through the flow cell 66. The diagram shows what the red band and red peak would look like if the process was stopped at this moment. Since most of the red band has passed through the cell, most of the peak has been drawn, as shown by the solid line. If the process is restarted, the red band completely passes through the flow cell 66 and the red peak would be completed (dotted line). The blue band, the most strongly retained, travels at the slowest rate and elutes after the red band. The dotted line shows a completed chromatogram upon conclusion of testing. Note that the width of the blue peak will be the broadest because the width of the blue analyte band, while narrowest on the column 22, becomes the widest as it elutes from the column 22. This is because it moves more slowly through the chromatographic packing material bed and requires more time (and mobile phase volume) to be eluted completely. Since mobile phase is continuously flowing at a fixed rate, this means that the blue band widens and is more dilute. Since the detector 4 responds in proportion to the concentration of the band, the blue peak is lower in height, but larger in width.

Currently, liquid chromatography can utilize a detector 4 different classes including: (1) bulk property detectors, and (2) specific property detectors. Bulk property detectors measure the bulk physical property of the column 22 discharge and specific property detectors measure a physical or chemical property of the solute. Bulk property detectors include a refractive index detector, an electrochemical detector, and a light scattering detector. Specific/solute property detectors include a UV-Visible light detector, fluorescence detector and mass spectroscopic detector.

TABLE 1

Different Types of Liquid Chromatography Detectors

| Bulk Property Detectors | Specific/Solute Property Detectors |
|---|---|
| Refractive Index Detector | UV-Visible Light (absorbance) Detector |
| Electrochemical Detector | Fluorescence Detector |
| Light Scattering Detectors | Mass Spectroscopic Detector |

UV-Visible Light detectors are specific/solute property detectors which operate in the UV and visible light spectrum by either using filters to get a specific wavelength or by splitting the incident light (using a prism or diffraction grating) from the light source before or after it has passed the sample. Intensity is measured after light has gone through the sample to calculate absorbance of the sample. Absorbance detectors can be further subdivided into two categories including fixed wavelength detectors and variable wavelength detectors. Fixed wavelength detectors use a narrow band pass optical filter to get monochromatic light from the source and therefore do not need to split the light. Variable wavelength detectors 4 split light into its constituent spectrum using a prism/diffraction grating. Variable wavelength detectors 4 include both scan and photodiode array detectors 254.

In UV scan detectors, either the photo-detector or the prism/diffraction grating 14 is moved via motors to allow for potentially monitoring the sample at each separate wavelength. A Tunable UV ("TUV") detector can be a tunable, dual-wavelength UV/Visible detector. Because of the inertia of the grating 14 and motor mechanism, at high speeds, switching between wavelengths at high speeds is not available.

In a photodiode array detector 254, referred to herein sometimes as "PDA detector," light after passing through the sample is split into its constituent wavelengths and are made incident on an array of photodiodes to allow the simultaneous monitoring at many different wavelengths.

Figure 2A:
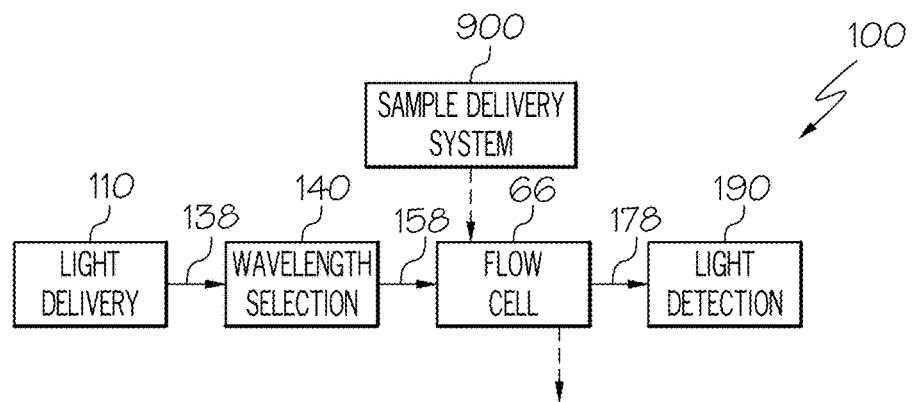
FIG. 2A provides a general diagram of an optical-based detector for liquid chromatography in which the flow cell is after the wavelength selection module.

As shown in FIG. 2A, the detector 4 provided herein is compatible for use in a liquid chromatography system 2 ("LC system"), particularly for use in an HPLC systems and UPLC systems. The detectors 4 provided herein comprise a light delivery system 110 having a light source 50, a wavelength selection module 140 comprising a digital micro-mirror device 8 ("DMD"), the flow cell 66 and a light detection unit 190. As noted herein, the detector 4 can be compatible with other liquid chromatography systems 2 including UPCC (or Supercritical Fluid Chromatography) or even in non-chromatographic applications such as monitoring process fluids in industrial processes.

Figure 2B:
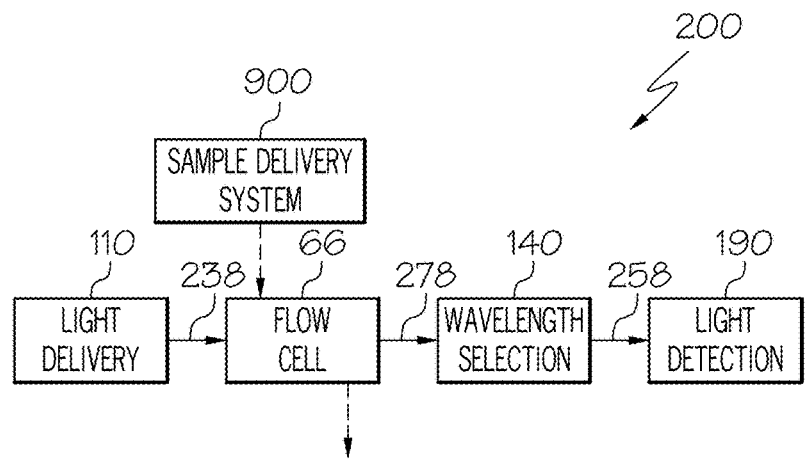
FIG. 2B provides a diagram of an optical-based detector for liquid chromatography where the flow cell precedes the wavelength selection module.
Figure 2C:
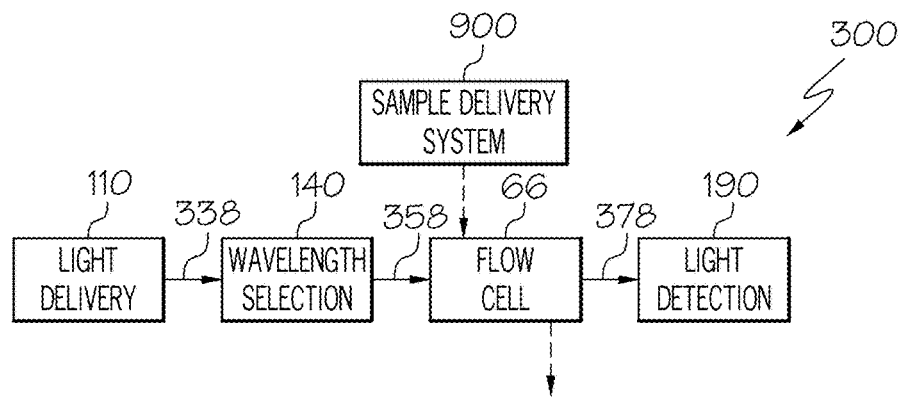
FIG. 2C provides a layout of the detector described herein.

With reference to the Figures, FIGS. 2A and 2B depict detectors of the present disclosure which can optically interrogate the contents of a flow cell 66. In the figures, dashed line arrows will indicate fluid or sample flow while block arrows denote light paths (sometimes referred to as light pathways. The difference between the systems in FIGS. 2A and 2B is the location of the flow cell 66. In FIG. 2A, the flow cell 66 follows the wavelength selection module 140. In FIG. 2B, the flow cell 66 precedes the wavelength selection module 140. There can be functional differences between the wavelength selection modules 140 and the flow cell 66 in both configurations.

The main difference between the two schemes of FIGS. 2A and 2B is described herein. Typically the wavelength selection module is placed after the flow cell in applications where the entire wavelength spectrum can be probed simultaneously. By contrast, this wavelength selection module is placed before the flow cell if the analyte to be identified is photosensitive, to minimize stray light, and to probe the optical properties at a single wavelength of interest. The latter may include fluorescence, specific absorption or refractive index measurement. In each case, the flow cell can be optimized to measure either the transmission (absorption), out of axis radiation (fluorescence) or beam steering (refractive index).

As described herein, the detector 4 can comprise an optics bench assembly 40 that comprises both optical components and structural components (combined sometimes referred to as the "optics bench assembly components"). Optical components of the optics bench assembly 40 can have: (1) an entrance slit 12 for light received by the detector 4; (2) a grating 14; (3) a digital micro-mirror device ("DMD") 8; (4) a spherical convex mirror 56; (5) a beam splitter 60; (6) a reference photodiode 62; (7) a main photodiode 64; and (8) a flow cell 66.

The structural components of the optics bench assembly 40 described herein can include: (1) a light dump 54 (sometimes referred to herein as a "light dump/shield" or a "light shield"); (2) an optics bench assembly casing 44; (3) an optics bench assembly cover 70; (4) a mirror 56, (5) a grating mounting mechanism 71; (6) a plurality of mounting brackets 72 and (7) a plurality of fasteners. 73

Depending upon the light source 50 of the light delivery system 110, it may be desirable to have the flow cell 66 placed after the wavelength selection module 140 in the optics bench assembly 40. For example, if the output of the light source 50 is broad band and includes wavelengths that may induce undesirable photochemical responses within the sample. Pre-filtering these wavelengths with the wavelength selection module 140 will insure that that the interrogated sample species is not altered from that which was delivered to the flow cell 66. As described herein, a suitable light source 50 includes various discharge lamps, such as deuterium or xenon lamps as well as composite light sources in which individual emitters such as a plurality of light emitting diodes ("LEDs") are so arranged to provide a range of wavelengths, each representing the center emission wavelength of one LED 6. An output of the light source 50 can be essentially monochromatic, such as from a laser, or a narrow band UV LED 6, or a discharge lamp emitting only a few spectral lines. The output of the light source 50 may be intense, in which case, the wavelength selection module 140 can comprise an optical attenuator (not shown). By having the flow cell 66 follow the wavelength selection module 140 (as in FIG. 2A), the wavelength of interest can be selected or tuned to match the spectral absorption features of the analyte of interest. In this case, wavelength selection can be accomplished through the use of a motorized mechanism which controls the angular position of a dispersing element such as a grating 14.

Figure 3A:
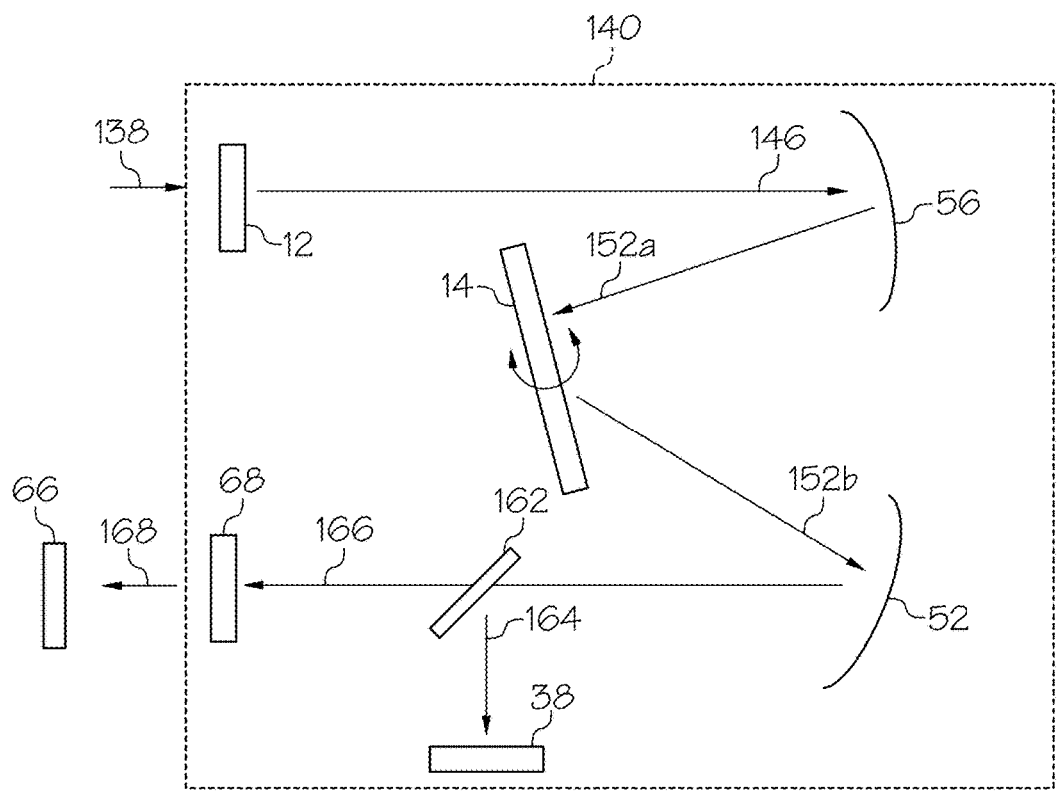
FIG. 3A provides a general diagram of a prior art optical-based detector for liquid chromatography in which the flow cell is after the wavelength selection module.

FIG. 3A provides a block diagram of the wavelength selection module 140 incorporating a grating 14. The entrance slit 12 defines a narrow width of an incident light beam 138 and sets the smallest achievable resolution by setting the image resolution at the detector plane, or how much wavelengths will overlap given a fixed exit slit, or pixel width. The optical resolution is inversely proportional with the exit slit width and typically ranges between 0.01 nm and 20 nm. Beyond the entrance slit 12, a first light beam 146 is collimated by a reflecting mirror 56 and is redirected as a second light beam 152a towards a plane reflective grating 14 where it is diffracted into its constituent colors. By rotating the grating 14 to specific angles, the wavelength of interest will be redirected as a third light beam 152b towards an output focusing element 52 that redirects a fourth light beam 166 to an exit slit 68. Some portion of the fourth light beam 166 incident at the exit slit 68 can be redirected as a fifth light beam 164 towards a reference detector 38 with the aid of a beam splitter 162, which may be as simple as a window transparent to all wavelengths of interest.

The rotation (in both directions) of the plane reflective grating 14 is about an axis perpendicular to the plane of FIG. 3A, as signified by the curly arrow. A sixth light beam 168 exiting through the exit slit 68 is directed towards the flow cell 66. After passage through the flow cell 66, the sixth light beam 168 can be converted to an electric signal by a light detection unit 190. In this configuration, light detection unit 190 can include transfer optics (not shown) to efficiently couple the light leaving the flow cell 66 to a single photodiode detector or a type similar to the reference detector 38.

Use of the reference detector 38 is beneficial in compensating for common-mode variations in light intensity that could otherwise confuse the interpretation of the signal from the light detection unit 190. For example, a reduction in light output from 110 of 1% could decrease the signal of the light detection unit 190 by substantially the same amount; if not compensated, this decrease would be interpreted by an absorbance detector (not shown) as an increase in concentration of the analyte. However, the reference detector 38 can report a similar decrease, and through signal ratio, eliminate the reporting of a false positive (or negative) analyte concentration.

Figure 3B:
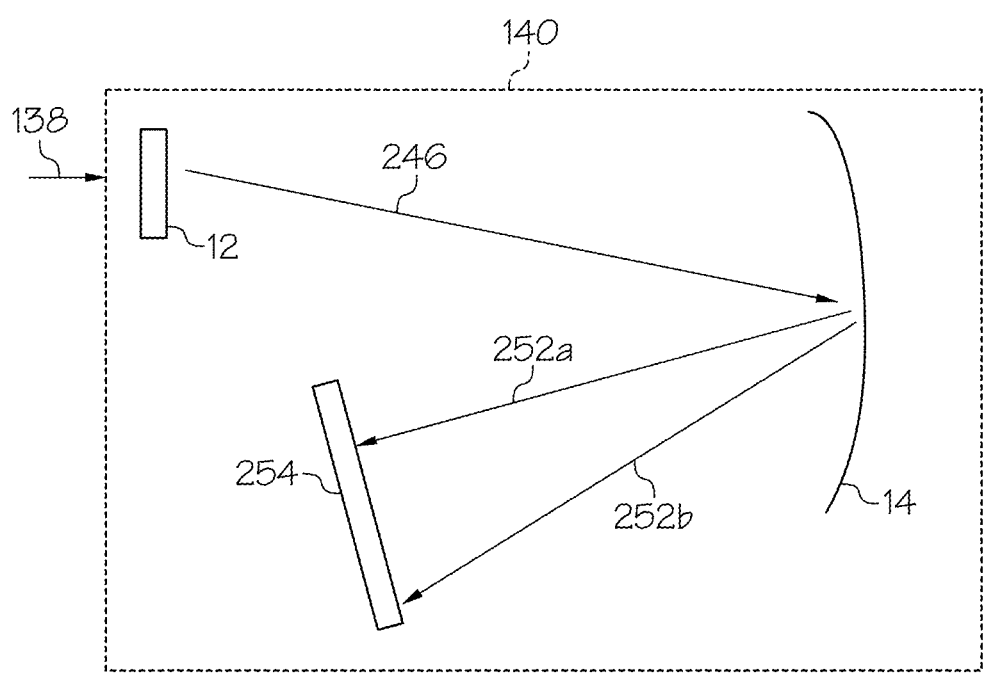
FIG. 3B provides a diagram of a prior art optical-based detector for liquid chromatography where the flow cell precedes the wavelength selection module.

In array detectors, the flow cell 66 preceding wavelength selection module 140 enables simultaneous detection of light at many wavelengths, without having to physically move a dispersing element (i.e., grating). A typical layout of such wavelength selection module 140 is shown in FIG. 3B. A first light beam 138 exits the flow cell 66 and passes through the entrance slit 12 and an emergent light beam 246 is collected by a concave grating 14, which both disperses and images the diffracted wavelengths into a single focal plane where an array detector 254 is located. Here, the array detector 254 is typically a linear array of pixels although 2D-imaging array or fiber bundle can also be employed. A given pixel may be between 10 to 200 microns wide and from 10 to 2500 microns tall. Two dispersed light beams 252a, 252b leaving an imaging grating 14 are illustrating the constituent colors or wavelengths of the emergent light beam 246 that have passed through the entrance slit 12 and are imaged at different locations along the array detector 254. Thus, the dispersed light beam 252a can correspond to a short wavelength and the dispersed light beam 252b to a longer wavelength. The mechanical width of the entrance slit 12 influences spectral resolution, basically establishing the minimum width of the focused colors at the array and how many pixels correspond to this width. For example, an entrance slit width of ~100 microns could result in image widths of similar size at the array detector 254; the height of this image depending upon how much of the entrance slit height is illuminated by light beam 138 as well as the mechanical height of each pixel. The illuminated height of the entrance slit 12 might range from tens of microns to several millimeters.

Certain advantages offered by each of the two methods (of differing flow cell location with respect to the wavelength selection module) can be realized with the incorporation of a digital micro-mirror array. In particular, the substitution of a digital micro-mirror array for the array detector 254 and followed by the flow cell 66 and light detection unit 190 can avoid potential issues associated with intense light sources yet permit tunability by eliminating a mechanical grating drive system and grating 14, replacing it with the highly reliable beam steering capabilities of the digital micro-mirror array. In the detector 4 described herein, the digital micro-mirror device 8 ("DMD") is employed to redirect selected regions of a focused light spectrum to an optical output pathway which is connected to a flow cell 66.

Figure 4:
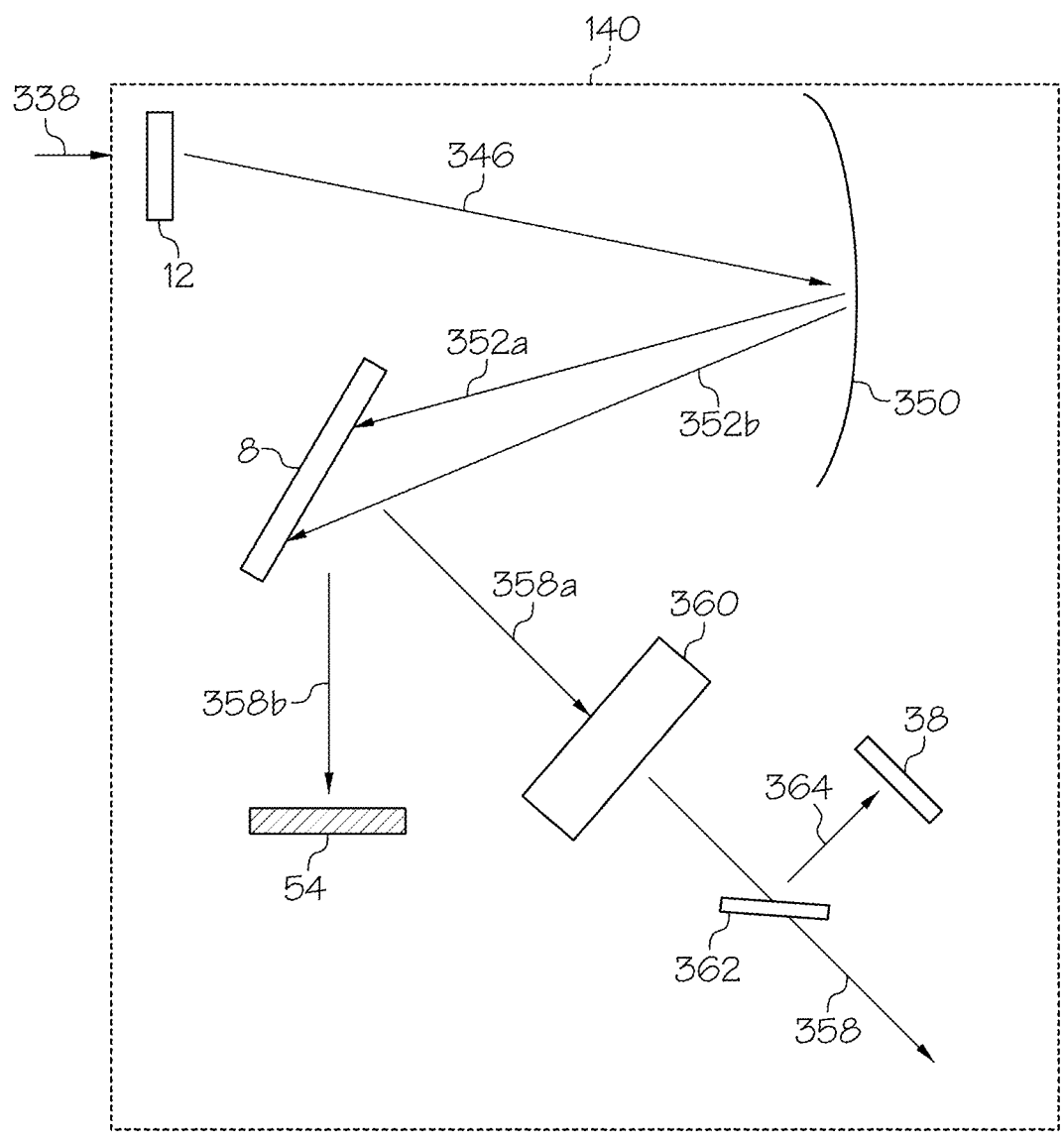
FIG. 4 illustrates an embodiment of the present detector in which a digital micro-mirror device ("DMD") is positioned at or near a focal plane of a spectrograph.

Referring now to FIG. 4, a light delivery system 110 directs a broad spectrum light beam 338 at an entrance slit 12 of a wavelength selection module 140 to generate the optical output pathway. After passage through the entrance slit 12, an incident light beam 346 is incident upon a spectrum dispersing element 350 to form a plurality of focused beams of constituent colors 352a, 352b at the DMD 8. By selective control of the micro mirrors (not shown), the focused beams of constituent colors 352a, 352b on the DMD 8 can be sent in two directions. One direction represented by a first reflected beam 358a along the optical output pathway that leads to an output beam 358 employed for subsequent analytical purposes such as transmission into the flow cell 66. The second direction represented by a second transmission beam 358b corresponding to transmission along the optical output path toward a light dump 54 that absorbs all incident light or alternatively to a secondary analytical pathway similar to the first reflected beam 358a but at a different wavelength. The first reflected beam 358a is first incident upon an optical output subsystem 360 that can include beam-shaping elements for controlling the shape and direction of an output beam 358 in the optical output pathway. An intensity referencing system (not shown) can be inserted after the optical output subsystem 360 for providing a reference light beam 364 with the aid of a partial reflecting element 362 and the reference detector 38.

Figure 5A:
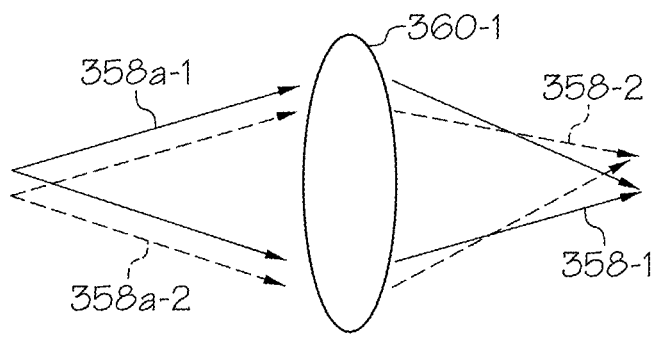
FIG. 5A illustrates methods of focusing a light beam from the DMD through an optical output system (a component of the detector) into distinct images.

The optical output subsystem 360 can refocus the spatially resolved colors at the DMD 8 into distinct locations at an output focus point of the optical output beam 358 and in the optical output pathway. Thus, the optical output subsystem 360 can be a simple lens, a reflecting mirror or an aspheric surface such a reflecting ellipse or lens. As shown in FIG. 5A, spatially resolved colors at the DMD 8 such as a first output beam 358a-1 or a second output beam 358a-2 are imaged to output beam locations as an imaged output beam 358-1 and an imaged output beam 358-2, respectively. Here, individual rays within the beam leaving the DMD 8 are shown in conventional fashion with an arrowhead indicating direction of travel; one pair of rays is shown as dot-dashed lines to distinguish it from the other pair. In this configuration, the different colors are focused into distinct images, each of which can be selectively turned on and off and directed to various flow cells that can operate at different analytical wavelengths. It may also be beneficial in some cases to employ a field lens (not shown) as a cover slip for the DMD 8; the optical power of the field lens is chosen to image the clear aperture of element 358 onto element 360-1, thereby retaining a compact beam size at this element.

Figure 5B:
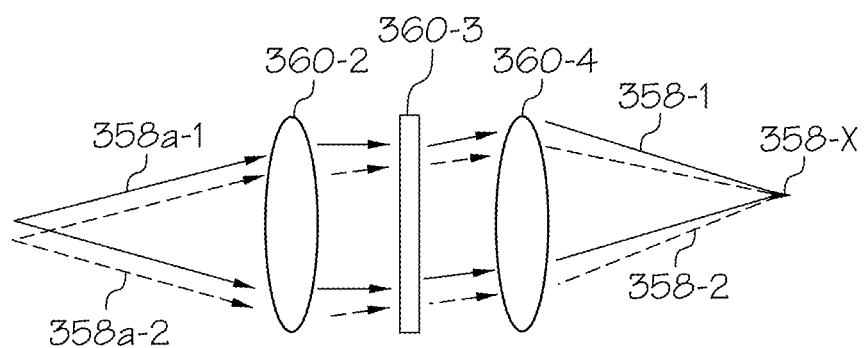
FIG. 5B illustrates the methods of FIG. 5A with optical output system configured to achieve a common focus for all wavelengths.

In another configuration, the optical output subsystem 360 can comprise of several elements which function to recombine all focused colors at the DMD 8 into a single image at the output focus of beam 358. Again, omitting the reference channel components for clarity, FIG. 5B depicts one combination of elements to achieve this objective. A first lens 360-2 collimates the beams diverging from the DMD 8; these constituent collimated beams are incident upon a transmission grating 360-3. The angles of incidence at the grating vary with wavelength or color. Through grating spacing and incidence angles, the diffracted beams transmitted through the grating 14 are rendered parallel to one another and may be brought to a common focus by a second lens 360-4. The common output focus for all colors comprising the beam leaving the DMD 8 is denoted 358-X. A single focal point for all colors is advantageous in terms of minimizing the size of the input face of the flow cell 66, leading to small flow cell volumes, and can be advantageous for detecting narrow peaks eluting from small bore or capillary scale liquid chromatographic columns 22. Use of a field lens on DMD 8 can also assist in maintaining a compact beam size through components comprising this variation of the output optical system.

Other combinations for the detector 4 include the DMD 8 as the entrance slit or exit slit. In this configuration, each of the mirrors of the DMD 8 acts as an on/off switch by directing the light either to a beam dump or to the subsequent optical elements. The number of on-element in the horizontal and the vertical direction will define the width and the height of the variable slit and can be dynamically assigned. At the input side, the DMD 8 will define the size of the object, which can impact the imaging resolution and optical throughput. At the output side, the DMD 8 would define the spectral bandwidth being analyzed by a single element detector 4 in an analogous way to pixel bunching in imaging array.

Typically, the optical coupling is optimized to fill the lumen of the flow cell 66 to increase the optical throughput. Having a concentric long or short path flow cell design, the light intensity distribution could be shaped to have most of the light entering in the central portion (long pathway) with some residual light going into the outer portion to increase the dynamic range of the measurement. Alternatively, an abberrated or oversized image at 358-X can be used for distinct flow cells (long/short path).

Relevant Optical Theory

Snell's Law: Index of Refraction

For any transparent medium, the index of refraction for that medium, $\eta_m$, is defined as the speed of light in a vacuum, c, divided by the speed of light within that medium, $c_m$, as shown. Peatross, J. W. P., *Physics of Light and Optics*, 2008.

$$\eta_m = \frac{c}{c_m} \tag{1}$$

Figure 6:
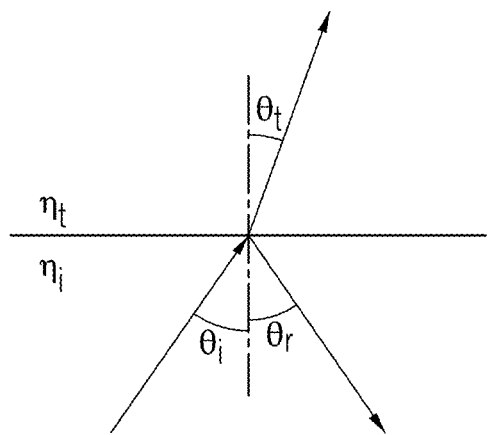
FIG. 6 and FIG. 7 demonstrate Snell's law for Total Internal Reflection.

Snell's Law describes the way light is transmitted at the interface of two mediums. As seen in FIG. 6, light will bend when passing between mediums which have different indices of refraction. This phenomena is described by Snell's law, given in Equation 2, where the ratio of the sines of the incident and transmitted angles is equal to the ratio of the indices of refraction in the two mediums. Id.

$$\frac{\eta_t}{\eta_i} = \frac{\sin\theta_i}{\sin\theta_t} \qquad (2)$$

Snell's Law: Total Internal Reflection

By solving Snell's law for $\theta_t$ as shown in Equation 3, a critical angle $\theta_c$ at which $\theta_t$ becomes imaginary, is provided by Equation 4.

$$\theta_t = \sin^{-1}\left(\frac{\eta_t}{\eta_i}\sin\theta_i\right) \qquad (3)$$

$$\theta_c = \sin^{-1}\left(\frac{\eta_t}{\eta_i}\right) \qquad (4)$$

Figure 7:
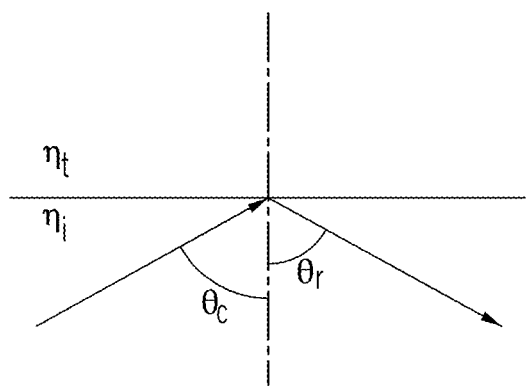

All light incident at or below the critical angle will reflect completely without any transmission through the second medium. This effect allows optical fibers to transmit light over large distances or along a specific pathway with little loss, as shown in FIG. 7.

Numerical Aperture

The numerical aperture ("NA") of an optical element is a dimensionless number which is defined in Equation 5, as the refractive index of the medium, n, times the sine of the half angle of the element's acceptance cone, α. B. Wolf, *Principles of Optics*, 1970. The numerical aperture squared may be thought of as the light gathering power of the element.

$$NA = n \sin \alpha \qquad (5)$$

Figure 8:
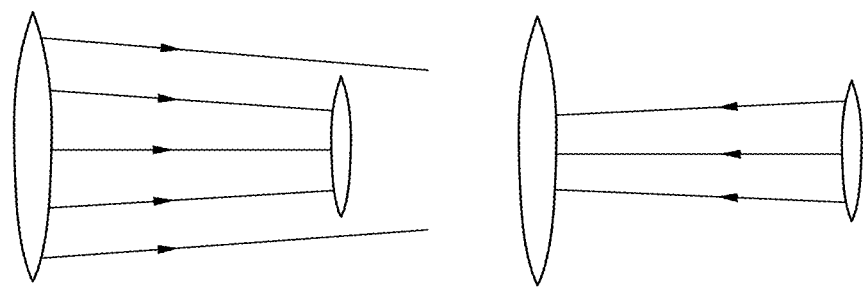
FIG. 8 shows optical coupling for elements with mismatched numerical apertures.

In FIG. 8, we can see what happens when we couple two optical elements together which have mismatched numerical apertures. Working through the optical system in one direction, the second element of the pair will be overfilled and the extra light will be unable to propagate through the rest of the system properly. If, instead, we start from the other direction the second element will be under-filled. The coupling efficiency, or fill factor, for the second element will be the ratio of squares of their numerical apertures as shown in Equation 6.

$$\eta_{coupling} = \frac{NA_{element}^2}{NA_{source}^2} F_{element} \qquad (6)$$

Etendue

The etendue of a detector can be defined in Equation 7, as the cross sectional area of the source, $A_s$ times the solid angle through which the light propagates, $\Omega$. It can be thought of as the ability of an optical system to accept light.

$$\varepsilon = A_s \Omega \qquad (7)$$

For small solid angles, $\Omega$ will be linearly proportional to the numerical aperture squared and the expression for etendue can be written as shown in Equation 8. Peatross, J. W. P., *Physics of Light and Optics*, 2008.

$$\varepsilon = A_{s\pi NA}^2 \qquad (8)$$

Optical Power

Having the etendue, the flux, $\phi$, or optical power, passing through it can be calculated by simply taking the product of the Etendue and the radiance of the source, as shown in Equation 9. Id.

$$\phi = \varepsilon R \qquad (9)$$

Fraunhofer Single Slit Diffraction

When coherent light passes through a narrow slit in a plane normal to the light's Poynting vector, it produces interference patterns which in the far-field are well described by the Fraunhofer diffraction equation, given in Equation 10. B. Wolf, *Principles of Optics*, 1970.

$$I = I_o\left(\frac{\sin x}{x}\right)^2 \qquad (10)$$

Where I is the intensity, $I_o$ is the intensity at the center of the diffraction pattern, and with minima occurring wherever x is an integer multiple of $\pi$. Id.

Grating Theory

Figure 9A:
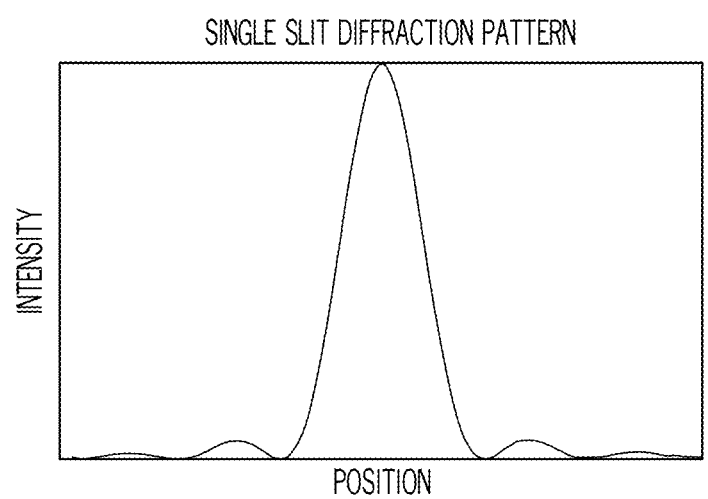
FIGS. 9A, 9B and 9C show Fraunhofer Diffraction Patterns for a single entrance slit (FIG. 9A), a double slit (FIG. 9B) and ten slits (FIG. 9C).
Figure 9B:
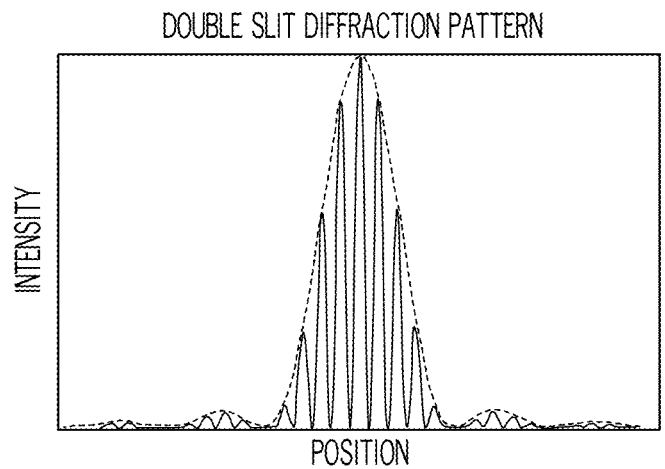
Figure 9C:
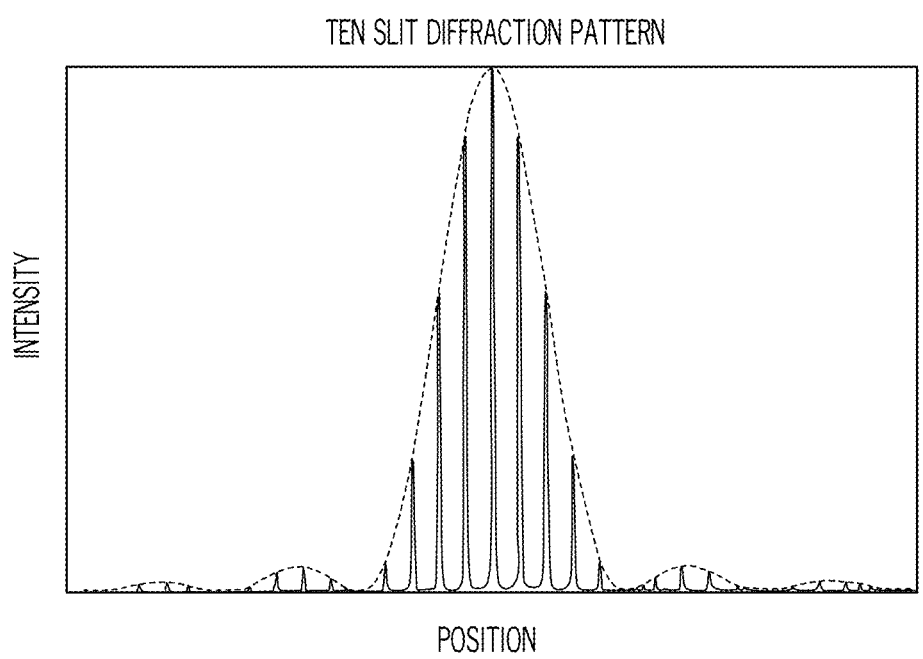
Figure 10:
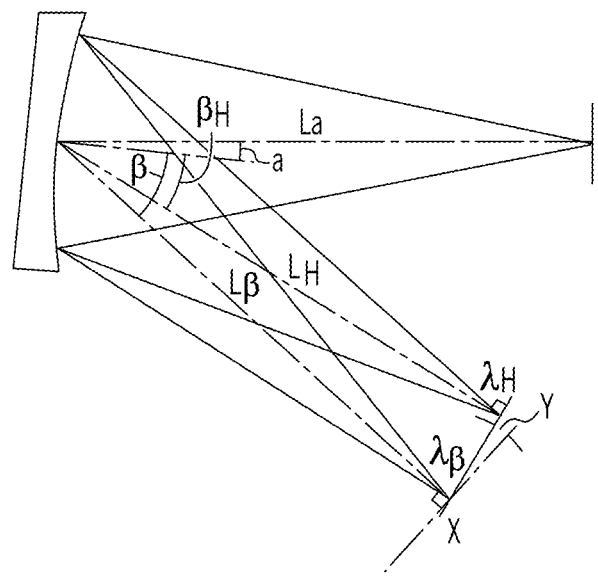
FIG. 10 is a linear wavelength dispersion of a spherical grating FIG. 11 show the spectral range of UVC light sources.

If more than one slit are arranged in a pattern, the effects of the interference are compounded. As shown in FIGS. 9 and 10, with more slits, the peaks become taller and narrower. Because the location of the peaks is dependent upon the wavelength of diffracted light, this effect can be used to sort light based on wavelength. If a repeating pattern of grooves is used in a reflective surface rather than slits, more of the optical power is retained. Such an optical element is called a reflective grating 14. The diffraction off of such a grating is described by the grating equation, as shown in Equation 11:

$$\sin \alpha + \sin \beta = kn\lambda \qquad (11)$$

Where $\alpha$ is the incident angle, $\beta$ is the diffracted angle, k is the order of diffraction, n is the groove density, and $\lambda$ is the wavelength. From Equation 11 and the geometry shown in FIG. 10 an expression for the linear dispersion of a spherical grating can be derived in nanometers per millimeter, which is provided in Equation 12 below:

$$\frac{d\lambda}{dx} = \frac{10^6 \cos\beta\cos^2\gamma}{knL_H} \qquad (12)$$

Digital Micro-mirror Devices

As provided herein, the detector 4 comprises a digital micro-mirror device ("DMD") 8 and a light source 50. In an embodiment, one or more Ultraviolet Light Emitting Diode ("UV-LED") 6 can be provided as the light source. Alternatively, the light source 6 can be a deuterium lamp or a zeno lamp. As described herein, an optics bench assembly 40 having certain structural components on which the optical components of the detector 4 are mounted.

DMD 8 is an opto-electro-mechanical device that is smaller and lighter than current mechanical gratings used in liquid chromatography systems. DMD 8 can be used in combination with a diffraction grating to separate light of different wavelengths into finer resolution and at a far higher frequency. The detector 4 having both UV-LEDs 6 and DMD 8 can have a modular architecture, where LEDs can be replaced with relative ease.

The digital micro-mirror device 8 contains arrays of thousands to millions of microns scale mirrors fixed to mems actuators which allow each individual mirror to be positioned at either ±θ° from its neutral "flat" state. This allows arbitrary patterns of light to be imaged at high speeds. For a photodiode the shot noise power which arises from the quantized nature of light, is given by Equation 13.

$$\overline{i_n^2} = 2qB(I_{signal} + I_{dark}) \quad (13)$$

Where q is the charge of an electron, B is the measurement bandwidth in Hz, and I is current. If we assume that dark current is much smaller than the signal current and solve for the root mean square we can find the shot noise in the current coming out of the photodiode, as shown in Equation 14.

$$i_{n_{rms}} \cong \sqrt{2qBI_{signal}} \quad (14)$$

By dividing the signal current by this expression we can find the signal to noise ratio, SNR, for a system dominated by shot noise, given in Equation 15.

$$SNR_{sn} = \sqrt{\frac{I_{signal}}{2qB}} \quad (15)$$

The signal to noise ratio is proportional to the square root of the signal strength.

Light Source Selection

The Ultra Violet ("UV") emitting light source 50 includes various gas arc lamps and hot filament lamps, such as deuterium arc lamps, mercury arc lamps, xenon flash lamps, quartz and tungsten halogen lamps, and UVC LEDs. LEDs can be employed singly, such as a 250 nm LED 6 or combined into groups, such as for example 11 LEDs with center wavelengths from 220 nm to 320 nm. Many factors are considered when selecting a light source 50 for UV absorption spectroscopy including the spectral range emitted by the source, total irradiance (or optical power output) and its spectral distribution, output stability, efficiency, lifetime, startup time, and the cost of the light source.

Figure 11:
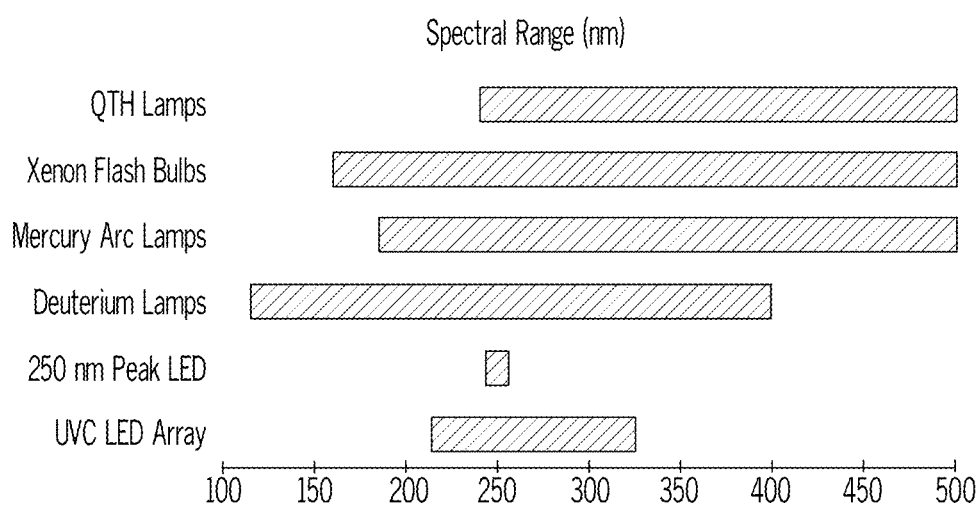
Figure 12:
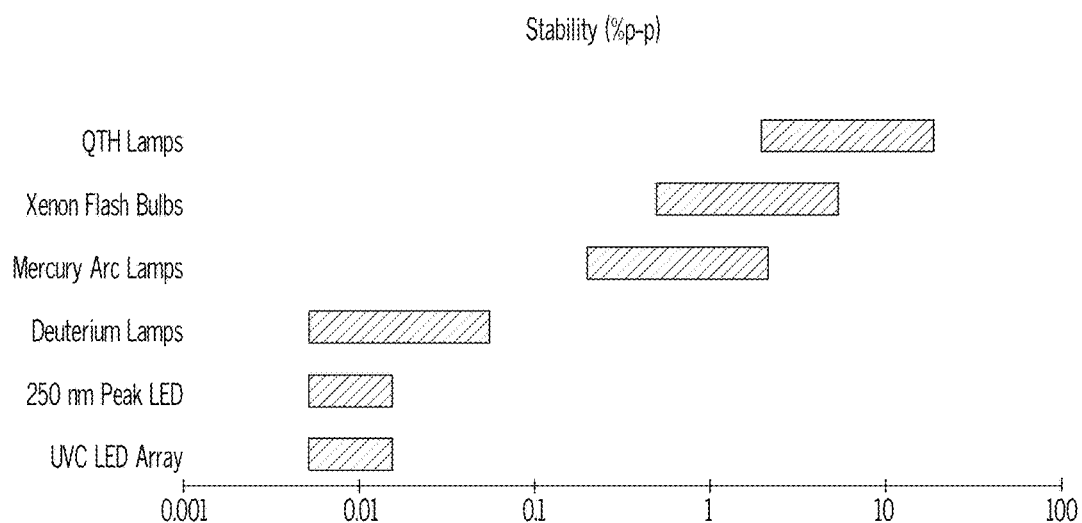
FIG. 12 depicts the stability of UVC light sources.

As shown in FIG. 11, the spectral range emitted by a light source 50 sets the limits for the wavelengths at which a spectrometer can detect absorption. In UV absorption spectroscopy, the signal is a decrease in intensity of the light exiting the flow cell 66 caused by sample absorption. As a result, the process is extremely sensitive to short term fluctuations in the intensity of the light source. In FIG. 12, the stability of various light sources for each type and shows deuterium lamps and LEDs has a similar level stability which is two orders of magnitude better than any of the other sources.

With regards to optical power and spectral irradiance, Beer's law informs that when the light throughput of the flow cell 66 is increased, at some point the sample will saturate and be unable to absorb additional light. Therefore, arbitrarily increasing light throughput does not always aid in detection. In fact, it can make detection more difficult. If the steady state throughput is many orders of magnitude higher than signal, the sensor and associated electronics will saturate if they have to small a small dynamic range, or if a large dynamic range is used, it could lack the sensitivity of a sensor with a much smaller dynamic range. Vickrey, T. M., *Liquid Chromatography Detectors*, Vol. 23. CRC Press, 1983. However, if the geometry of the flow cell is varied, we will notice that the etendue and, thus, the optical power throughput scales as the diameter of the flow cell squared, as shown in Equations 8 & 9.

Figure 13:
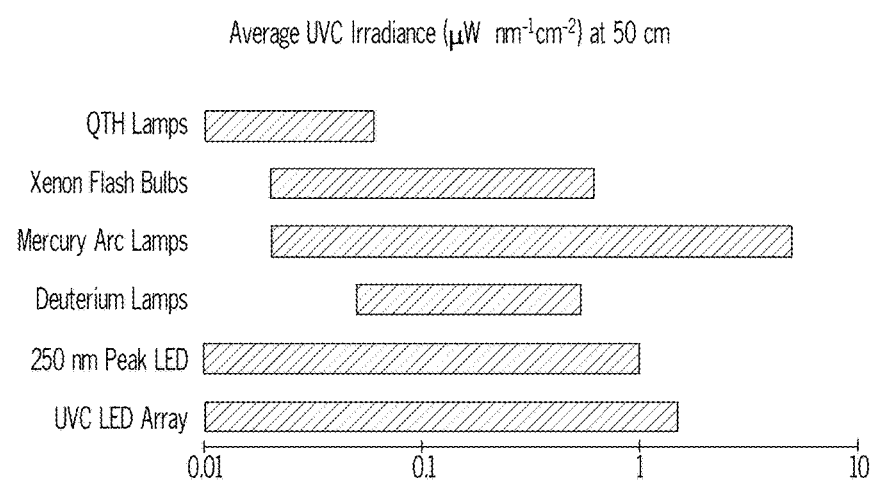
FIG. 13 shows the average irradiance of UVC sources.

Reducing the diameter of the flow cell 66 reduces the minimum sample volume required by the same factor squared, assuming the same absorption length is maintained. Therefore, optical throughput can be increased proportionally when reducing flow cell volume to maintain the same level of signal. As a result, the optical power provided by a source sets a lower bound on the volume of flow cell in conjunction with that source. In FIG. 13, we can see the average spectral irradiance, or optical power per nanometer of bandwidth across the UVC spectrum typical for each type of light source.

Figure 14:
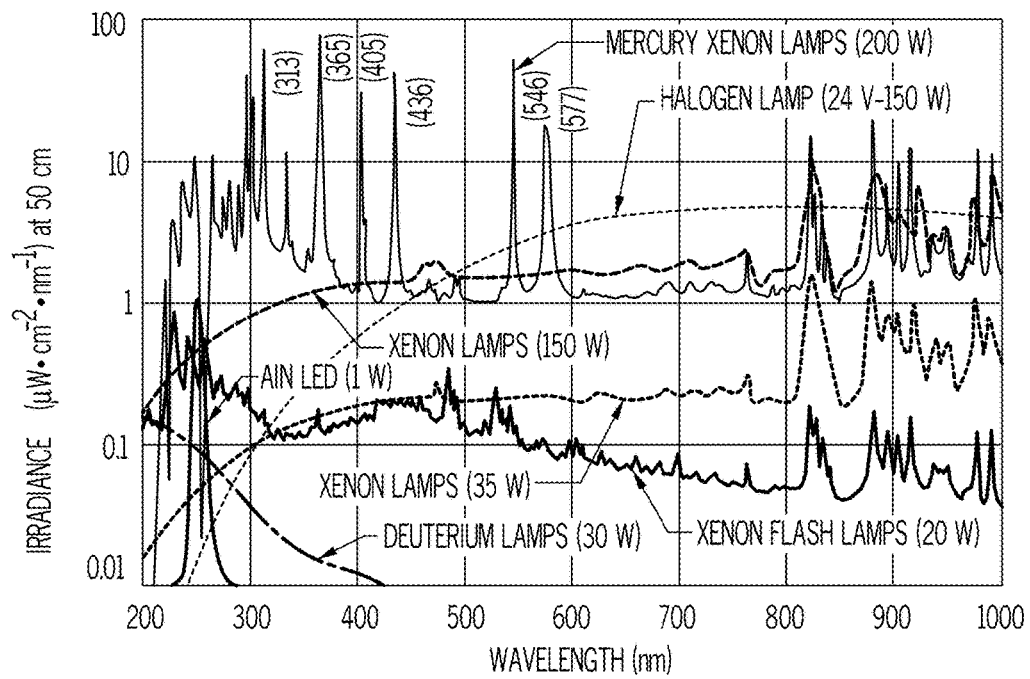
FIG. 14 shows the spectrum of UVC light sources.

As shown in FIG. 13, shows average UVC irradiance at 50 cm. High temperature, broadband light sources often have high sensitivity to temperature changes and are typically designed to have a single operating point. AlN LEDs exhibit little change to their peak wavelength either from temperature changes or when increasing or decreasing their driving current. As a result, we can easily modulate the irradiance of the LEDs by changing their driving current without adversely affecting their spectral output. FIG. 14, shows a small handful of representative irradiance spectrum of the various light sources.

Figure 15:
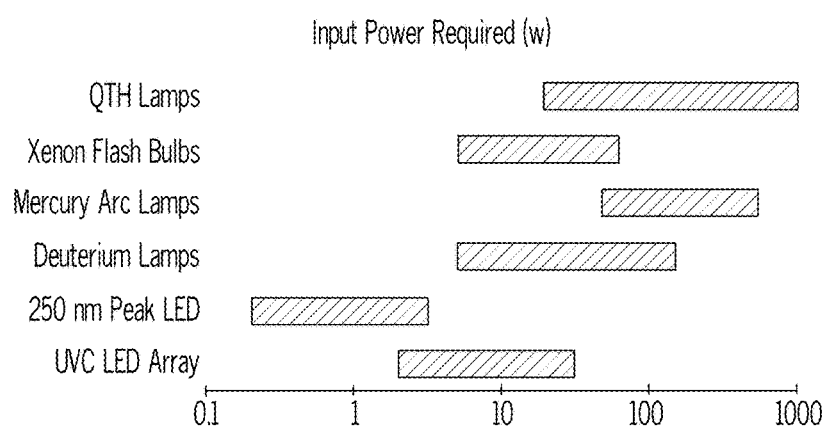
FIG. 15 depicts the various power requirements of UVC light sources.

As shown in FIG. 15, there is a range of power requirements for each type of light source. All UVC light sources have relatively small wall plug efficiencies so all of its power can be assumed to effectively be dissipated as heat. Traditionally the light source 50 can have significant heat output, 10 s to 100 s of Watts, managed in such a way that it does not adversely affect the sample or the spectrometer. Often this fact drives large facets of product architecture for existing detectors, driving their size, overall power requirements, and eliminating any possibility of portability.

Figure 16:
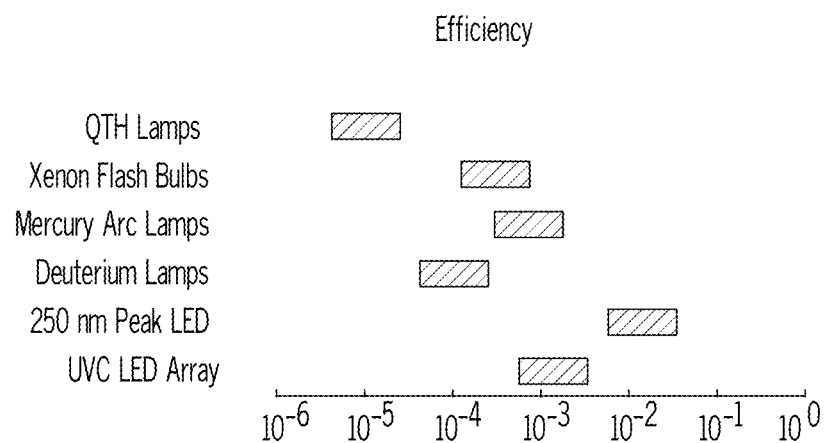
FIG. 16 depicts a comparison of light source efficiency based on application in UVC absorption spectroscopy.

Determining efficiency that can fairly and equally apply to all light sources is not straight forward. The approach presented herein is based on UVC absorption spectroscopy. Selectable wavelength detectors tend to have a bandwidth of 5 nm. Therefore, to compare the efficiency of these sources, as shown in FIG. 14, the total optical power output between 250 nm and 255 nm is estimated from each spectral irradiance curve and divided that number by the respective input power. The result is the approximate efficiency of each type of source as it would be used for UVC absorption spectroscopy. (FIG. 16).

Although the efficiency of an array of LEDs is comparable to that of a Mercury arc lamp or a Xenon flash bulb, the benefit of each is that the individual wavelengths can be turned off and on again as needed. This gives LEDs an advantage of at least two orders of magnitude in raw efficiency over any other source. When adding in the ability for all of them to be turned off when they are not actually being sampled, they have the potential to improve their effective efficiency by another two orders of magnitude over all traditional sources other than Xenon flash bulbs.

Figure 17:
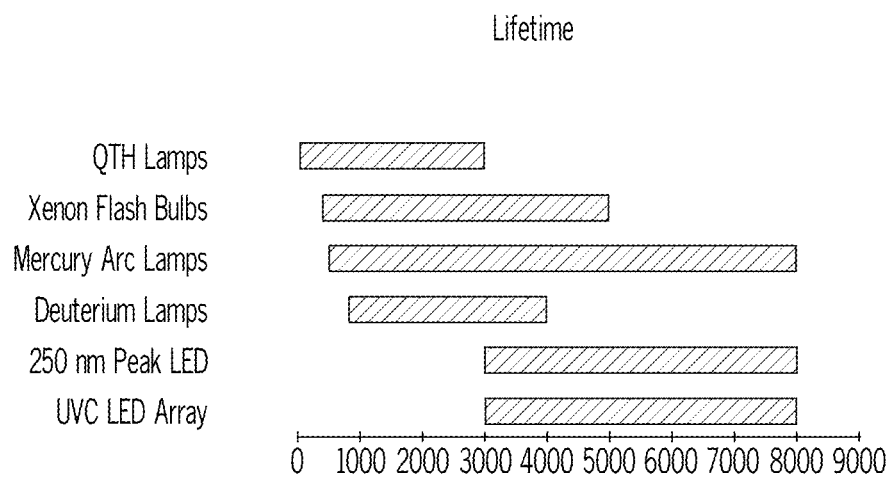
FIG. 17 depicts the expected lifetime for different types of UVC light sources.

Lifetime of the light source 50 can be defined as the average time it takes for the peak irradiance of the source to fall to half its initial value. FIG. 17 charts the range of expected lifetimes for each type of UVC light source. The lifetime for a typical traditional UV lamp is 2000 hours. The lifetime for a UVC AlN LED starts around 3000 hours if it is run continuously at its maximum drive current. However, if the drive current is lowered from 100 mA to 20 mA, its expected lifetime goes up to 8000 hours. The tradeoffs these LEDs exhibit between lifetime, age, drive current, and irradiance could be harnessed by creating an active driver for each LED which gradually increases the drive current provided as it ages. Such a light source would have a consistent irradiance throughout its lifetime, a strong signal at the end of its life, and a significantly extended lifetime compared to a light source which started at a higher brightness and decayed steadily to half intensity over its life. These tradeoffs have a great deal of potential for other applications such as a software widget for the detector which allows the user to adjust the drive current themselves. In this way, one device could equally well serve customers who want the higher brightness even if it means replacing a lamp every 500 hours, as well as, customers who wanted to stretch out the life of their lamp and live with less signal.

Figure 18:
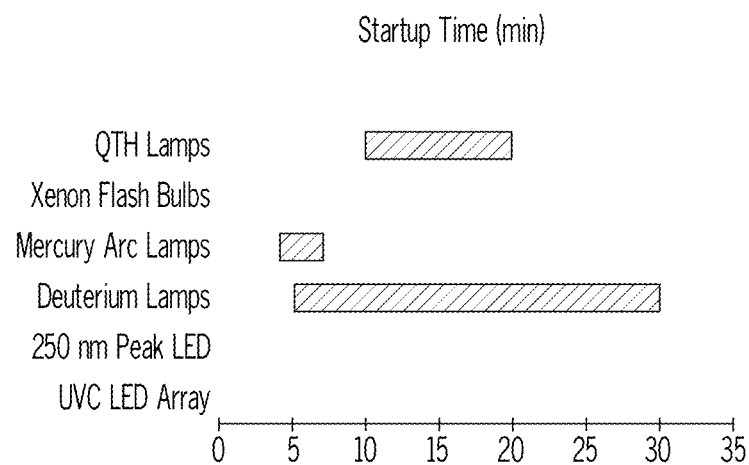
FIG. 18 depicts the average startup times of various UVC light sources.

Similarly, the average startup times for the various light sources is provided in FIG. 18. For most of the lamps, the startup time is when the lamp reaches thermal steady state, and thus maximal optical stability. For the Xenon flash bulbs and the LEDs it is the rise time to achieve approximately full brightness. The startup time of the light source is one factor impacts both the lifetime and the efficiency of the system. When the light source 50 requires a longer startup time it is consuming more energy, none of which is usable for absorption spectroscopy. This lowers its overall efficiency. It is also using up minutes of its lifetime which reduces its effective lifetime for detection. These effects are compounded when considering user behavior. Long startup times prompt users to start up the machine well in advance of when they want to start using it, and it encourages them not to shut it off for short-duration breaks in running samples. These behaviors further exacerbate the reduction in overall efficiency and effective lifetime.

Figure 19:
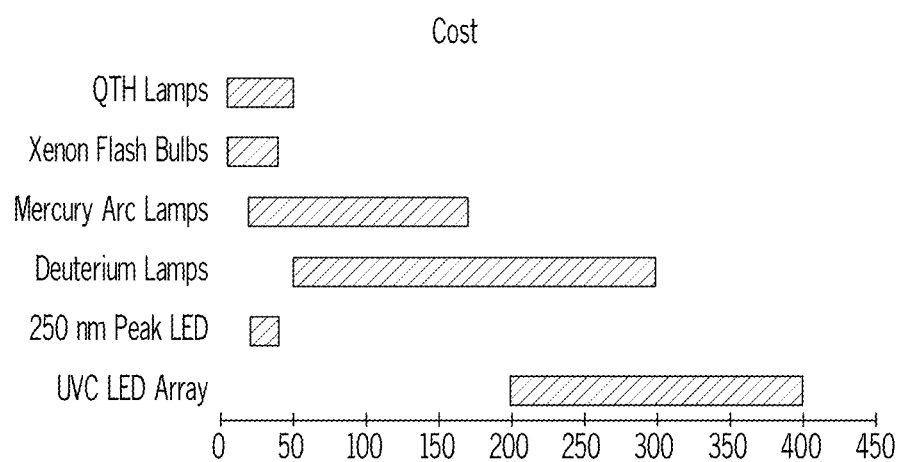
FIG. 19 depicts estimated present costs of UVC light sources.

Finally in the selection of the light source 50 and power supply (not shown), an important factor is the relative cost of each light source and its power supply, which in some cases costs more than the light emitter itself. To approximate the relative cost of the light sources shown in FIG. 19, we assume that each can be purchased for one tenth its retail unit value when purchased wholesale in production quantities. The array of LEDs currently exceeds the cost of any traditional light source. However, when comparing the current cost for these light sources, it is important to consider the differences in the product life cycle stage between the LEDs and the other sources. While certain traditional light sources are moderately mature technologies, AlN based LEDs have only been commercially available for a few years. For new product development, it is important to keep in mind that this graph is likely to look different three to five years from now.

UVC LED

The LED 6 (sometimes referred to as "UVC LED") produces light by taking advantage of the bandgap in semi-conductors. Electrons in a semi-conductor junction are electrically excited across its bandgap and subsequently de-excite, radiating light in the process. The wavelength of light emitted by an LED is determined by its bandgap. To create LEDs which emit at lower wavelengths requires semiconductors with larger bandgaps. Group III nitrides have bandgaps from 2 to 6 eV which make them ideal candidates for LEDs emitting UV radiation. Ponce, et al., *Nitride-based Semiconductors for Blue and Green Llight-emitting Devices*, Nature, Vol. 386, No. 6623, 351-359, 1997. AlN has a particularly broad bandgap, 6.1 eV, making it ideally suited for the construction of low wavelength LEDs. In 2006, researchers from NTT Basic Research Laboratories were able to develop a PIN type AlN LED with an emission wavelength of 210 nm. Taniyasu, et al., *An Aluminium Nitride Light-emitting diode with a Wavelength of 210 Nanometres*, Nature, Vol. 441, No. 7091, 325-328, 2006.

As AlN LEDs emitting lower wavelengths have been developed, defects in the crystalline structure have become a prominent problem. Defects can provide pathways for electrons to relax thermally without radiating. As a result, the efficiency and light output of an LED 6 go down while its heat output goes up. Many AlN LEDs are built upon a substrate of either Silicon Carbide or Sapphire. Mismatch between the crystal lattices of AlN and these substrate lead to dislocation densities of 108 to 1010 defects per square centimeter or even higher. Taniyasu, et al., *An Aluminium Nitride Light-emitting diode with a Wavelength of 210 Nanometres*, Nature, Vol. 441, No. 7091, 325-328, 2006; Rojo, G., *Report on the Growth of Bulk Aluminum Nitride and Subsequent Substrate Preparation*, J. Cryst. Growth, Vol. 231, No. 3, 317-321, 2001; Muramoto, Y. et al., *Development and Future of Ultraviolet Light-emitting Diodes: UV-LED Will Replace the UV Lamp*," Semicond. Sci. Technol., Vol. 29, No. 8, 084004, 2014

UV LED chips grown on single crystal AlN and the substrate itself have nearly identical lattice structures and therefore dislocation densities of only 103 to 104 defects per square centimeter is possible, a tremendous improvement over LEDs grown on other substrates. Rojo, G., *Report on the Growth of Bulk Aluminum Nitride and Subsequent Substrate Preparation*, J. Cryst. Growth, Vol. 231, No. 3, 317-321, 2001. LED chip sources have viewing angles of 120° or more which gives them extremely large numerical apertures, NA=0.87 for 120°. Crystal Is, *Crystal IS SMD UVC LED*, 1-8. This presents a challenge when coupling to UV transmitting optical fibers which have numerical apertures of about 0.28. Bell et al., *Multimode Fiber, Vol.* 10, 1-20, 2005. Assuming the diameter of the fiber is larger than the diameter of the source (LED chip) and not including Fresnel losses, the theoretical maximum coupling efficiency as given by Equation 6 is 6.4 percent. However, use of specially designed refractive-reflective micro lenses have the potential to increase the coupling efficiency, raising it as high as forty percent. If instead we assume the use of such a micro lens, we can assume a coupling efficiency of twenty percent. Rooman, C., *Reflective-refractive Microlens for Efficient Light-emitting-diode-to-fiber Coupling*, Vol. 44, September 2005, 1-5, 2015.

Wavelength Selection

UV absorption spectroscopy detectors 4 for liquid chromatography can be grouped into three major groups: (1) single wavelength detectors such as models based on a mercury arc lamp line; (2) tunable UV detectors and (3) photodiode array detectors 254b. Tunable UV and photodiode array detectors can both implement a strategy to distinguish between absorption at different wavelengths of light.

Figure 20:
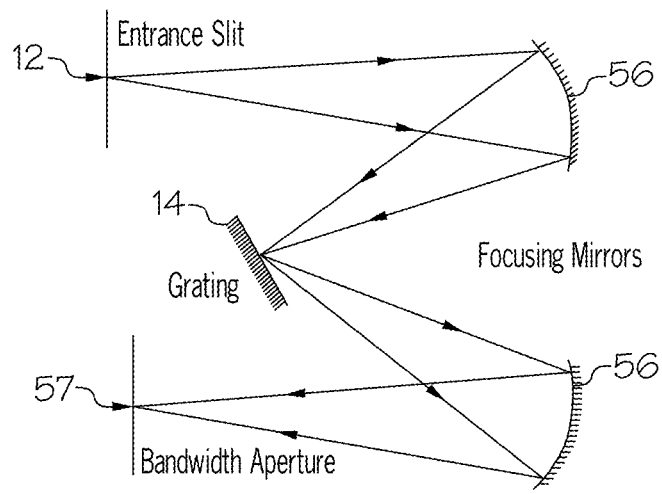
FIG. 20 provide a tunable UV type detector scheme.

Tunable UV detectors use a rotating planar grating and a bandwidth aperture to select wavelengths of light for detection. As shown in FIG. 20, light passes through an entrance slit 12 onto a mirror 56 which focuses the light onto the grating 14. The light is diffracted from the grating 14 and bounces off a second mirror 56 which focuses the light through a bandwidth aperture onto the flow cell 66. Detectors 4 of this type tend to have a fixed bandwidth of 5 to 10 nm. In a tunable UV detector 4, only one small section of the spectrum is sent through the sample at a time. This greatly reduces the possibility of noise from multiphoton interaction events. It allows the complete light signal to be referenced immediately before passing through the sample which can noticeably increase the signal to noise ratio.

Figure 21:
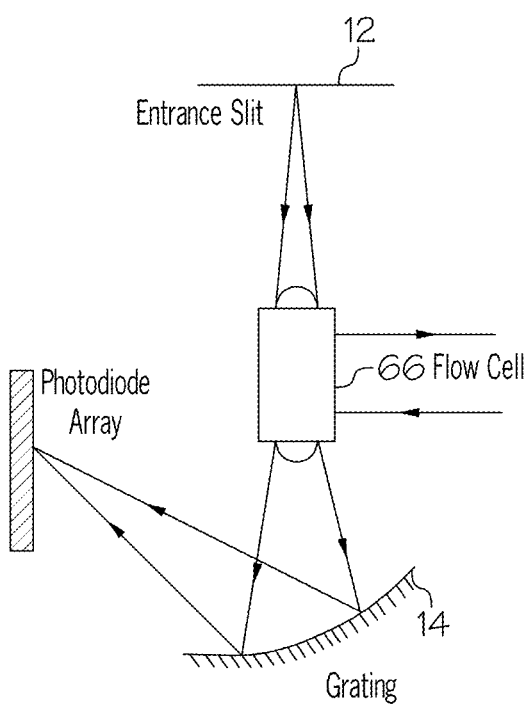
FIG. 21 provides a photodiode array type detector scheme.

Because these detectors use motors to rotate their gratings, they are not able to dynamically switch between wavelengths in any meaningful way. Fixed width apertures also do not permit any flexibility in the bandwidth sent through the flow cell. On the other hand, photodiode array detectors 4 direct the light from the light source 50 straight to the flow cell 66, sending through the entire spectrum. After the light exits the flow cell 66 it is directed through a narrow exit slit 68 onto a concave grating 214. The grating 14 diffracts and focuses the light onto an array consisting of at least several hundred photodiodes. See FIG. 21.

Photodiode array detectors collect absorption data for the entire spectrum at one time. Obtaining the overall spectral response of a sample can be a powerful analytical method, especially compared to gathering information about only a single wavelength for each sample run. These detectors still reference the optical signal, however, since the reference pulls from the entire spectrum at once it cannot eliminate as much noise as the reference in a tunable UV detector can. Multiphoton absorption is a second order effect, nevertheless it has been observed in liquid chromatography detectors. Vickrey, T. M., *Liquid Chromatography Detectors*, Vol. 23. CRC Press, 1983. By sending through the entire spectrum at once we lose the ability to de-convolve multiphoton absorption and any other higher order interaction effects from the conventional absorption signal.

EXAMPLE I

UVC LED Detector Optical Pathway

Provided herein is a strategy for an optical pathway for a LED detector that allows dynamic manipulation of both the bandwidth and the specific wavelengths passed through the sample during detection. Using this strategy, light from one or more LED 6 may be coupled to one or more optical fibers, which terminate at the entrance slit to the optics bench. Light entering the slit will be incident upon a spherical grating, which will diffract the light across the breadth of a digital micro-mirror device. Once the light is spread across the DMD 8 in this fashion, selecting the optical bandwidth and center wavelength becomes a matter of tilting those columns of mirrors to the on position. As described and shown in FIG. 4, from the DMD 8, the selected light will be reflected by a focusing mirror through a beam splitter and the flow cell 66 to arrive at the reference and sample photodiodes.

Figure 22:
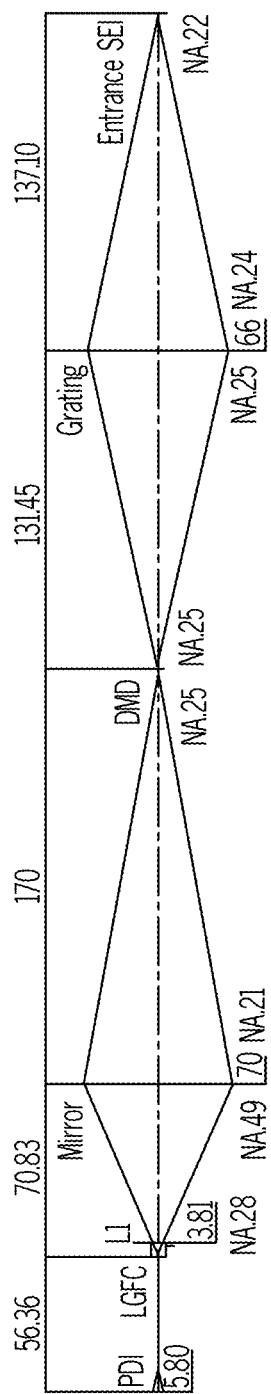
FIG. 22 provides an unfolded optical pathway for alternative scheme.
Figure 23:
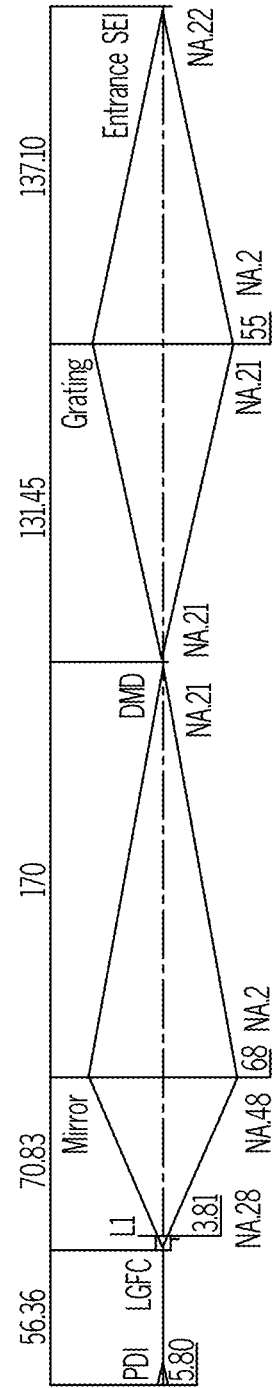
FIG. 23 provides an unfolded optical pathway with aperture stops.

In FIG. 22, the unfolded optical pathway, orthogonal directions, and NA labeled are shown. Once the various components have been defined and optically located, they can be packaged to permit a compact footprint for implementation in a consumer version of the detector. An updated optical pathway including aperture stops which correctly couple the elements is shown in FIG. 23.

Having the optical pathway defined, the elements can be arranged in their folded configuration, which is a packaging for the optics that provides a compact footprint for full implementation in a consumer version of the detector.

EXAMPLE II

Optical Layout for Optic Bench Assembly

Figure 24A:
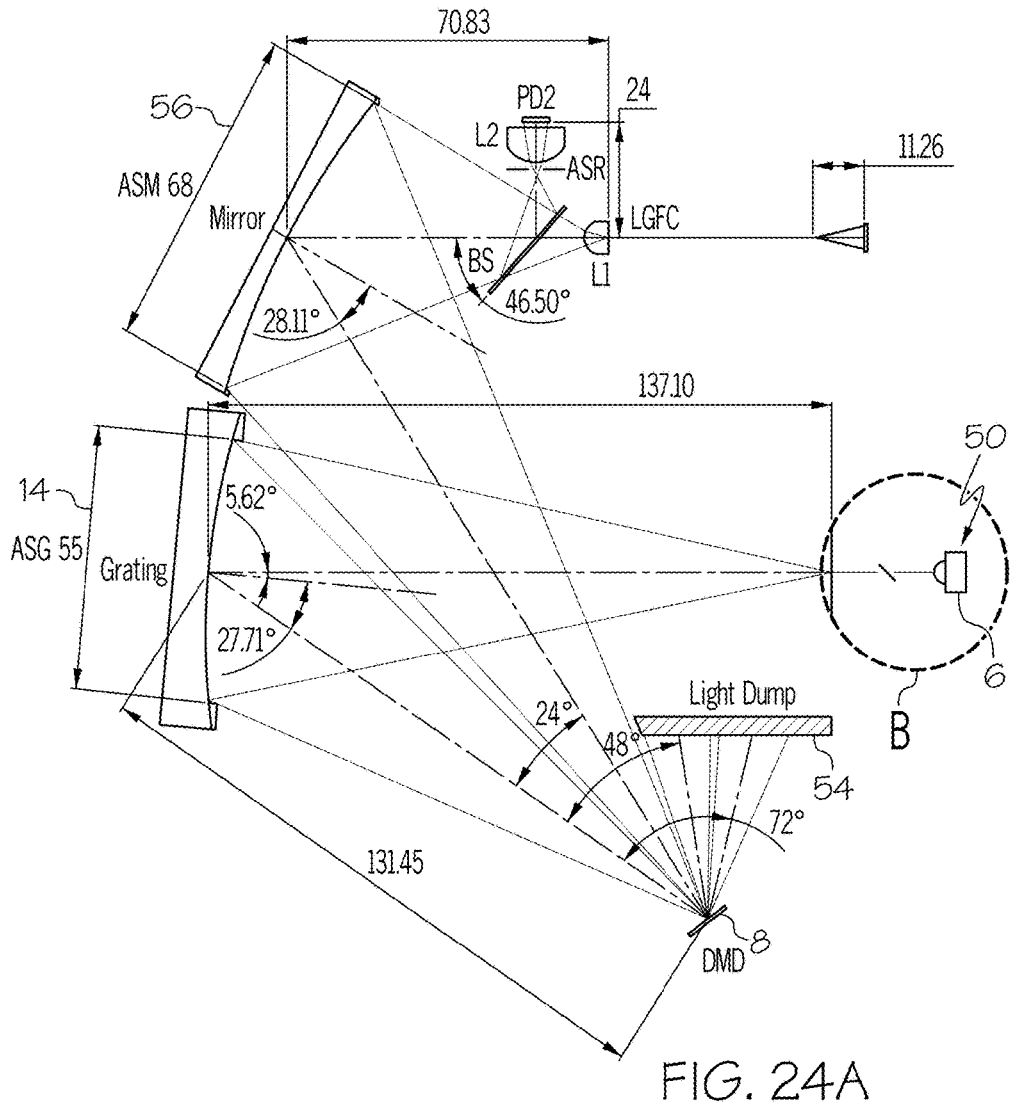
Figure 24B:
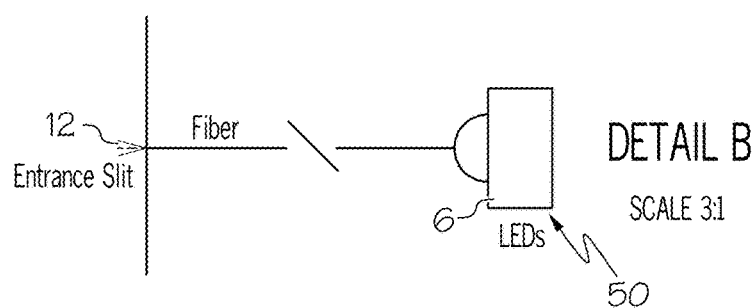

An embodiment of an optical layout for the optic bench assembly 40 is shown in FIGS. 24A, 24B and 24C.

An embodiment of an optical layout for the optic bench assembly 40 is shown in FIG. 24. To build the detector 4, Table 2 provides specifications for commercially available components which could be used. The list is not exhaustive, but contains the specifications relevant to calculating the expected performance of such a detector and is provided primarily for this purpose. Two notable exceptions found in Table 2 are the AlN LEDs with peak emissions below 250 nm and the UVC reflecting DMD. Neither of these are commercially available at the time we are writing, however, each has been demonstrated in the laboratory and can reasonably expected to be commercially available in the near future. Taniyasu, Y. et al., *An Aluminum Nitride Light-Emitting Diode With a Wavelength of 210 Nanometres*, Nature, vol. 441, no. 7091, 2006; Fong, J. T. et al., Advances in DMD-Based UV Application Reliability Below 320 nm, Proc. SPIE, vol. 7637, 2010; Thompson, J. et al., *Digital Projection of UV Light for Direct Imaging Applications, DLP® Technology is Enabling the Next Generation of Maskless Lithography*, 2008.

TABLE 2

| Component Specifications | |
|---|---|
| LEDs: | DMD: |
| Peak wavelengths 220, 230, . . . . . , 320 nm | Pattern rate~10 kHz |
| Optic power output ≥ 1 mW each | Width of active array ≥ 7 mm |
| Thermal output~1 W | Micromirror pitch 5.4 μm |
| FWHM 12 nm | Overall efficiency at least 60% |
| Rise-time < 1 ms | Tilt 12° orthogonal to package |
| Packaging < 10 mm ⌀ | Window material quartz glass |
| Lifetime ≥ 2000 hours | |
| Spherical Grating: | Photodiodes: |
| Focal length~140 mm | Spectral response at least 200 nm to 350 nm |
| Linear dispersion~25 nm/mm | Length~6 mm |
| Blaze λ 250 nm | Rise time less than 5 μs |
| Wavelength range 200 nm-350 nm | Photosensitivity~0.11 A/W |
| Efficiency at least 40% across entire range | Dark current less than 50 pA |
| | Window material quartz glass |
| Fibers: | Flowcell: |
| Core ⌀ 100 μm | Light-guided |
| Material fused silica | Length of flow 10 mm |
| NA 0.22 | Overall length~50 mm |
| | NA .28 |
| Entrance Slit: | Analog to Digital Converters: |
| Width 40 nm | Sampling Rate ≥ 1 MHz |
| Height 2 mm | Bits ≥ 20 |

Calculations supporting expected specifications for the UVC LED detector 4 together with a comparison to commercially available detectors of the tunable UV and photodiode array variety are provided immediately below.

Bandwidth

The minimal possible bandwidth for the detector 4 depicted in FIGS. 24A, 24B and 24C is the entrance slit 12 width multiplied by the linear dispersion of the spherical grating 14, depending on concave grating magnification. For the entrance slit 12 of 40 μm and a linear dispersion of 25 nm/mm the minimal bandwidth is 1 nm. By tilting more columns (12) of the DMD 8 to the on position this bandwidth can be increased in steps of 0.135 nm, which is set by the micro-mirror pitch of 5.4 μm.

Optical Throughput

The optical power incident on the sample photodiode can be calculated by multiplying the cumulative irradiance of the LED sources, Io, by the bandwidth, Δλ, and by the net efficiency of each optical element as shown in Equation 16 for n elements. The net efficiency is the product of the reflectance or transmission efficiency of an element η and the fill factor for an element F, which is the ratio of the numerical apertures squared.

$$\phi_{photodiode} = (I_o \Delta \lambda) \Pi_{i=1}^n \eta_i F_i \qquad (16)$$

Table 3 shows the approximate values of 11 and F for each element in the light path. F is listed as 1 for all fill factors greater than unity. Total coupling efficiency from the LED to the fiber is assumed to be 20 percent, which should be possible given use of a refractive-reflective lens as mentioned herein, and is shown distributed between the fill factor for the LED lens and the fiber.

TABLE 3

Reflection, Transmission, and Coupling Efficiencies of Optics

| Element | H | F | $\eta_{net}$ |
|---|---|---|---|
| LED lens | 0.9 | 0.45 | 0.41 |
| Fiber | 0.95 | 0.45 | 0.43 |
| Entrance Slit | n/a | 0.5 | 0.5 |
| Grating | 0.55 | 0.8 | 0.45 |
| DMD | 0.6 | 1 | 0.6 |
| Mirror | 0.9 | 1 | 0.9 |
| Sample Path | | | |
| BS | 0.9 | 1 | 0.9 |
| L1 | 0.98 | 1 | 0.98 |
| LGFC | 0.8 | 0.7 | 0.56 |
| PD1 | n/a | 1 | 1 |
| Entire Sample Path | | | 0.011 |
| Reference Path | | | |
| BS | 0.1 | 1 | 0.1 |
| L2 | 0.98 | 1 | 0.98 |
| PD2 | n/a | 1 | 1 |
| Entire Reference Path | | | 0.002 |

By solving Equation 16 using the values given in Table 3, we can find the flux incident on the sample and reference photodiodes 62, 64. Using the photosensitivity specification for the photodiodes we can then find the signal and reference current. A summary of the outcome for several cases can be found in Table 4 below.

TABLE 4

Sample and Reference Photodiode Responses for Various Scenarios

| Source and Bandwidth | $\Delta\lambda$ nm | $I_o$ (mW/nm) | $\Phi_r$ mW | $\Phi_r$ mW | $I_s$ mA | $I_r$ mA |
|---|---|---|---|---|---|---|
| Single LED, 1 nm | 1 nm | 0.08 | $8.8 \times 10^{-4}$ | $1.6 \times 10^{-4}$ | $8.8 \times 10^{-5}$ | $1.6 \times 10^{-5}$ |
| Single LED, 5 nm | 5 nm | 0.08 | $4.4 \times 10^{-3}$ | $8.0 \times 10^{-4}$ | $4.4 \times 10^{-4}$ | $8.0 \times 10^{-5}$ |
| Array, 1 nm | 1 nm | 0.11 | $1.2 \times 10^{-3}$ | $2.2 \times 10^{-4}$ | $1.2 \times 10^{-4}$ | $2.2 \times 10^{-5}$ |
| Array, 5 nm | 5 nm | 0.11 | $6.1 \times 10^{-3}$ | $1.1 \times 10^{-3}$ | $6.1 \times 10^{-4}$ | $1.1 \times 10^{-4}$ |

Signal to Noise Ratio

Using the currents from Table 4 and Equation 15 for the shot noise dominated signal to noise ratio, we can calculate the limiting SNR values for the same set of conditions. The result of these calculations can be found in Table 5 immediately below.

TABLE 5

SNR and Noise Levels for Various Scenarios

| Source and Bandwidth | SNR 80 Hz Sampling Rate | Noise Level |
|---|---|---|
| Single LED, 1 nm | 58,600 | $\pm 1.7 \times 10^{-5}$ AU |
| Single LED, 5 nm | 131,000 | $\pm 7.6 \times 10^{-6}$ AU |
| Array of LEDs, 1 nm | 68,500 | $\pm 1.5 \times 10^{-5}$ AU |
| Array of LEDs, 5 nm | 154,000 | $\pm 6.5 \times 10^{-6}$ AU |

Sampling Rate

The detector would use a sampling rate of 80 Hz to display the chromatographs, mimicking current methodology and keeping the shot noise down. However, the electro-optical components in the detector are themselves capable of operating at much higher frequencies. As demonstrated in Table 6 the DMD can be the limiting factor for the system.

TABLE 6

Max Operating Frequencies for Dynamic Elements

| Element | Relevant Spec. | Value | Max Frequency |
|---|---|---|---|
| LED | Rise time | <2 µs (dominated by driving electronics) | 1 MHz |
| DMD | Pattern rate | 9.5 kHz | 9.5 kHz |
| Photodiode | Rise time | ~2 µs | 0.5 MHz |
| ADC | Sample rate | 1 MHz | 1 MHz |

If the DMD 8 is considered to timeshare among multiple wavelengths, it is apparent that 9.5 kHz will support continuous sampling of 118 channels at 80 Hz. Since the instrument has a minimum bandwidth of 1 nm and a range of 110 nm, this feature can allow full sampling at every wavelength simultaneously, mimicking the functionality of a photodiode array detector while maintaining the benefits of the referencing strategy it shares with tunable UV detectors. Even at full sampling over the entire range, the DMD 8 has seven percent excess capacity which can be used for automatic wavelength and dark current calibrations in the loop while sampling.

After the capabilities of the DMD 8 have been fully utilized the rest of the components have at least 50 times the ~10 kHz rate available. This excess capacity can be used to sample each pattern created by the DMD 8 multiple times and use averaging to filter out noise. Shot noise increases proportionally to the square root of the sampling rate, and averaging decreases noise by the square root of the number of samples, so the shot noise will not be improved. However, other sources of noise present in the signal can effectively be filtered out by this method.

An electronic sampling rate of 1 MHz could accurately characterize the instrument dynamics. Such information could be used to optimize machine specific operation and troubleshoot, resulting in increased performance and reliability for the end user.

Expected Resolution

In an embodiment, each column 22 of micro-mirrors on the DMD 8 corresponds to a 0.135 nm step in the wavelength. The width of the entrance slit 12 prevents a bandwidth of this size, however. This step size in resolution is in fact the theoretical lower bound for the instrument. In reality, several factors will increase this number to an empirically realizable resolution. Resolution Sensitivity In order to accurately estimate the resolution of the detector 4 we will have to characterize its sensitivity to several variables: (1) distance between the entrance slit 12 and the spherical grating 14; (2) distance between the spherical grating 14 and the DMD 8; (3) width of the entrance slit 12; and (4) angular misalignment between the DMD 8 and the spectral plane of the grating 14. All of these can be determined to first order purely by the geometry of the light path.

If we take $L_\alpha$ to be the position of the entrance slit relative to the grating then we can find the relation between changes in $L_\alpha$ and changes in resolution as shown in Equation 17 where R is resolution and dl is the linear dispersion of the grating.

$$\frac{dR}{dL_\alpha} = 2|dL_\alpha|NAd_l \qquad (17)$$

The same relation holds for the position of the DMD relative to the grating, $L_H$. We already know the relationship between the entrance slit width and the resolution and they are directly proportional to each other where $d_l$ is the constant. Finally, we can define the relationship between angular misalignments, $d\theta_{DMD}$, and resolution. Using the small angle approximation, we find the expression shown in Equation 18 where $L_{DMD}$ is the length of the digital micromirror array.

$$\frac{dR}{d\theta_{DMD}} = d\theta_{DMD}(L_{DMD}NAd_l) \qquad (18)$$

Putting all of these together we can find an expression for the sensitivity of resolution to all of these factors, given in Equation 19.

$$\frac{\partial R}{\partial L_\alpha \partial L_H \partial w_{slit} \partial \theta_{DMD}} = \qquad (19)$$
$$2NAd_l(|\partial L_\alpha| + |\partial L_H|) + \partial w_{slit}d_l + \partial \theta_{DMD}(L_{DMD}NAd_l)$$

This expression for sensitivity can serve as a basis for error budgeting during mechanical design to ensure that the actual resolution of detectors with this optics bench meet their target specifications.

Comparison to Existing UV Detectors for Liquid Chromatography

Table 7 provides a comparison of the specifications of the detector 4 provided herein with several commercially available detectors.

TABLE 7

Comparison of UVC LED Detector Capabilities With Tunable UV and Photodiode Array Detectors

| Specifications | TUV | PDA | UVC LED |
| --- | --- | --- | --- |
| Wavelength Range | 190-700 nm | 190-700 nm | Variable within 210-320 nm |
| Sampling Speed | 80 Hz | 80 Hz | Variable from 80 Hz-9.5 kHz |
| Noise level | $2 \times 10^{-5}$ to $6 \times 10^{-6}$ | $3 \times 10^{-6}$ | $6.5 \times 10^{-6}$ (shot noise, no filter) |
| Bandwidth | 5 to 6.5 nm | 1.2 nm to 4 nm | Variable from 1-110 nm |

TABLE 7-continued

Comparison of UVC LED Detector Capabilities With Tunable UV and Photodiode Array Detectors

| Specifications | TUV | PDA | UVC LED |
| --- | --- | --- | --- |
| Resolution/Accuracy | ±1 nm | ±1 nm | ±0.2 nm |
| Irradiance of source | 0.1 µW $nm^{-1} cm^{-2}$ | 0.1 µW $nm^{-1} cm^{-2}$ | Variable up to 1.5 µW $nm^{-1} cm^{-2}$ |
| Self-referencing | Yes | No | Yes |
| Self-Calibration | 5 min. at warmup | 5 min. at warmup | 0.05 s (any time) |
| Start-up time | 20 min. | 20 min. | <1 min. |

AlN based LEDs have many advantages over traditional UV light sources such as increased lifetime, higher intensity per unit bandwidth, low heat generation, and can be rapidly modulated. The DMD 8 permits time sharing over multiple wavelengths, variable bandwidth and the potential for multiple types of auto-calibration.

EXAMPLE III

Prophetic Optical Detector

In an embodiment, the detector 4 includes a plurality of LEDs (also referred to sometimes as a "bank") as the light source 50. The LED has an aluminum nitride (AlN) substrate to emit light in a low UV range in wavelengths comparable to that of the deuterium UV lamp. To cover a broader range of wavelength, the detector 4 can have up to multiple LED 6 (i.e., up to a dozen) to generate any combination of peak wavelengths between 210 nm and 320 nm. Both presence and concentration of a particular substance (referred to herein as a "constituent" or "compound") in a sample can be determined by recording the amount of UV radiation absorbed at one or more particular wavelengths. Light from the LED 6 and an onboard mercury arc calibration lamp (not shown) can be transmitted to the entrance slit 12 using fused silica fiber optics (not shown).

In an embodiment, the entrance slit 12 has a single aperture, 1 mm long and 40 microns wide, to project light onto a spherical holographic grating. The grating will diffract the light according to its wavelength and will focus a light beam 58 onto a Digital Micro-mirror Device ("DMD") 8. The DMD 8 can select a single wavelength or a range of wavelengths and reflect the light beam 58 towards a spherical mirror 56. Wavelengths not selected can be directed onto a light dump 54. The light incident on the spherical mirror 56 can be reflected toward the beam splitter 60, which, in turn, will direct a small portion of the light toward reference photodiode 62. Remaining light will be directed to the main photodiode 64 through the flow cell 66. The reference photodiode 62 can enhance the signal to noise ratio ("SNR") of the processed data by directly cancelling out different forms of noise. The detector 4 can be versatile, with similar (or improved) capabilities as the TUV or the PDA. Proposed specifications of the UV-LED detector are shown in Table 8 immediately below:

TABLE 8

Specifications of UV-LED Detector

| Specifications | UV-LED DETECTOR |
| --- | --- |
| Wavelength Range | Variable within 210-320 nm |
| Sampling Speed | Variable from 80 Hz-9.5 kHz |
| Noise level | $6.5 \times 10^{-6}$ (shot noise, no filter) |
| Bandwidth | Variable from 1-110 nm |

TABLE 8-continued

Specifications of UV-LED Detector

| Specifications | UV-LED DETECTOR |
|---|---|
| Reolution/Accuracy | ±0.2 nm |
| Irradiance of source | Variable up to 1.5 µW nm$^{-1}$ cm$^{-2}$ |
| Self-referencing | Yes |
| Self-Calibration | 0.05 s any time during run |
| Start-up time | <1 min |

EXAMPLE IV

Design Considerations for an Optics Bench Assembly

Material Selection

Attributes of a specific material for the optics bench assembly 40 can include a set of physical, mechanical and chemical properties that characterizes the material as required for an intended service. The Ashby Material Selection method of material selection has four steps: (1) translation of design requirements to quantitative and qualitative terms such as function, constraints, objectives and free variables; (2) initial screening of materials based on derived attribute limits from constraints; (3) ranking the screened material based on material index, which is a criterion of excellence that maximizes or minimizes the objective; and (4) final screening of materials based on supporting information such as availability, cost, behavior in working environments for top ranked material. See, Ashby, M. F., *Materials Selection in Mechanical Design*, Third Edition, 3rd ed. 2005.

Translation

Any engineering component has a multitude of functions such as; supporting a load, conducting heat, containing pressure, etc. These functions can be achieved while subjected to certain constraints laid down by the design such as maximum dimensions, thickness, maximum load capacity, etc. During the design process, the designer is looking to achieve his or her design objectives (such as making the part lighter or cheaper) and to achieve these objectives, he or she is free to manipulate the variables which are not constrained by design requirements. These are called the free variables. Therefore, the first step of material selection is to reinterpret the design requirements in terms of the function, constraint, objectives and free variables.

Screening

Initial screening eliminates the materials which do not meet the basic requirements set by the constraints. These constraints are known as the attribute limits. Screening is done with the help of material selection charts which plot a combination of properties of interest, (for instance Young's modulus versus density or strength versus density) and by mapping out the fields in property-space occupied by each material class, and the sub-fields occupied by individual materials. Attribute limits are plotted on material selection charts as horizontal or vertical lines. The material lying in the optimal region defined by the attribute limits matches the design requirements and has potential to be used in the final product/design.

Ranking

In order to rank the screened candidates, optimization criteria known as Material Indices is derived which measures how well a material matches the design requirements. It is a property or a group of properties that defines performance and therefore maximizing material index will maximize the performance for a given design.

Supporting Information

After ranking and short listing the top candidates which satisfies all design constraints and meets the objective requirements, other details are necessary for selecting the final best materials for the design. The details required are corrosion behavior in a particular environment, information on availability and pricing, aspects of past history of the material and established uses, in-house expertise or availability of machine tools for manufacturing, etc.

Manufacturing Process Selection

Similar to the material selection process, the manufacturing process is selected by translating the design requirements into function, constraints, objectives and free variables. Function defines what the final finished product is intended to do. Constraints can be set based on design requirements such as material, shape, mass, section thickness, tolerance requirements and annual production volume. Objectives define which parameter of the manufacturing process (cost, quality, time, etc.) needs to be maximized or minimized. Free variables are usually the choice of manufacturing process or chain of manufacturing processes that can meet the objectives while also satisfying the constraints. While performing the initial screening, processes which do not meet the basic design requirements are eliminated. Selection charts such as process-material matrix, process-shape matrix, property bar chart are used to select the appropriate manufacturing process. Additional information such as accessibility and infrastructure availability for a particular manufacturing process are also considered while selecting the best suited manufacturing process.

EXAMPLE V

Optics Bench Assembly Construction and Serviceability

In the optics bench assembly 40, parts required for proper functioning of the product can include parts that are easy to align and assemble. Components can be such, that there is little or no resistance to insertion. Chamfers can be provided to guide the insertion of two mating parts. Preferably, clearance can be generously provided and care taken to avoid clearances that will result in a tendency for parts to jam or hang-up during insertion. Common parts, processes, and methods can be standardized across all models and even across product lines to permit the use of higher volume processes that normally result in lower product cost. A part can be designed such that it is located before being released.

A potential source of problem arises when a part is released at the place of its assembly before it is positively located. Under these circumstances, reliance is placed on the trajectory of the part being sufficiently repeatable to locate it consistently. Wherever possible, the necessity of holding parts down during manipulation of the subassembly or during the placement of another part should be avoided. For manual assembly, both access and vision is preferably not restricted. For automated assembly, insertion in a straight line from above is preferred.

To avoid, problems and issues related to manufacturability, reliability, serviceability in the optics bench assembly 40, consideration of issues or problems with earlier models can prevent repeating the same mistakes. Anderson, D. M., *Design for Manufacturability: How to Use Concurrent Engineering to Rapidly Develop Low-Cost, High-Quality Products for Lean Production*, CRC Press, 2014. The assembly sequence can be concurrently engineered while designing the product. Designing for easy parts fabrication, material processing, and product assembly is a primary design consideration. Even if labor cost is reported to be a small percentage of the selling price, problems in fabrication, processing, and assembly can generate enormous overhead costs, cause production delays, and demand the time of precious resources.

Over-constraining an assembly leads to high tolerance demands. It also induces stress in the assembly. Over-constraints are also costly, causing quality problems and compromising functionality because the design will work only if parts are manufactured with extremely tight tolerances. On the other hand, under-constraining can have one or more unfixed degrees of freedom and thus results in loosely assembled parts. Avoidance of over-constraining or under-containing the assembly is recommended. Whitney, D. E., *Mechanical Assemblies: Their Design, Manufacture, and Role in Product Development, Volume* 1, Oxford University Press, 2004.

Components and assembly parts of the optics bench assembly 40 can be designed such that there is an unobstructed path for entry into this device, preventing damage to the component, part or optics bench assembly 40. Also, there can be unobstructed access for tools and the tool operator, whether that is a worker or robot arm, for assembly and repair. Awkward contortions in assembling a product manually can lead to worker fatigue, slow throughput, poor product quality, and even worker injury. Anderson, D. M., *Design for Manufacturability: How to Use Concurrent Engineering to Rapidly Develop Low-Cost, High-Quality Products for Lean Production*, CRC Press, 2014. Preferably, individual components and/or sub-assemblies are independently replaceable, giving the advantage of easily replacing parts without having to remove other parts first. The order of assembly can then be more flexible because parts can be added in any order. Another advantage of independently replaceable parts is the ease of adding options later, either in the factory or in the field. In terms of supply chain, this helps to cope with part shortages, allowing the rest of the product to be built and when components or parts are not available.

Having considerations toward sequence of assembly, the component with lowest mean time to failure is preferably assembled at the end (particularly for assemblies for which the components are not independently replaceable) and the easiest to remove from the assembly so that it can be easily replaced without much hassle. In an embodiment, future upgrades and other part options can be easily assembled into the product without a complete redesign. This increases overall product life by adding future upgrades and helps generates more profit even in late stages of the product lifecycle. Considerations towards future upgrades include allowing space for added parts, mounting holes, part access, tool access, software reconfiguration, extra utility capacity, etc.

The product architecture can be structured into modules and sub-assemblies, as appropriate. Sub-assemblies can be built in specialized departments and tested separately from the overall product. This streamlines the manufacturing and assembly process. Also sub-assemblies simplify product testing, as individual sub-assemblies can be pre-tested and/or do not require extensive re-testing during final assembly. It is also easier to identify failure modes and quality problems in a product with subassemblies. Then, diagnostic attention can be focused to the sub-assemblies with highest likely probability of failures. Sub-assemblies can also improve serviceability as the defective subassembly or parts can be easily repaired or replaced with new ones. A modular design allows for replacement of obsolete modules with upgraded ones, increasing the product life and performance.

Finally, assembly using liquid adhesives and sealants should be avoided. Long drying times with adhesives and sealants can compromise flow manufacturing. Instead, alternatives such as screws or nuts coated with retention compound, fasteners with deformed threads, lock washers, compliant gaskets or even effective design strategy such optimal enclosures and built-in seals can be considered.

Thermal Management

Thermal distortion of components due to thermal gradients or due to change in temperature over time, is a common cause of non-repeatability and dimensional instability in components. This negatively affects the functionality of the product due to thermally induced errors. Some of the guidelines to increase the thermal stability are immediately discussed below. Hale, L. C., *Principles and Techniques for Designing Precision Machines*, MIT, 1999.

Sensitivity Reduction

Components of the optics bench assembly 40 can be assembled in such a way that symmetric temperature distributions are achieved in symmetric structures which in turn reduces thermal distortions. Materials with a low coefficient of thermal expansion can be used to reduce variations in geometry due to variations in temperature. Components with the most critical temperature sensitivity can be located near the air inlet to provide the coolest air flow.

Management of Heat Sources

Sources of heat are placed outside the controlled environment and unnecessary heat sources can be eliminated where possible. Hot spots can be avoided by spot cooling using a small fan. Components that dissipate less heat are preferred over high heat dissipating components. Sources of heat can be isolated from other sensitive components and the flow of heat removing fluids over other sensitive parts of the system can be prevented. The isolation of components with high heat dissipation can be achieved by placing those components near the enclosure air exits. Heat sources with the controlled environment can remain constant and the amount of heat dissipation cannot vary over time.

Control of the Machine Environment

The room/lab air temperature can be controlled to reduce temperature variations in the optics bench assembly. Heat leakage into or out of the room/lab can be prevented to reduce variations in the room air temperature. The structure of the optics bench assembly 40 can be isolated and the temperature of the metrology loop can be controlled. A temperature controlled fluid flowing over the subassembly/component can be used to regulate its temperature. The effect of viscous heating in high speed fluid flows can also be considered. Indeed, the human body represents a heat source of about 100 watts. Thus use of insulating clothing such as gloves for precision applications is recommended. Dust can be kept out of the optics bench assembly 40 enclosure by pressurizing it or blowing air. The largest possible filter can be used in order to increase dust capacity and reduce pressure drop. Temperature control is the most reliable, effective and least expensive means to reduce thermal errors. The design challenge is how to provide sufficient control for minimal cost.

Shock Isolation

Mechanical shock is a sudden and severe non-periodic disturbance of a mechanical system which causes significant forces that may damage the system. Shock loads when applied to a portion or entire optics bench assembly 40 may result in elastic or inelastic deformation of optical enclosure, impairment of optical alignment, and/or failure of fragile optical components. Such conditions are usually encountered during shipping, when for example the transportation truck encounters pothole or bump, or when someone accidentally drops the optics bench assembly 40 while moving it. Some of the major causes of shock in a system include: (1) sudden change in the level of energy in the system by sudden introduction of energy; (2) application of a sudden force; and (3) abrupt change in motion, velocity or acceleration of the system The short duration transient loads called the shock pulse have complex wave shapes. To simplify the analysis the complex wave shapes can be approximated to a nearest simple wave shape with a known response. The input shock pulses are characterized by maximum amplitude, time duration and approximate shape.

The majority of shock pulses encountered by objects can be categorized as half sine shock pulse, versed-sine shock pulse, rectangular shock pulse, triangular shock pulse, drop/freefall shock, velocity shock, acceleration impulse and force impulse. Shock resistance is defined by its fragility, which in turn is expressed as the highest level of acceleration beyond which the equipment will fail to operate within specification. Shock mounts are used to absorb the input acceleration and release the shock energy over a broader time base, thus reducing the output acceleration. The shock mount shall not permit the output acceleration to exceed the fragility level of the most delicate component in an assembly. The optics bench assembly 40 specifications generally define fragility in terms of acceleration in multiples of gravity. The shock level associated with normal manual handling of the optical instruments is around 3Gs. Yoder, P., *Opto-Mechanical Systems Design, Fourth Edition, Volume 1: Design and Analysis of Opto-Mechanical Assemblies*, Volume 1, CRC Press, 2015.

Vibration Isolation

Every structure has the tendency to vibrate at certain frequencies, which are known as natural or resonant frequencies. The natural frequency of a piece of equipment is given by Equation 1, where k is the stiffness and m is the mass of the equipment.

$$f_n = \frac{1}{2\pi} \sqrt{\frac{k}{m}} \quad (20)$$

Each natural frequency is associated with a certain shape, called mode shape, which the model tends to assume when vibrating at that frequency. Resonance is a condition in which a structure or component is excited by a dynamic load at one of its natural frequencies leading to large displacements and stresses in the component. For un-damped systems, resonance theoretically causes infinite motion. Damping, however, puts a limit on the response of the structures due to resonant loads.

The efficiency of flow of vibrational energy is quantified by transmissibility, which is defined as the ratio of dynamic output to dynamic input. In other words, transmissibility quantifies how efficiently a forcing vibration can produce an excited vibration. Vibration isolation is attained by maintaining a proper relationship between the disturbing frequency and the system's natural frequency. Transmissibility measures the effectiveness of isolators in reducing vibration.

Figure 25:
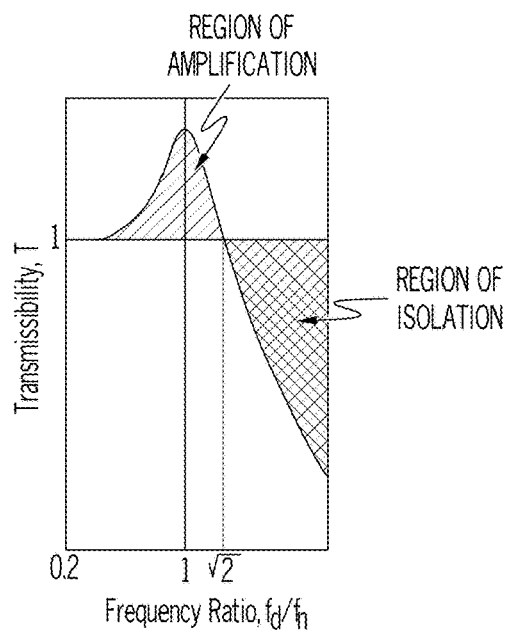
FIG. 25 shows transmissibility versus frequency ration curve.

FIG. 25 shows transmissibility plotted against the ratio of disturbing frequency and the natural frequency of a system. In FIG. 25, the plot shows the disturbing frequency is low compared to the natural frequency of the system the transmissibility is close to 1. When the disturbing frequency approaches the natural frequency, transmissibility is high. This implies that the output is higher than the input. When the ratio of the disturbing frequency and natural frequency is greater than √2, transmissibility is less than 1 and the system is isolated because the output is lower than the input. Elastomeric springs are commonly used for vibration isolation. Most of the vibration isolators also possess damping but in varying degrees. Without damping a system would continue to vibrate at its resonant frequency for an extended period of time even if the excitation load is removed. With damping, the oscillations decay quickly as some of the excitation energy is converted into heat. The greater the amount of damping, lower is the transmissibility at resonance. Damping is advantageous when the system operates at or near the natural frequency as it reduces the peak response at resonance.

Design for Serviceability

Figure 26:
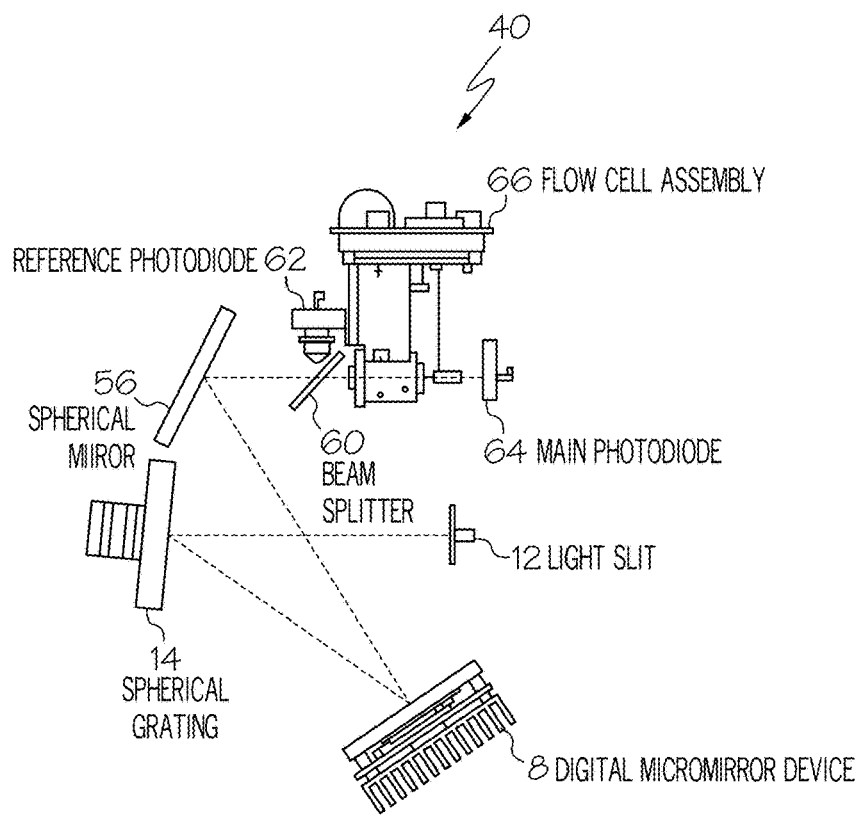
FIG. 26 shows an optical layout of an embodiment of the UV-LED detector.

As shown in FIG. 26, the optics bench assembly 40 can be designed so that the individual sub-assemblies are independently replaceable. There are multiple advantages with independent replaceable components and sub-assemblies. First, it allows sub-assemblies such as the grating assembly and mirror assembly to be calibrated and tested independently before being assembled to the optics bench. Second, serviceability of the optics bench assembly 40 is improved such that a nonfunctional part in the assembly can be removed for repairs or it can be replaced with a new part without removing any other components first. Third, components and parts can be added in any order without any specific assembly sequence. Another advantage of using independently replaceable sub-assemblies is that any compatible future upgrade of the individual parts can be seamlessly integrated with the current system, increasing the product lifecycle of the detector. Finally, the optics bench assembly 40 can be used for other detectors having a similar optical layout but different component part specifications.

EXAMPLE VI

The Optics Bench Assembly

As described herein, the optics bench assembly 40 comprises both optical components and structural components, together referred to sometimes as optics bench assembly 40 components or components. Optical components of the optics bench assembly 40 can include: (1) a light entrance slit 12; (2) a spherical grating 14; (3) a digital micro-mirror device (DMD) 8; (4) a spherical convex mirror 56; (5) a beam splitter 60; (6) a reference photodiode 62; (7) a main photodiode 64; and (8) a flow cell 66. Structural components of the optics bench assembly 40 described herein include: (1) a light dump 54 (sometimes referred to herein as a "light dump/shield" or a "light shield"); (2) an optics bench assembly casing 44; (3) an optics bench assembly cover 70; (4) a mirror, (5) a grating mounting mechanism 71; (6) a plurality of mounting brackets 72; and (7) a plurality of fasteners 73.

In the optics bench assembly 40, optical components can be located to eliminate relative motion between any two components mounted on the bench. Each component is compatible with light of wavelength ranging from 150 nm to 1000 nm (UV to IR). The optics bench assembly 40 can include the light dump 54 to absorb or otherwise suppressing any stray light or act as a light beam dump. Further, in an embodiment described herein, each of the optical components are isolated from vibrations, shock, external heat sources, environmental temperature variation, dust and airborne contaminants, humidity, and corrosion due to solvents and chemicals, and abrasion/erosion. In an embodiment of the optics bench assembly 40, heat that is generated in the components can be conducted away. As described herein, the optics bench assembly 40 can be manufactured and assembled to allow for ease of calibration and serviceability. In an embodiment, an effective service life cycle can be over 15 years.

Figure 27:
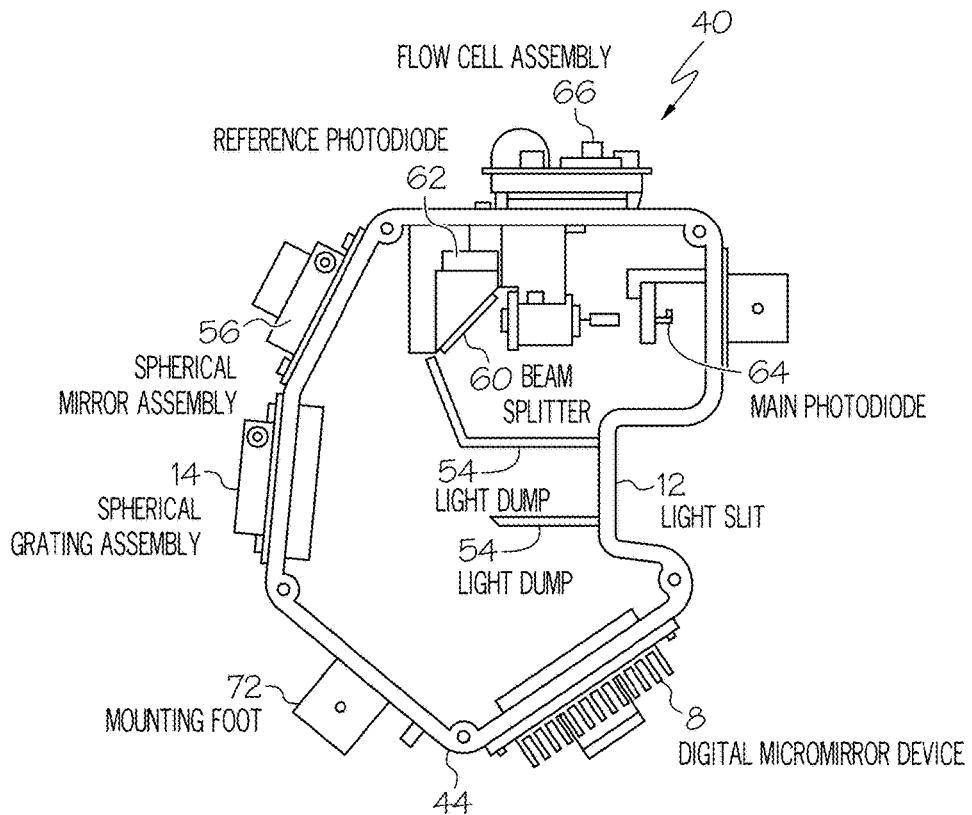
FIG. 27 show an embodiment of the optics bench assembly.

In an embodiment, the geometric shape of the optics bench assembly 40 is determined by the relative position and spatial arrangement of the optical components, which are determined via an optical layout of the UV-LED detector. FIG. 27 depicts an embodiment of an optical layout for the UV-LED detector. Besides the spatial arrangement of the optical components, manufacturability, assembly and serviceability are other factors that can determine the layout of the optics bench assembly 40. In addition, the overall height of the optics bench assembly 40 can be limited by the height of the detector 4 or detector module.

Figures 28A, 28B:
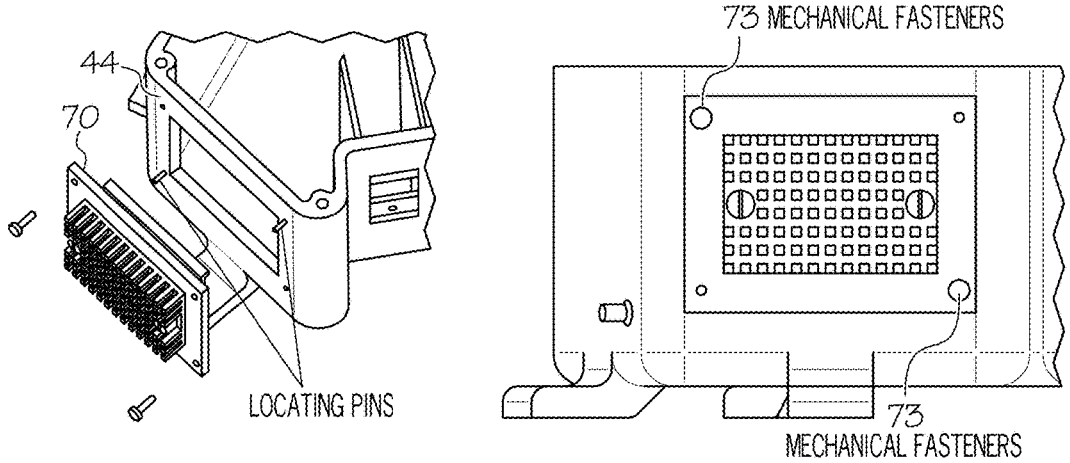
FIG. 28 shows an embodiment of the optics bench assembly where locating pins have chamfer at one end to guide the insertion of a part during assembly.

As shown in FIG. 28, the optics bench casing 44 is a rigid enclosure holding the optical elements together. The light dump 54 (that can absorb any stray light from light slit), the DMD 8 and the grating can also be part of the optics bench casing 44. Another feature is equally spaced mounting feet, or mounting brackets 72 in an optics bench casing 44. The mounting feet 72 attach the optics bench assembly 40 to the detector frame 74 and act as mounting points for shock and vibration isolators. The side walls 75 of the optics bench assembly 40 have one or more slots through which the optical components enter into the optics bench casing 44. The slots are sufficiently bigger than the maximum dimensions of the optical components to provide easy accessibility and to prevent any damage to optical components during assembly.

The optics bench assembly 40 can be structured into sub-assemblies. The sub-assemblies include spherical mirror assembly 56, grating 14, DMD 8, beam splitter 60 and reference photodiode 62, and flow cell 66. Division into subassemblies allows for individual calibration and testing of the mirror 56 and grating 14 before being assembled into the optics bench assembly 40. Subassemblies allow parts to be built in specialized departments or outsourced to a supplier with cheaper cost or better quality, without affecting other parts in the optics bench assembly 40. The selection of a suitable joining method of the subassemblies to the optics bench casing 44 is equally important. Permanent joining methods are inappropriate because some of the optical components such as DMD 8 and spherical grating 14 have smaller mean time to failure than other components and will need to be replaced after much shorter their intended service lives.

Therefore, a method of joining allows for assembly and disassembly of all the components. On the other hand, certain components can be rigidly held in place during operation and cannot be loosen due to slight vibrations. The relative positioning and orientation of optical components, for example, in an optical instrument or the detector is critical. Optical components can also be individually mounted and aligned in a precise fashion on the optics bench. Given all the above constraints, threaded fastener are preferred for assembly.

Figure 29A:
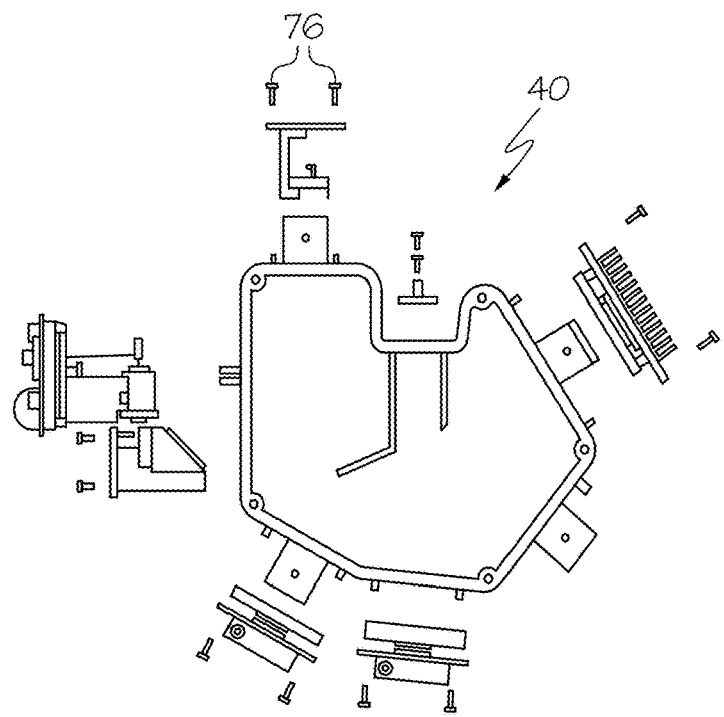
FIGS. 29A and 29B show an embodiment of the optics bench assembly.
Figure 29B:
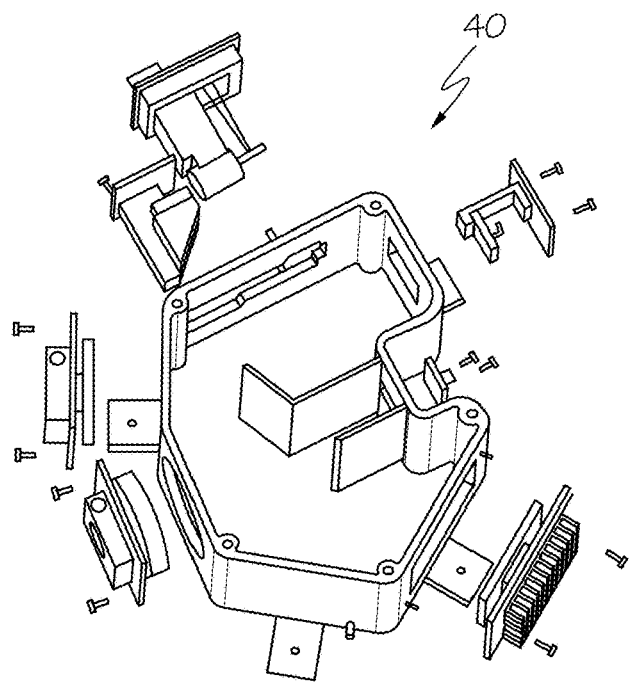

As shown in FIG. 29, each optical component can be located using two accurately machined locating pins 76 and held in place on the optics bench 42 with two fasteners. The components can be directly bolted to the optics bench casing 44 which has been precision machined. The locating pins 76 can be press-fit in machined holes on the optics bench assembly 40. Pins help to align and orient a component or part during assembly. Pins (not shown) can also reduce the number of fasteners 73 required for assembly and shortens the overall assembly time. Optical components can be assembled manually to the optics bench 42 and parts designed so that access and vision of the assembler is not restricted by any other part. The fasteners 73 can be standardized in all the sub-assemblies for metric M4 size bolts except in the top cover. Standardizing fasteners 73 help in economies of scale and also simplifies the assembly process. Slots in the optics bench casing have sufficient clearance to allow an unobstructed assembly path and to prevent damage to the optical components during assembly.

Finally, the optics bench assembly 40 can be made of materials that can have: (1) a low coefficient of thermal expansion to maintain dimensional stability; (2) a high thermal conductivity to minimize distortion due to thermal gradient; (3) a high stiffness to minimize vibration sensitivity; and (4) a high strength and toughness to minimize deformation during impact loading Thermal expansion can be compensated by having an effective and robust thermal management system that maintains the average temperature of the optics bench assembly 40 within acceptable limits. Thermal gradients cause distortion of components and parts for which compensation is not possible. Therefore, during material selection, minimizing thermal gradients can be given priority. In addition, vibration causes natural excitation which induces noise into the LC system 2 due to which the functionality of the detector 4 can be severely affected. Material cost and easy availability are also important considerations while selecting the final suitable material. The Ashby methodology of material selection is used to find the best suited material for the optics bench.

TABLE 9

Translation Chart for Material Selection

| FUNCTION | Support and protect optical components |
|---|---|
| CONSTAINTS | Optics bench shape and dimensions |
| OBJECTIVE | Maximize thermal conductivity, minimize vibration sensitivity, minimize deformation during impact loading |
| FREE VARIABLES | Material |

Figure 30:
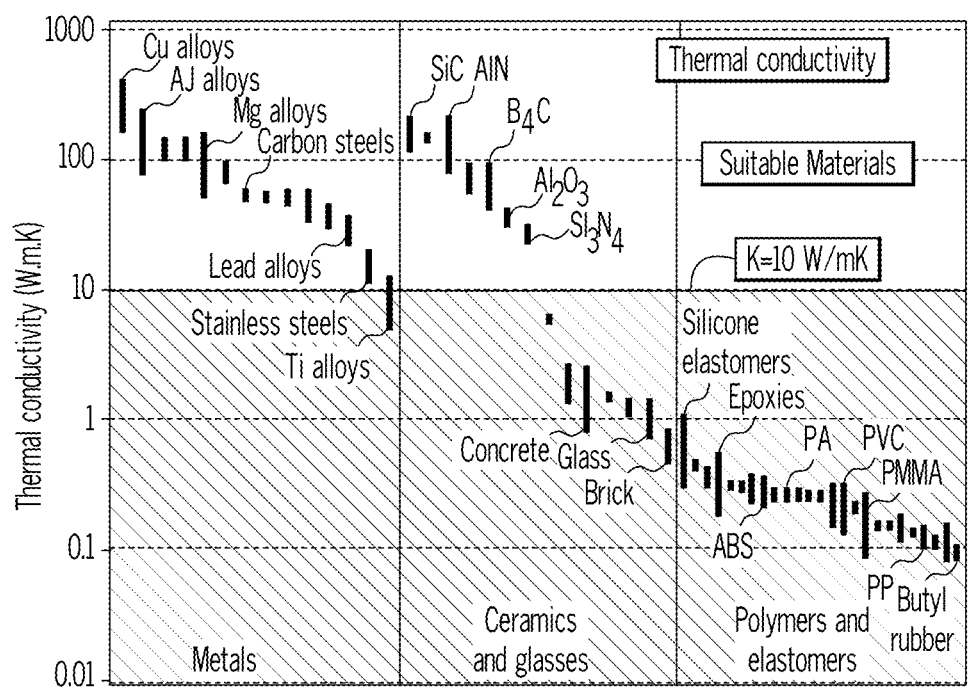
FIG. 30 provides a chart of thermal conductivity for screening suitable materials for the optics bench assembly based on thermal conductivity.

The optics bench assembly 40 can be made of material that can easily remove the heat generated in internal components during operation to prevent build-up of high temperatures inside the optics bench 42. This can be achieved by having a material that has high value of coefficient of thermal conductivity. As the first screening step, materials with coefficient of thermal conductivity smaller than 10 W/mK are eliminated. As shown in FIG. 30, only metals and majority of ceramics qualify as suitable materials after the first screening step. the performance index is found out by considering a simple case of one dimensional heat flow through the walls of the optics bench. The steady state Fourier law is given by Equation 21, where $$q = -\lambda \frac{dT}{dx} \tag{21}$$

Material Index for Minimizing Thermal Gradient

The performance index is obtained by one dimensional heat flow through the walls of the optics bench. The steady state Fourier law is given by Equation 22, where q is the heat flux, $\lambda$ is coefficient of thermal conductivity of the material and $$\frac{dT}{dx}$$

is temperature gradient.

$$q = -\lambda \frac{dT}{dx} \quad (22)$$

The strain developed due to temperature gradient is given by Equation 23, where $\alpha$ is coefficient of linear expansion of the material and $\Delta T$ is the difference in temperature of the optics bench casing and the ambient temperature.

$$\epsilon = \alpha \Delta T \quad (23)$$

$$\frac{d\epsilon}{dx} = \alpha \frac{dT}{dx} \quad (24)$$

Equation 25 is derived by combining Equations 23 and 24, where $$\frac{d\epsilon}{dx}$$

is the measure of distortion due to thermal gradient.

$$\frac{d\epsilon}{dx} = q\left(\frac{\alpha}{\lambda}\right) \quad (25)$$

Now the thermal gradient can be minimized by minimizing the value of $$\frac{\alpha}{\lambda}$$

of selecting materials with large values of index $M_1$, which is given by Equation 26.

$$M_1 = \frac{\lambda}{\alpha} \quad (26)$$

Figure 31:
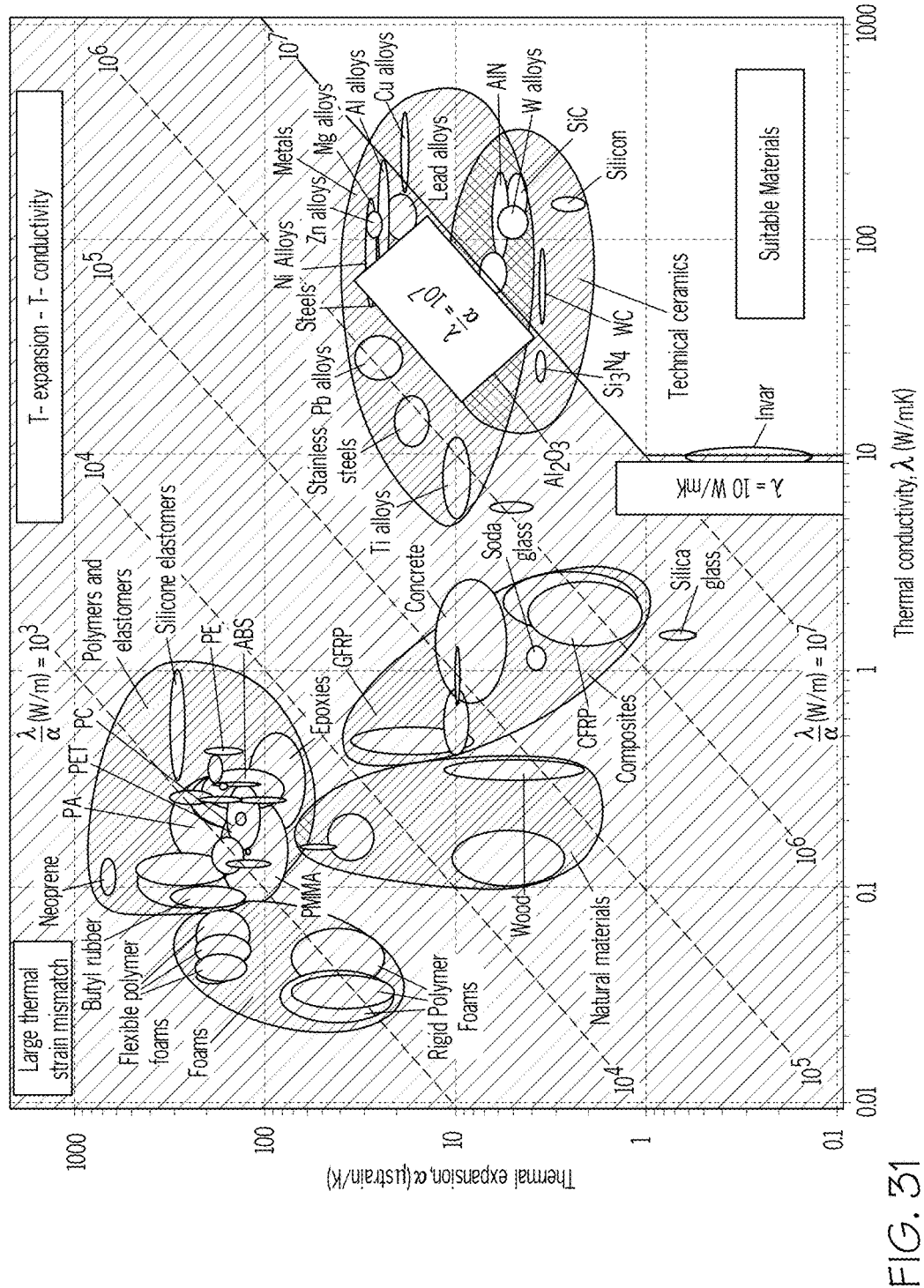
FIG. 31 provides a chart of thermal expansion versus thermal conductivity for selection of suitable material for the optics bench assembly with good dimensional stability and low thermal distortion.

To have good dimensional stability and minimize distortion due to thermal gradient, the material should have low coefficient of thermal expansion and high coefficient of thermal conductivity. FIG. 31 shows that the value of the index $$M_1 = \frac{\lambda}{\alpha}$$

increases by moving towards the bottom right side of the chart. The attribute limits are set at $\lambda = 10$ W/mK and $$M_1 = 10^7 \frac{\mu stain/K}{W/mK}$$

to eliminate materials with low thermal conductivity and high thermal expansion. Metals such as aluminum, copper, tungsten alloys, silicon and technical ceramics such as tungsten carbide, silicon carbide, aluminum nitride satisfy the above criteria.

Material Index for Minimizing Vibration Sensitivity

The sensitivity to the external excitation is minimized by maximizing the natural frequencies of the component. For the sake of simplicity, the optics bench is assumed to be resting on two mounting supports and excitation force acting through its center of gravity. This is equivalent to a light and stiff square beam of side b, subjected to three point bending load. Stiffness of the beam in the above condition is given by Equation 27, where F is the force acting on the beam, $\delta$ is the deflection of the beam, E is the Young's modulus of the beam's material, L is the length of the beam, I is the second moment of area given by $$\frac{b^4}{12} \text{ or } \frac{A^2}{12},$$

A is the cross-sectional area of the beam and C is a constant whose value depends on the type of the loading.

$$S = \frac{F}{\delta} = \frac{CEI}{L^3} \quad (27)$$

Mass of the beam is given by Equation 28, where $\rho$ is the density of the beam's material.

$$m = \rho AL \quad (28)$$

Combining equation for stiffness and second moment of inertia with the mass equation we get Equation 29.

$$m = \left(\frac{12S}{C}\right)^{1/2} (L)^{5/2} \left(\frac{\rho}{E^{1/2}}\right) \quad (29)$$

The flexural vibrations have lowest frequencies and they are proportional to $$\frac{E^{1/2}}{\rho}.$$

Ashby, M. F. *Materials Selection in Mechanical Design Third Edition,* 3rd ed. 2005. Thus the sensitivity to vibration can be minimized by selecting a material with large value of the index $M_2$ given by Equation 30.

$$M_2 = \frac{E^{1/2}}{\rho} \quad (30)$$

Figure 32:
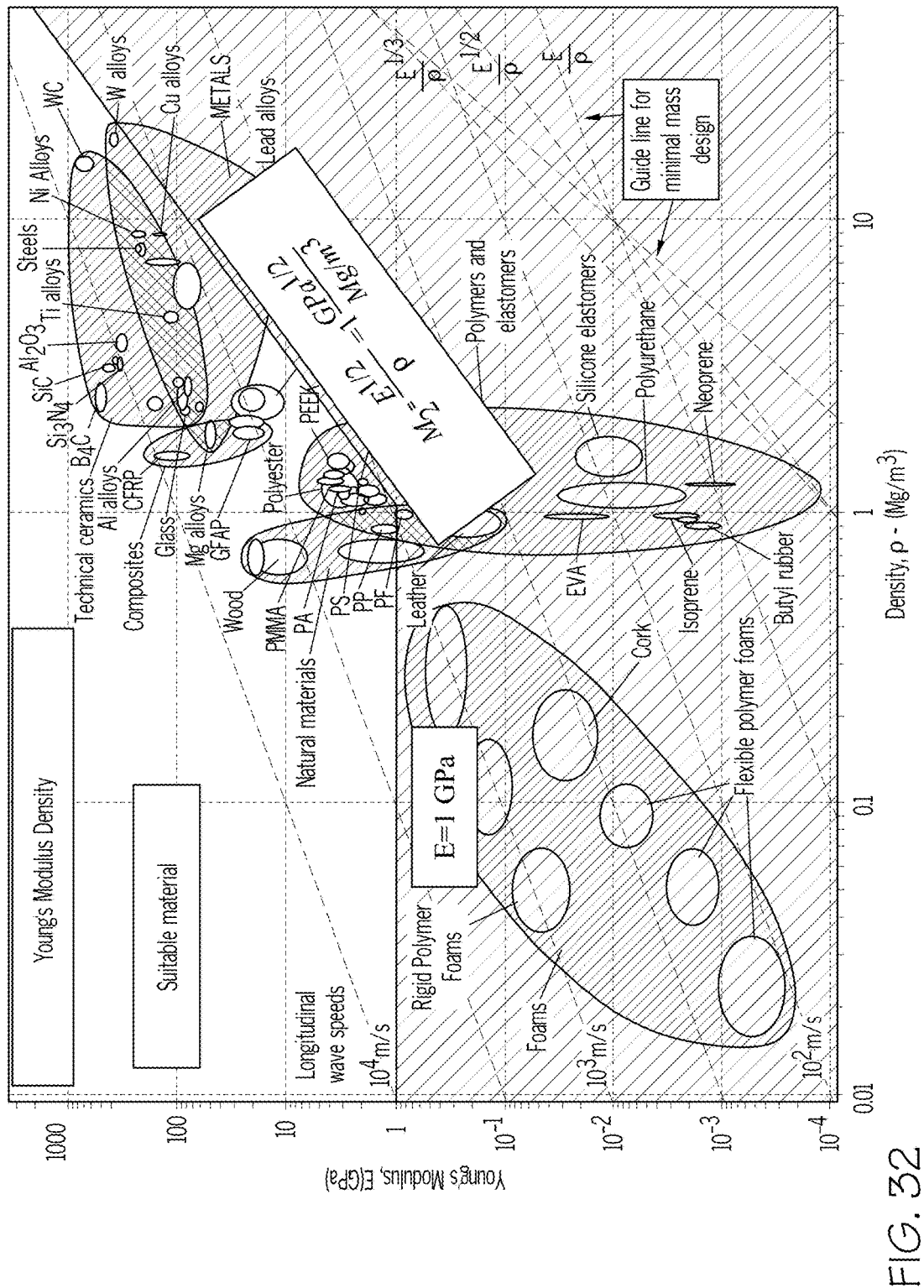
FIG. 32 provides a chart of Young's modulus versus density for selection of material with low vibration sensitivity.

As shown in FIG. 32, value of the index $M_2$ increases by moving towards the top left corner of the chart. The attribute limits are set at E=1 GPa and $$M_2 = 1 \frac{\text{GPa}^{1/2}}{\text{Mg/m}^3}$$

to eliminate materials of low stiffness. Some of the qualifying materials according to the above criterion are ceramics, majority of the metals, composites and some natural materials such as wood.

Material Index for Minimizing Deformation During Impact Loads

During impact loading, it is assumed that the optics bench of mass m falls from a height h under the influence of gravity. After contact with the floor the optics bench deforms due to stresses developed. The amount of deformation depends on the stiffness of the component. The change in potential energy U after the impact is given by Equation 31.

$$U = mgh \quad (31)$$

This energy is absorbed by the material through the deformation of the component. This is known as strain energy and is given by Equation 32, where σ is the stress developed due to impact loading, ε is the strain developed in the material, V is the volume of the part.

$$\text{Strain Energy} \propto \sigma \epsilon V \quad (32)$$

The Hooke's law relation is given by Equation 33.

$$E = \frac{\sigma}{\epsilon} \quad (33)$$

Substituting Equation 33 into Equation 32, gives the elastic strain energy per unit volume, the expression for which is given by Equation 34.

$$\text{Elastic Strain Energy stored per unit volume} \propto \frac{1}{E}\sigma^2 \quad (34)$$

The optics bench will be permanently deformed if the stress σ developed after impact loading exceeds the failure strength $\sigma_f$ of the material. Therefore to prevent deformation, the stress developed in the part after impact loading can be less than the failure strength of the material. This constraint is shown by Equation 35.

$$\sigma \leq \sigma_f \quad (35)$$

The maximum strain energy that can be stored in the body without permanent deformation is known as proof resilience $U_m$, which is given by Equation 36. Therefore the objective is to maximize the maximum energy density or proof resilience of the body.

$$U_m \propto \frac{\sigma_f^2}{E} \quad (36)$$

Thus the deformation after impact loading can be minimized, by selecting a material with large value of the index $M_3$, given by Equation 37.

$$M_3 = \frac{\sigma_f^2}{E} \quad (37)$$

Figure 33:
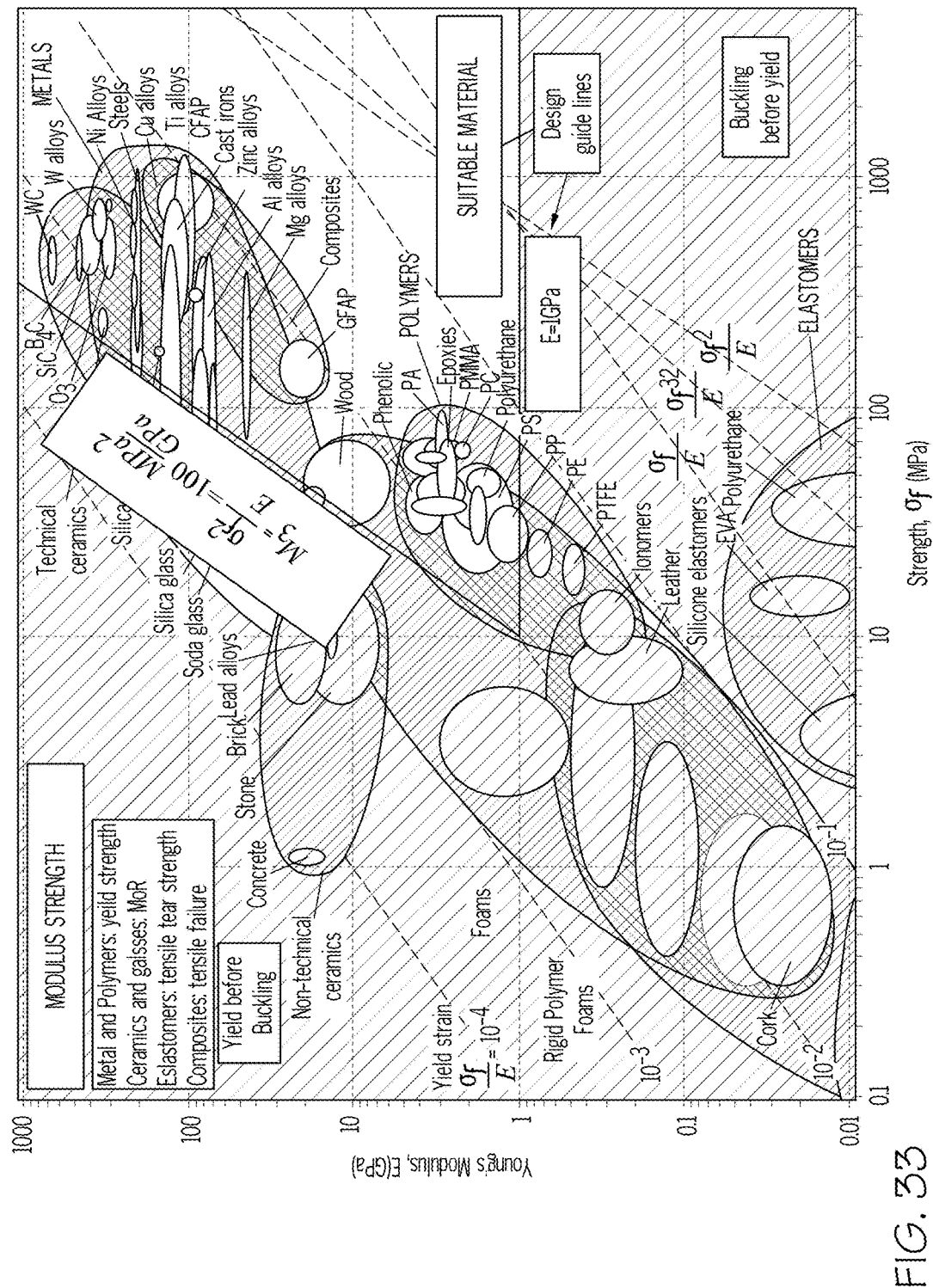
FIG. 33 is a chart of Young's modulus versus strength for selection of material with high resistance to deformation during impact loads.

As shown in FIG. 33, value of the index $M_3$ increases by moving towards the right of the chart. The attribute limits are set at E=1 GPa and $$M_3 = 100 \ \frac{\text{MPa}^2}{\text{GPa}}$$

to eliminate materials with low value of Young's modulus and low strength. Some of the qualifying materials according to these criteria are ceramics such as Tungsten carbide, Silicon Carbide, most of the metals, composites and some of the polymers such as PMMA, PC, Polyurethane, and Polyamide.

Material Properties Comparison

The material properties are shown in the Table 10 for comparison. The values of the material indices M1, M2 and M3 as shown in Table 4, are derived from Table 10.

TABLE 10

Mechanical Properties of Top Ranked and Common Materials

| MATERIAL | E (GPa) | Yield Strength (MPa) | Thermal Conductivity (W/mK) | Thermal Expansion ($10^{-6}$/K.) | Density ($10^3$ kg/m$^3$) |
|---|---|---|---|---|---|
| Silicon Carbide | 350 | 3125 | 155 | 4 | 3.1 |
| Aluminum Nitride | 320 | 2335 | 140 | 5 | 3.29 |
| Aluminum | 72.4 | 170 | 151 | 21.4 | 2.67 |
| Copper | 130 | 265 | 275 | 17 | 8.93 |
| Zinc | 80 | 265 | 117 | 25 | 6 |
| Steel | 200 | 750 | 15 | 16 | 7.8 |
| PEEK | 4 | 80 | 0.25 | 133 | 1.31 |
| Bulk Molding Compound (BMC) 940 [11] | 95 | 28 | 13 | 30 | 1.89 |

TABLE 11

Material Indices of Top Ranked and Common Materials

| Material | $M_\lambda = \frac{\lambda}{\alpha}$ $\left(\frac{\text{W/mK}}{10^{-6}/\text{K}}\right)$ | $M_2 = \frac{E^{\frac{1}{2}}}{\rho}$ $\frac{(\text{MPa})^{\frac{1}{2}}}{\text{Mg/m}^3}$ | $M_3 = \frac{\sigma_f^2}{E}$ $\frac{(\text{MPa})^2}{\text{GPa}}$ |
|---|---|---|---|
| Silicon Carbide | 38.75 | 6.0 | 27902 |
| Aluminum Nitride | 28.00 | 5.4 | 17038 |
| Aluminum | 6.95 | 3.2 | 936 |
| Copper | 16.17 | 1.3 | 540 |
| Zinc | 4.68 | 1.5 | 878 |
| Steel | 0.94 | 1.8 | 2813 |
| PEEK | 0.002 | 1.5 | 1600 |
| Bulk Molding Compound (BMC) 940 [11] | 0.43 | 1.6 | 83 |

As shown in Table 10 and Table 11, silicon carbide has the best overall properties for the optics bench application followed by aluminum nitride and aluminum. Polymers do not qualify mainly due to the poor ratio of thermal conductivity to thermal expansion, which will lead to distortion and dimensional instability at high operating temperatures.

Supporting Information for Material Selection
UV Compatibility

Since the detector uses UV-LEDs as the light source, one of the basic requirements of the materials used for the optics bench 42 is to be UV compatible and resist photo degradation under long UV exposure. This is also necessary in order to have a long lifecycle of the optics bench since materials that are not UV stable will degrade over time and become brittle, crack, decolorize, warp, etc. UV compatibility can be drastically improved by coating the base material with other materials which prevent UV degradation and also absorb/suppress any stray or scattered UV radiation. Ceramics and Metals are much less susceptible to UV based damage as compared to polymers. Therefore ceramics such as SiC or AlN and metals such as aluminum are better suited materials for the optics bench than polymers.

Material Cost

Figure 34:
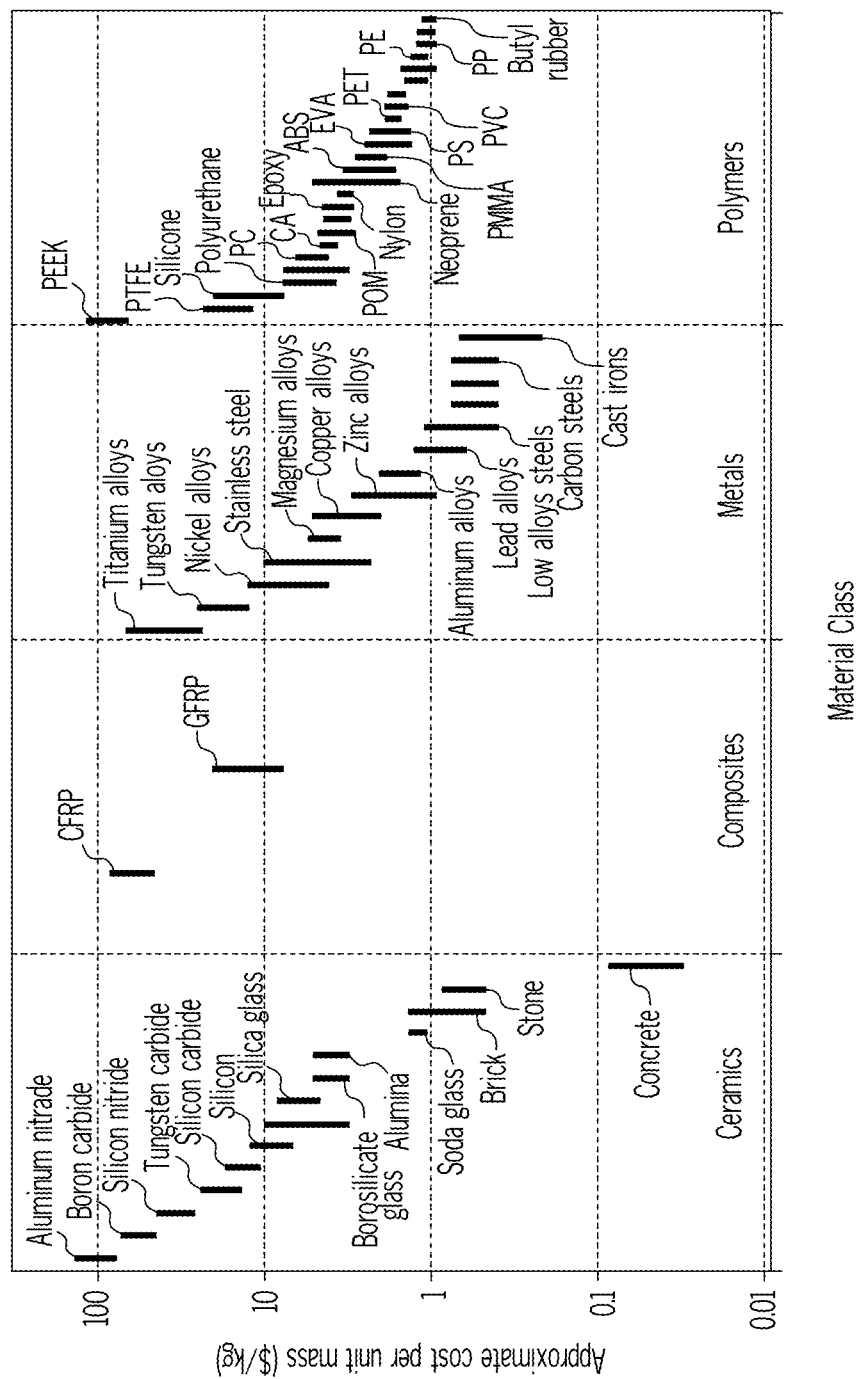
FIG. 34 is a chart of cost per unit weight of different material classes.

FIG. 34 shows the cost per unit weight of different material class. An approximate cost comparison (cost per unit weight) between aluminum and ceramics (SiC and AlN) shows that ceramics costs at least 5 times than that of aluminum alloys. This cost difference outweighs the advantages in properties that ceramics have over aluminum. Thus using ceramics as a material for optics bench is not practical due to its prohibitively high cost.

Availability

Aluminum and its alloys are more readily available and more widely used as compared to ceramics. The manufacturing infrastructure for aluminum is also well established and readily accessible and compared to ceramics aluminum processing is cheaper.

Selection of Aluminum Alloy

The analysis that aluminum is a suited material for the optics bench takes into consideration a lot of factors such as strength, dimensional stability, vibration sensitivity and cost. Aluminum alloys have much better properties for optomechanical applications than pure form of aluminum. Some of the commonly used aluminum alloys are Alloy 1100, Alloy 2024, Alloy 6061, Alloy 7075 and Alloy 356. Out of these, Alloy 356 is the best suited alloy for general purpose optical instruments. The main alloying composition for aluminum 356 is 7% Silicon and 0.3% magnesium. The higher purity variant of the alloy (in terms of chemical composition) is designated with an A before the number 356. Some of the properties of aluminum A356 are good castability by sand, permanent mold and die casting methods making it an excellent candidate for intricate and complex castings including: good machinability characteristics; moderate to high strength; excellent corrosion resistance and good weldability characteristics. The common mechanical properties of aluminum A356 is shown in the Table 12 immediately below.

TABLE 12

Mechanical Properties of Aluminum Alloy A356

| Material | Young's Modulus (GPa) | Yield Strength (MPa) | Thermal Conductivity (W/mK) | Thermal Expansion ($10^{-6}$/K.) | Density ($10^3$ kg/m$^3$) |
| --- | --- | --- | --- | --- | --- |
| Al A356 | 72.4 | >165 | 151 | 21.4 | 2.67 |

EXAMPLE VII

Engineering Analysis of the Optics Bench Assembly

Figure 35:
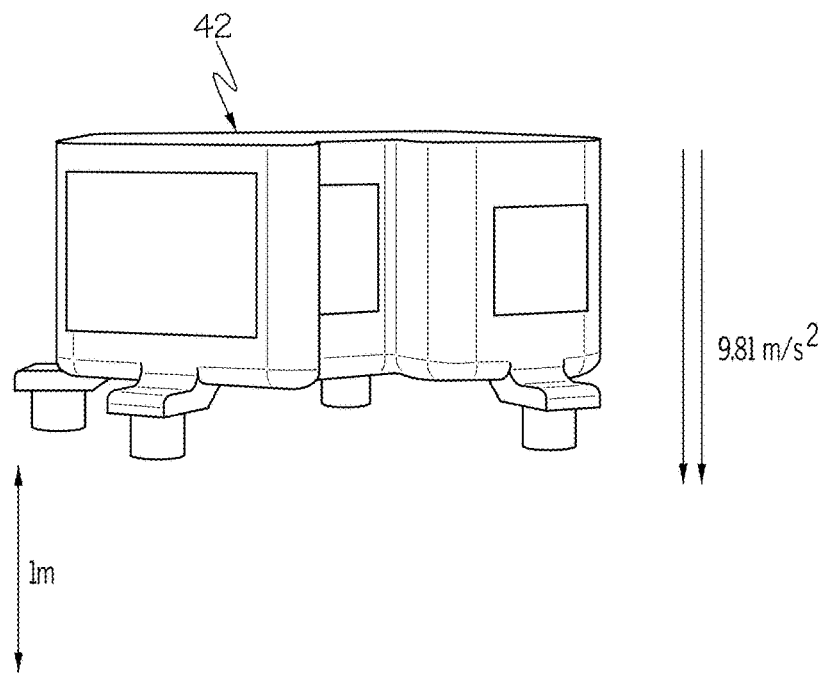
FIG. 35 shows an embodiment of the optics bench assembly for drop test analysis.

A drop test analysis on 3D CAD software simulation can be carried out to test if the optics bench 42 (as used in an optics bench assembly 40 described herein) can maintain its structural integrity when it is subjected to impact loads. As shown in FIG. 35, this test can be carried out under the assumption that the optics bench 42 will fall freely on the base from height of 1000 mm on a rigid ground under the influence of acceleration due to gravity. The testing specification is in accordance with the "Optics and Photonics-Environmental test methods—ISO 9022" (Appendix A, Method 33 Freefall test); Yoder, P., *Opto-Mechanical Systems Design, Fourth Edition, Volume 1: Design and Analysis of Opto-Mechanical Assemblies*, Vol. 1, CRC Press, 2015.

The amount of stress developed in an optics bench casing 44 due to the impact loading can be analyzed and compared with the yield strength of aluminum A356. The optics bench 42 should be designed such that it not only maintains its shape and form after the impact but it can protect the parts of the assembly mounted within it. To simplify the meshing and analysis, the optical components are modeled as cuboid having the same mass as that of original parts.

Figure 36:
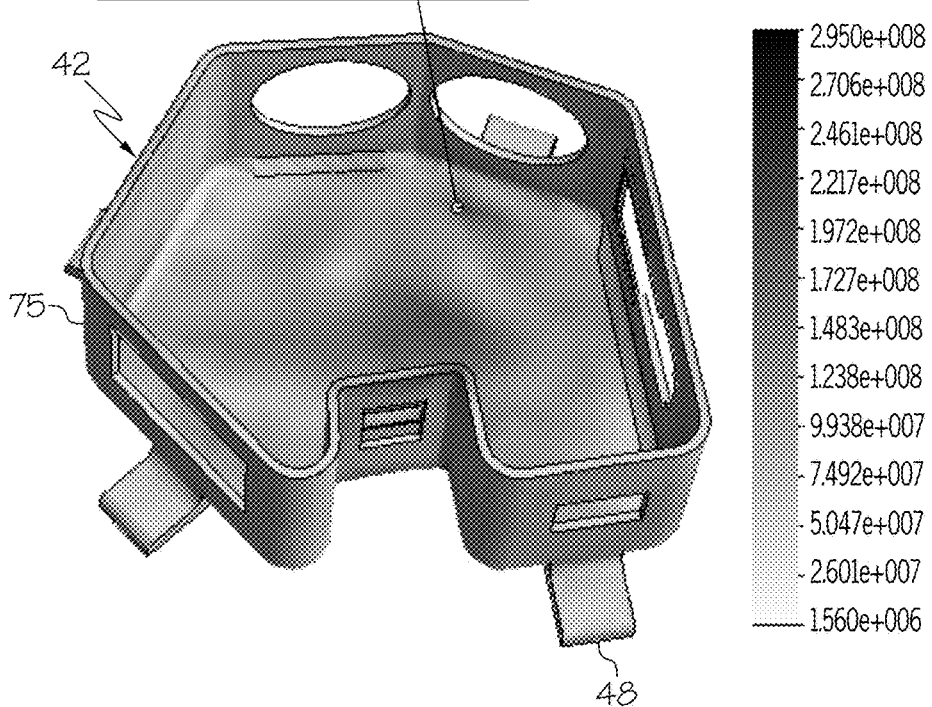
FIG. 36 shows an embodiment of the optics bench assembly for drop test analysis with wall thickness 4 mm without shock mounts.

In an embodiment, the optics bench 42 was tested for impact loading having a wall thickness of 4 mm. The results of the drop test on the optics bench 42 having a 4 mm wall thickness is shown in FIG. 36. The results indicate that the maximum stress value is 233.6 MPa. This value is much greater than the yield strength of an aluminum wall (A 356) which is around 170 MPa. The results show that the maximum value of the stress is developed near the grating and mirror mounting area. This would not only result in permanent deformation of optics bench 42 but also damage the optical components contained therein.

Figure 37A:
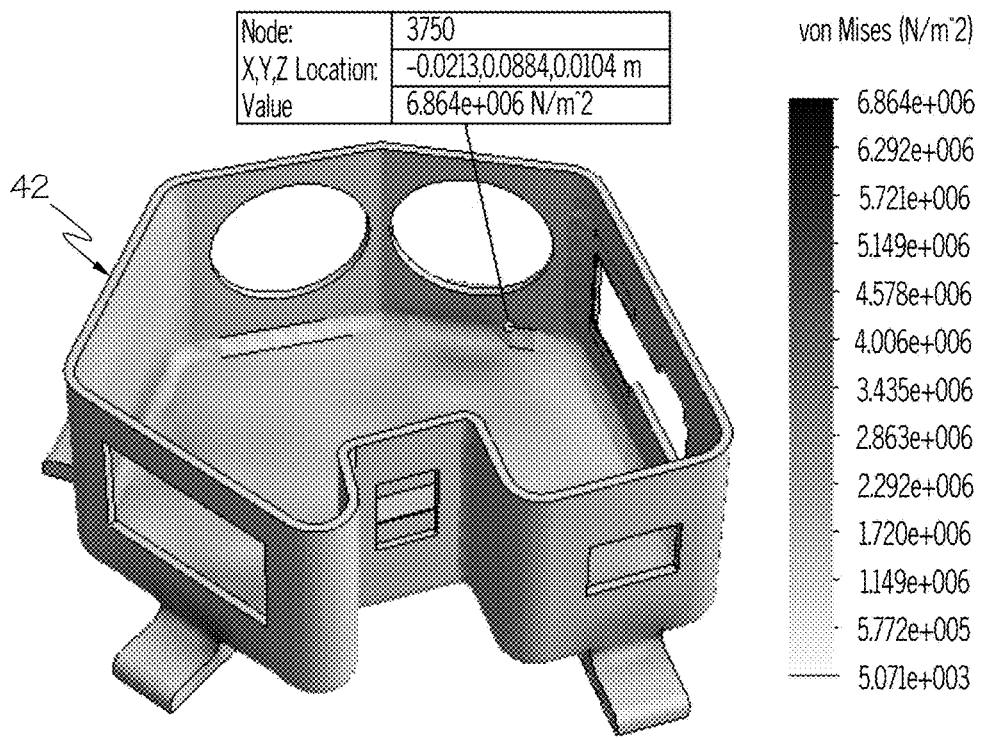
Figure 37B:
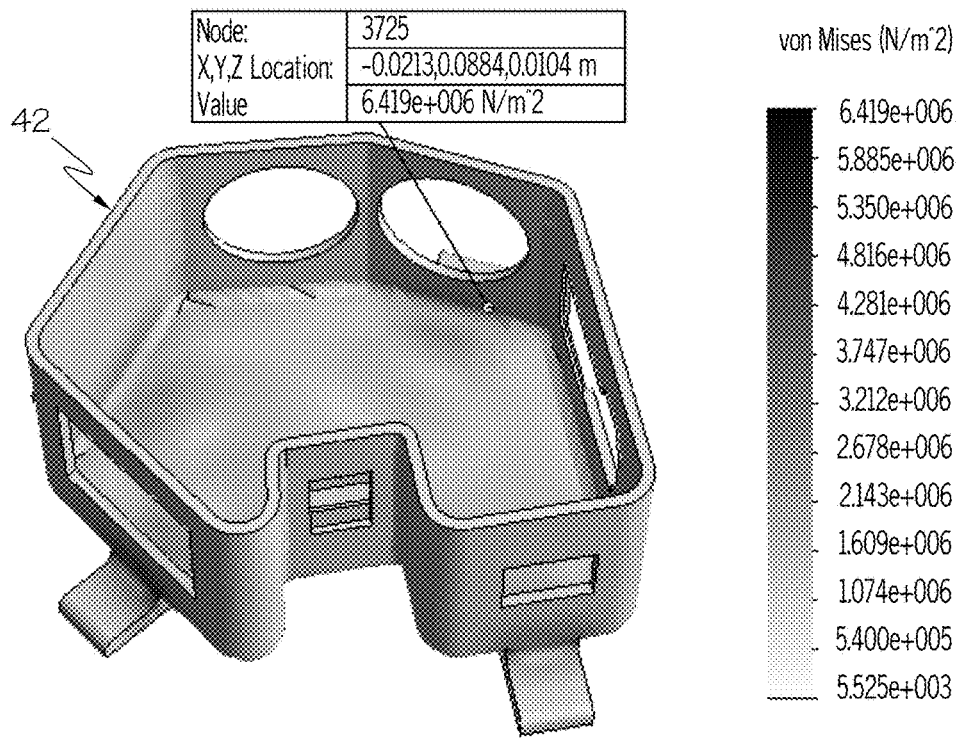
Figure 37E:
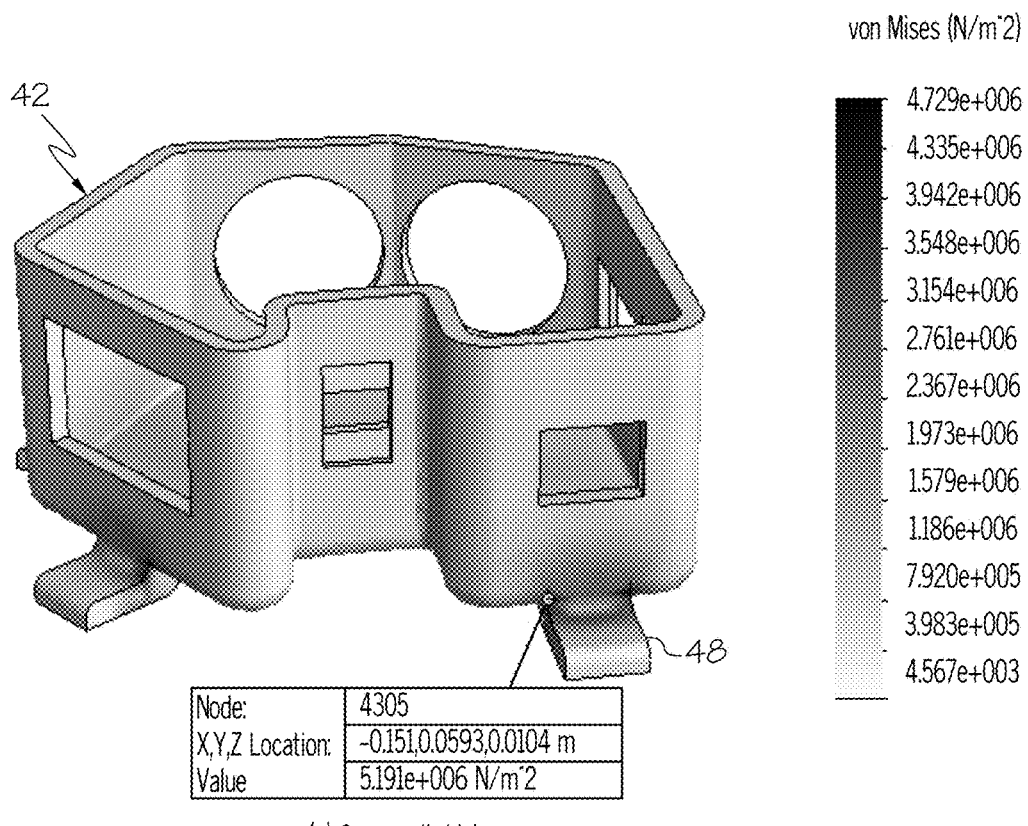

Therefore, a plurality of shock mounts 48 (shock and vibration isolators) should be used at mounting points of the optics bench 42 and also at the base of a detector frame 46 to protect the delicate optical components in case of an impact. The shock mounts also act as vibration isolators for the optics bench assembly 40. The shock mounts 48 are modelled as a cylinder made of neoprene measuring 25 mm in diameter and 20 mm in length. The results of the drop test analysis with elastomeric shock mounts (also referred to as shock absorbers) carried out for different wall thickness starting from 4 mm to 8 mm are shown in FIG. 37. The results indicate significant reduction in the stress values. FIG. 37A shows that optics bench 42 with 4 mm wall thickness has maximum stress value of 6.864 MPa. This is lower than the yield strength of aluminum A356 (170 MPa). Optical glass can withstand tensile stresses of 6.9 MPa (1,000 psi) and compressive stresses of 345 MPa (50,000 psi) before problems or failure occur, thus an objective is to keep the stress levels lower than 6.9 MPa. Schwertz, K., *Useful Estimations and Rules of Thumb for Optomechanics*, The University of Arizona, 2010. Further reduction in maximum stress values can be achieved by choosing the optimal wall thickness of the optics bench 42.

Figure 38:
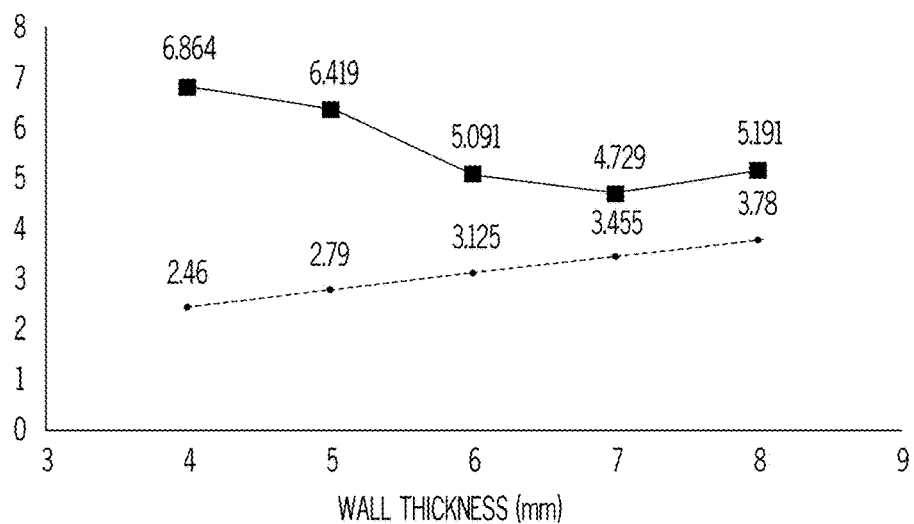
FIG. 38 is a graph depicting variation of maximum stress during impact loading and overall weight of the optics bench assembly with increasing wall thickness.
Figure 39A:
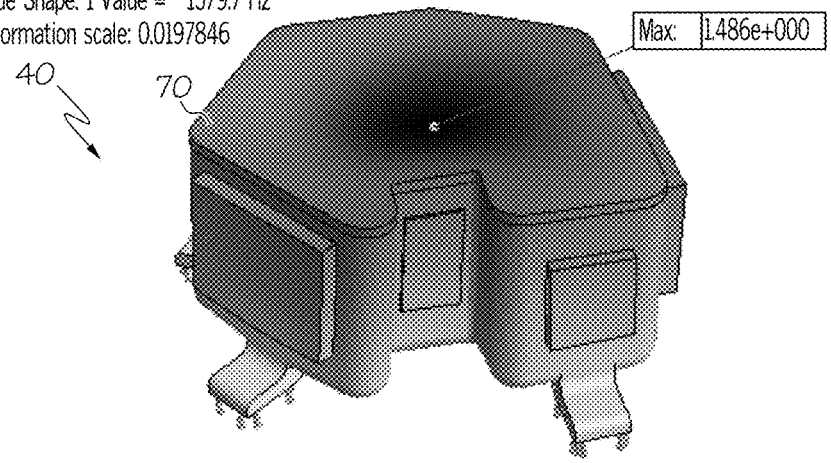
FIGS. 39A, 39B, 39C, 39D and 39E show first five vibration modes of the optics bench assembly.
Figure 39B:
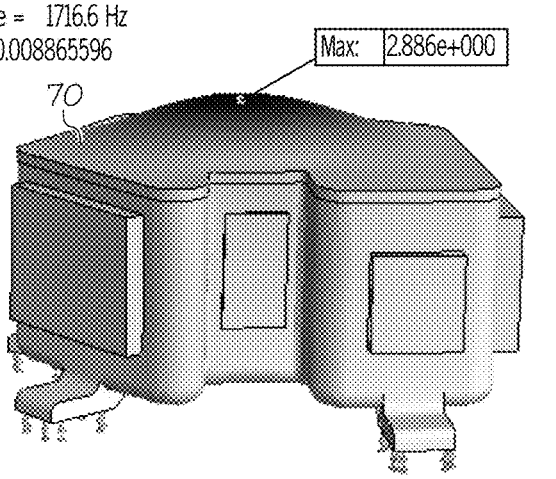
Figure 39C:
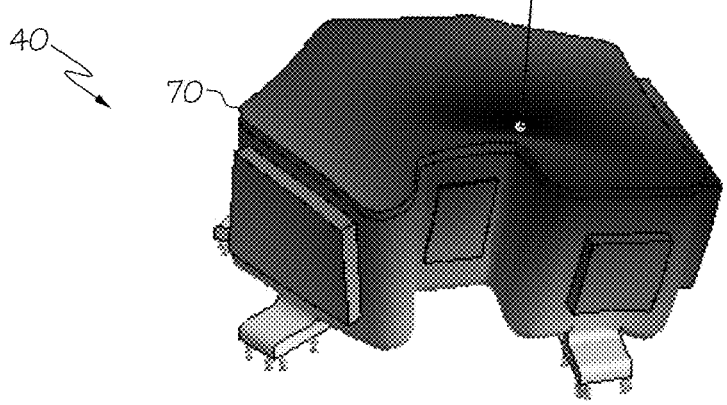
Figure 39D:
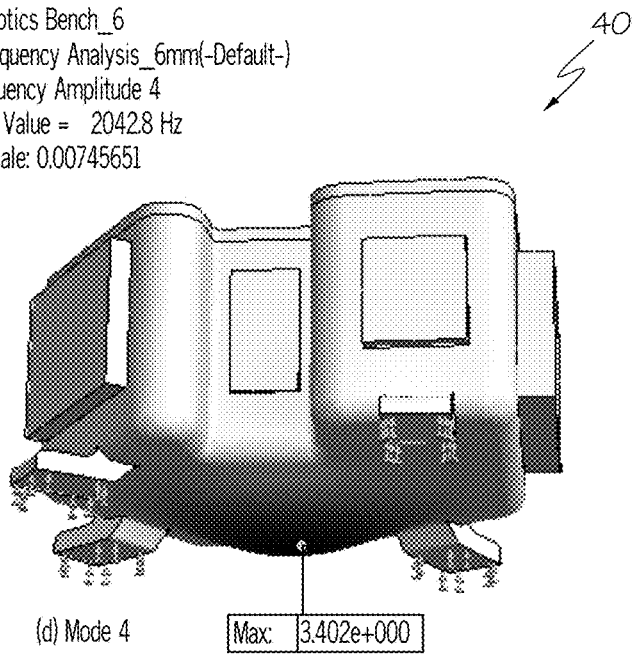
Figure 39E:
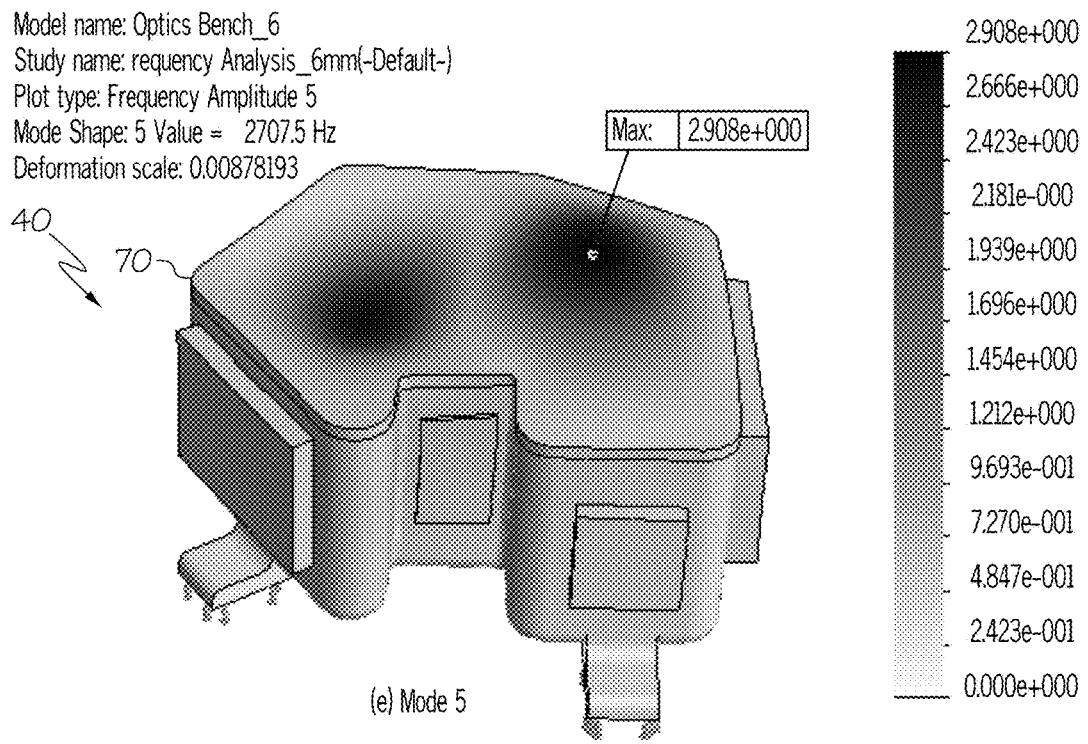

The plot of maximum stress developed in the optics bench casing 44 during impact versus the wall 75 thickness is shown in FIG. 38. The plot indicates that the maximum stress value in a drop test reaches a minimum for a wall thickness of 7 mm. The increase in wall thickness increases the overall weight of the optics bench assembly 40 which in turn increases the material cost. Therefore a thickness value between 6 and 7 mm will be a good tradeoff between minimizing the stress values and keeping the weight of the part within acceptable limits. For a thickness value in this range, the maximum stress during impact in the optics bench assembly 40 with shock mounts 48 will around 5 MPa. This value is lower than the failure strength of the glass (6.9 MPa).

Vibration Analysis

Uncontrollable sources of vibration such as fans, air conditioners, pumps, motors, road and rail transportation, etc., can lead to vibration induced performance degradation in precision optical components. Since UV light has wavelength of around 0.2 microns, vibrations with amplitude even in sub-micron range can seriously hamper the performance of the detector by eclipsing valuable data under vibration induced noise. Therefore it is necessary to isolate the critically aligned optical components from the above sources of vibration disturbances.

Resonance in opto-mechanical devices can be avoided by designing parts with high stiffness so that their natural frequencies of vibration are significantly higher than those of anticipated driving forces. Frequency analysis was carried out in 3D CAD software program to find the optimal wall thickness that maximizes the natural frequency and stiffness of the optics bench. In this analysis the mounting points of the optics bench were fixed and the bench assembly was made to vibrate in different natural frequency modes. The first five vibration modes of the optics bench assembly 40 are shown in FIG. 39. Out of these first five vibration modes, mode 3 is of major concern because the optical components vibrate in and out relative to each other. This mode will affect the performance of the detector because it changes the relative distances between the optical components which results in loss of resolution and sensitivity.

Figure 40:
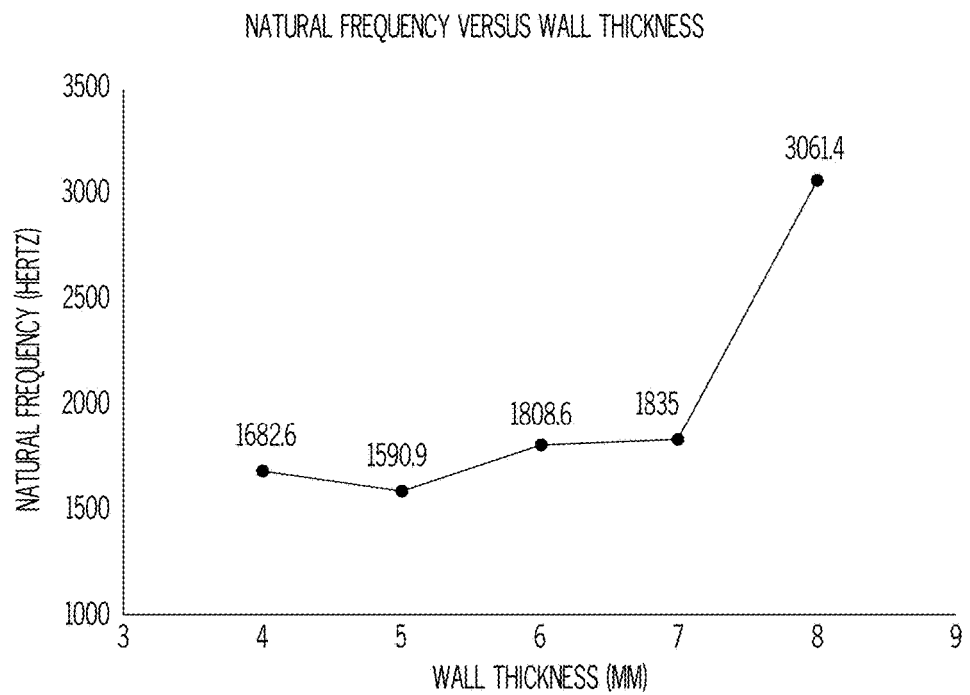
FIG. 40 is a graph depicting variation of natural frequency of optics bench assembly in critical mode with optics bench casing wall thickness.

The results of the vibration analysis show the natural frequency of vibration of the optics bench assembly 40 in different modes are each above 1400 Hz. This frequency range is much higher than the ambient vibration disturbances, which is typically in the range of 4-100 Hz range. Such large frequency differences between resonant and excitation frequencies prevent energy coupling between the optics bench assembly 40 and its support structure. Thus the optics bench assembly 40 can be isolated from ambient vibration disturbances. The variation of mode 3 (critical mode) natural frequency of optics bench assembly 40 for different wall thickness of optics bench casing is shown in FIG. 40. The components with high natural frequency of vibration have higher stiffness and are less sensitive to external vibration disturbances. Therefore the optics bench assembly 40 with optimal wall thickness will maximize the natural frequency of vibration.

The results of the frequency analysis show that increasing the wall thickness increases the natural frequency of vibration. The drop test analysis shows that a wall thickness of 8 mm increases the stress values during impact/shock loading and also increases the weight as well as the material cost. A wall thickness between 6 and 7 mm is a good compromise which leads to low stress during drop test, high natural frequency of vibration (around 1800 Hz), and results in the weight of the optics bench assembly 40 which is within acceptable limits. Based on the results of drop test and vibration analysis a wall thickness of 6.35 mm (¼ inch thick) is selected for the optics bench. In terms of manufacturability, optics bench with 6.35 mm wall thickness can also be easily manufactured with conventional or advanced casting methods.

Vibration Isolation

The optics bench assembly 40 can have a natural resonant frequency as high as possible and damped. Damping is achieved by selecting an appropriate vibration isolator. Vibration dampers cause the oscillation in a solid body to decay to zero amplitude by diverting the energy from vibration to other sinks. Damping helps to minimize the duration and amplitude of external vibrations. The first step in selecting a vibration isolator is determining the severity of environment in which the optics bench assembly 40 is going to be used and the severity of the application. These two factors will determine the level of isolation required for the optics bench assembly 40.

Liquid chromatography instruments are usually operated in lab environments so the external vibration disturbances are typically in the range of 4-100 Hz. The major sources of vibration for the optics bench will be cooling fans in the detector module, motors driving needle drive mechanism, and pumps and motors in sample manager. Considering the rated speed of fans and motors which is in the range of 1500-3000 rpm, the excitation frequencies will be in the range of 25-100 Hz. Therefore, all frequencies above 25 Hz can be isolated by using vibration isolators. Any excitation frequency below 25 Hz range will not have any significant effect in the performance of the detector system.

While calculating the correct specifications of the vibration isolators, the lowest disturbing frequency is considered. This is because if the lowest frequency is isolated, then all other higher frequencies will also be isolated. The theory behind vibration isolation is discussed herein. The calculations for finding the right vibration isolator for the optics bench system are discussed below. The Mass W of the optics bench assembly 40 as obtained from a 3D CAD model is 3.086 kg. Assuming center of gravity of the optics bench assembly 40 is centrally located in the horizontal plane, load $W_L$ per mounting point is given by Equation 38.

$$W_L = \frac{W}{4} \tag{38}$$

As discussed herein, for effective isolation of the optics bench from vibrations disturbances, the maximum isolator natural frequency $f_n$ is given by Equation 39, where $f_d$ is the minimum disturbing frequency.

$$f_n = \frac{f_d}{\sqrt{2}} \tag{39}$$

The static deflection $\Delta_s$ for this natural frequency is given by Equation 41, where g is the acceleration due to gravity.

$$f_n = \frac{1}{2\pi}\sqrt{\frac{g}{\Delta_s}} \tag{40}$$

$$\Delta_s = \frac{g}{(2\pi f_n)^2} \tag{41}$$

The required spring rate K for the isolator at the mounting point is given by Equation 42.

$$K = \frac{\text{Load/mount}(W)}{\text{Deflection } \Delta_s} \tag{42}$$

Table 13 shows the calculated values $f_d$, $f_n$, $\Delta_s$ and K for the vibration isolator that would provide the desired level of isolation.

TABLE 13

Selection of Vibration Isolator

| Load per mounting point $W_L$ (kg) | External Disturbance Frequency $f_d$ (Hz) | Maximum Isolator Natural Frequency $f_n$ (Hz) | Static Deflection $\Delta_s$ (mm) | Isolator spring rate K (kg/mm) |
|---|---|---|---|---|
| 0.772 | 25 | 17.677 | 0.8 | 0.965 |

Figure 41:
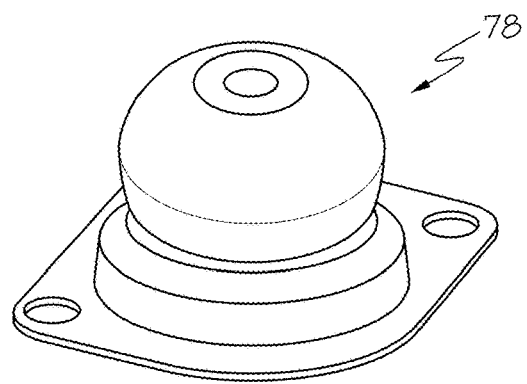
FIG. 41 illustrates a low frequency bubble mount vibration isolator.

Isolators that have $f_n$ lower than 17.677 Hz will isolate the optics bench assembly 40 from external vibration disturbances. Many vibration isolators matching the specifications shown in Table 13 are available online. Bubble mounts from Tech Products as shown in FIG. 41, have a natural frequency of 8 Hz. It is made of neoprene which is chemically resistant to most solvents and each mount can take up to 2 kg of load. Also the dimensions of the isolator are compatible with the dimensions of the optics bench mounting foot.

Transmissibility T of the selected isolators is given by Equation 43.

$$f_n = \left| \frac{1}{1 - \left(\frac{f_d}{f_n}\right)^2} \right| \tag{43}$$

Table 14 shows that the selected vibration isolators will provide 88.59% isolation to the optics bench.

TABLE 14

Transmissibility of Vibration Isolator

| Ntural frequency of vibration isolator (Hz) | Transmissibility | Isolation (%) |
|---|---|---|
| 8 | 0.11408 | 88.59 |

Thermal Analysis
Calculation of Natural Convection Heat Transfer Coefficient

Figure 42A:
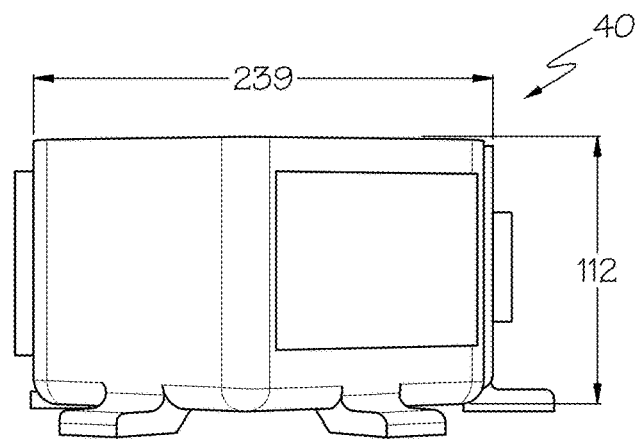
FIGS. 42A, 42B and 42C is an illustration of an embodiment of the optics bench assembly providing maximum dimensions for calculating a natural convection heat transfer coefficient.
Figure 42B:
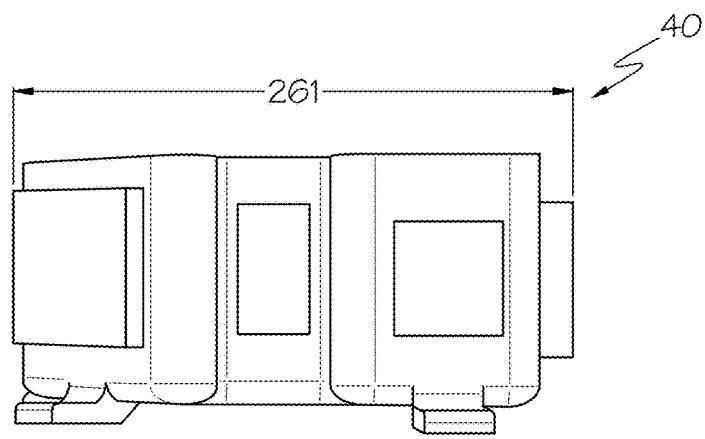
Figure 42C:
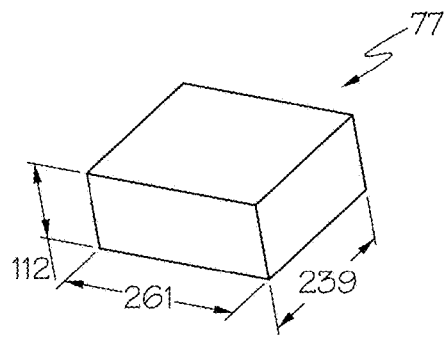

Before conducting thermal analysis, the natural convection heat transfer coefficient can be approximated. For calculation simplification the optics bench 42 is assumed to be a box 77 of dimensions 239×112×261 mm as shown in FIG. 42. The theory behind natural heat transfer coefficient calculations is discussed by çengel. Cengel, Y. A., *Heat and Mass Transfer: A Practical Approach*, 3$^{rd}$ ed., McGraw-Hill, 2007.

The ambient room temperature is assumed to be 27° C. (300K). The maximum operational temperature of the micro-mirror array in DMD which acts as the major heat source in the optics bench assembly 40 is around 60° C. Texas Instruments, DLP4710 0.47 1080p DMD 1, no. 1, 2015. Thus the maximum temperature difference between the optics bench components and ambient air is $\Delta T = 33°$ C. All side faces of the box can be assumed to be 112 mm high vertical surfaces. The natural convection heat transfer coefficient $h_1$ for vertical faces is given by Equation 44, where $\Delta T$ is the temperature difference and $L_1$ is the characteristic length.

$$h_1 = 1.42 \times \left(\frac{\Delta T}{L_1}\right)^{0.25} \tag{44}$$

Table 15 shows the natural heat transfer coefficient for side faces of the optics bench, which has characteristic length of 0.112 m.

TABLE 15

Natural Heat Transfer Coefficient for Vertical Surfaces of Optics Bench

| Characteristic Length $L_1$ (m) | Temperature difference $\Delta T$ (° C.) | Natural heat transfer coefficient for vertical surfaces $h_1$ (W/m$^{2°}$ C.) |
|---|---|---|
| 0.112 | 33 | 5.88 |

Similarly the top and bottom surfaces can be assumed as rectangular horizontal surfaces. The characteristic length L2 of the horizontal surfaces is given by Equation 45.

$$L_2 = \frac{4A}{P} \tag{45}$$

Table 16 shows the characteristic length for top and bottom surfaces, which has an area of 0.0623 m2 and perimeter of 1 m.

TABLE 16

Characteristic Length of Top/Bottom Surfaces of Optics Bench

| Area of top/bottom surface A (m$^2$) | Perimeter of top/bottom surface P (m) | Characteristic Length $L_2$ (m) |
|---|---|---|
| 0.0623 | 1 | 0.249 |

The natural convection heat transfer coefficient for bottom and top faces are given by Equation 46, where $\Delta T$ is the temperature difference and L2 is the characteristic length.

$$h_2 = 1.32 \times \left(\frac{\Delta T}{L_2}\right)^{0.25} \tag{46}$$

Table 17 shows the natural heat transfer coefficient for bottom and top faces of the optics bench 42, which has characteristic length of 0.249 m.

TABLE 17

Natural Heat Transfer Coefficient for Horizontal Surfaces of The Optics Bench Assembly

| Characteristic Length L (m) | Temperature difference $\Delta$ (° C.) | Natural heat transfer coefficient for horizontal surfaces $h_2$ (W/m$^{2°}$ C.) |
|---|---|---|
| 0.249 | 33 | 4.48 |

The above values of the coefficient of natural convention can be used in a thermal analysis.

Thermal Heat Sources in the Optics Bench Assembly

Figure 43:
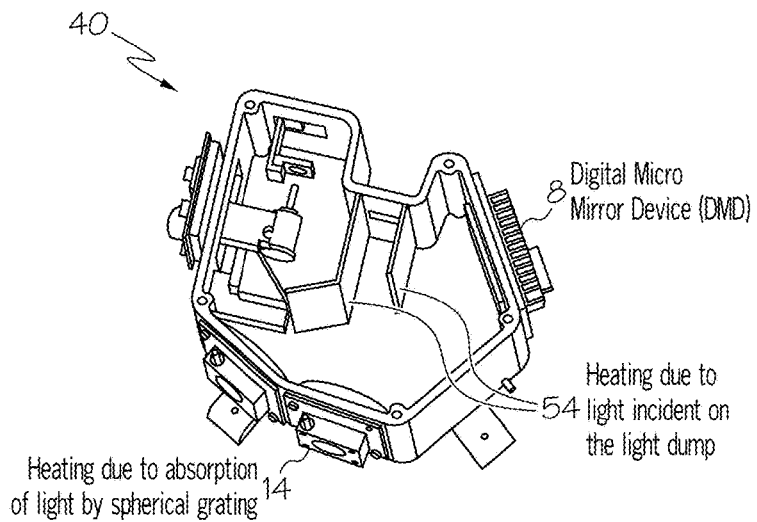
FIG. 43 is an embodiment of the optics bench assembly depicting major heat sources.

The proposed UV-LED detector has a maximum of 11 LEDs and each UV-LED has a rated power of 1 mW. As described herein, the light from each LED is transmitted to the light slit at the optics bench 42 through optical fibers. The amount of heat energy dissipated from the individual optical components can be calculated from those efficiency values. DMD is the most significant heat source in the optics bench assembly 40. The maximum heat power output from the DMD arrays is 1.1 W. Texas Instruments, DLP4710 0.47 1080p DMD 1, no. 1, 2015. Certain heat sources in optics bench are depicted in FIG. 43.

Steady State Thermal Analysis

Figure 44:
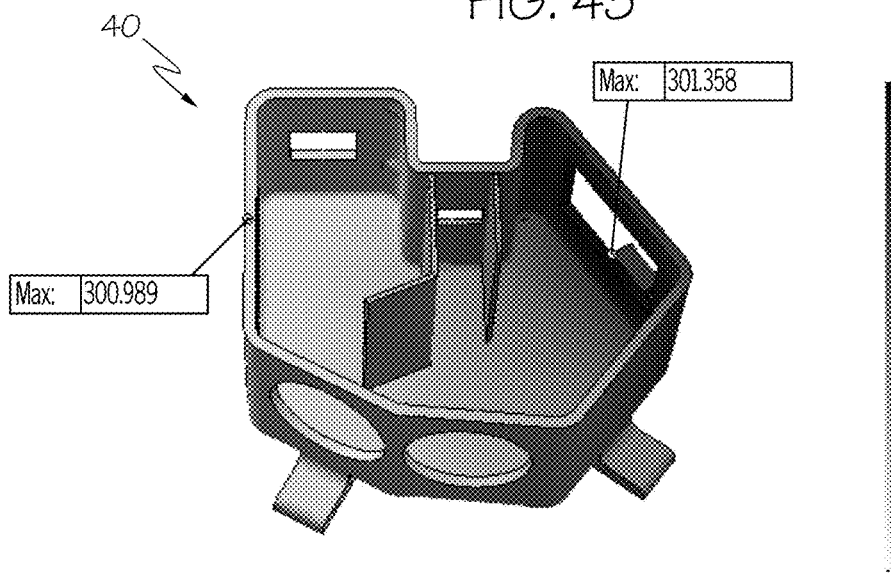
FIG. 44 is an embodiment of the optics bench assembly showing a thermal analysis.

The result of the steady state thermal analysis is shown in FIG. 44. The result indicates that the maximum temperature gradient in the bench does not exceed 0.388K. Since aluminum A356 has coefficient of thermal expansion of 21.4× 10-6 m/mK and the maximum linear dimension of the optics bench is around 261 mm, a temperature difference of less than or equal to 0.388K will lead to differential expansion of less than or equal to $2.167 \times 10^{-6}$ m.

The above results also show that the steady state temperature of the optics bench is close to the ambient air temperature (300K in this case). Further analysis by changing the ambient air temperature shows that the variation in the ambient temperature will lead to variation in the steady state temperature of the optics bench assembly 40. Therefore for the effective functioning of the detector system, it is necessary to decouple the effects of atmospheric temperature variation and maintain the temperature of the optics bench at a constant value. This can be achieved by a well-designed thermal management system.

EXAMPLE VIII

Thermal Management Considerations

Optical components are extremely sensitive to thermal distortion. Since the precision required in optics bench is comparable to wavelength of UV light, even slight thermal distortion can seriously affect the proper functioning of the detector light engine. Thus a thermal management system and robust design strategies are critical in maintaining the dimensional stability of the optics bench and isolating it from ambient temperature variations. The strategies for thermal management in optics bench are: (1) material selection to reduce thermal distortion; (2) assembly design considerations for thermal management; and (3) Detector thermal management system. Thermal Management Considerations during Material Selection.

As discussed herein, for good dimensional stability and minimize distortion due to thermal gradient, a material with low coefficient of thermal expansion and high coefficient of thermal conductivity is selected. Aluminum A356 has a high value of coefficient of thermal conductivity λ (151 W/mK) and not a high coefficient of thermal expansion α (21.6× $10^{-6}$/K) which results in high $$\frac{\lambda}{\alpha}$$

ratio as compared to other metals and polymers. This makes aluminum a preferred and commonly used material for optical enclosures.

Assembly Design Considerations for Thermal Management

The optics bench assembly 40 is designed such that all the individual components have their heat sources (DMD arrays, heat sinks, electronic circuitry and light source) outside the optics bench casing. This allows the external thermal management system to rapidly cool the components. The components such as mirrors, gratings and DMD also heat up due to impinging UV radiation, therefore they are thermally connected to the body of optics bench which in turn offer a larger surface area to be cooled by fans.

Detector Thermal Management System.

Figure 45:
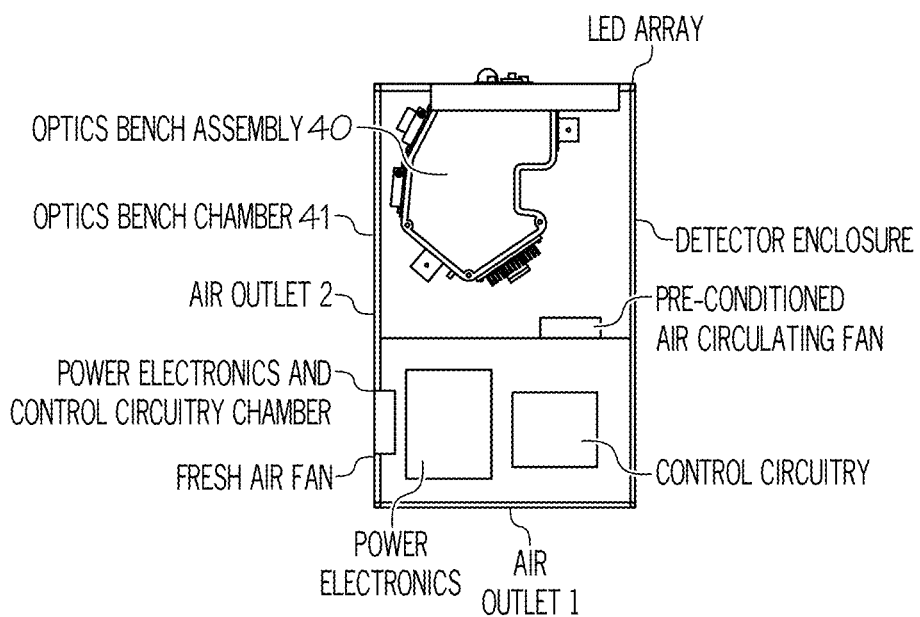
FIG. 45 is an embodiment of a UV-LED detector presented herein depicting the locations of fans and air outlets for thermal management of the detector.

A thermal management of the detector comprises a system of strategically placed fans, heat sinks and air outlets that provides turbulent air flow inside the optics bench assembly 40 for convection cooling. The locations of fans and air outlets are shown in the FIG. 45. The result of the thermal analysis shows that the thermal gradient in the optics bench is insignificant. The major concern is temperature variation due to variation in the ambient temperature. Therefore, the thermal management system can decouple the effects of atmospheric temperature variation and maintain the temperature of the optics bench at a constant value.

The detector module can be divided into two separate chambers; one for the optics bench assembly 40 and other for power electronics and control circuitry. There is no direct inlet of fresh air in the optics bench chamber. This allows isolating the optics bench assembly 40 from variations in the environment. Fresh air is first preconditioned to the right temperature in the power supply and electronic circuitry chamber and then an internal fan circulates the air inside the optics bench chamber. This maintains the temperature of the chamber at a constant value. For better temperature control, a silicone strip heater can be added to the base of the optics bench. The controlled heating by strip heater and cooling by fan, will maintain the temperature of the optics bench within an optimal operating temperature range.

EXAMPLE IX

Manufacturing Process Selection and Considerations

After the optimal wall thickness of the optics bench assembly 40 is determined by engineering analysis, appropriate manufacturing process can be determined according to the selected material, complexity of design, tolerance requirements and cost.

Figure 46:
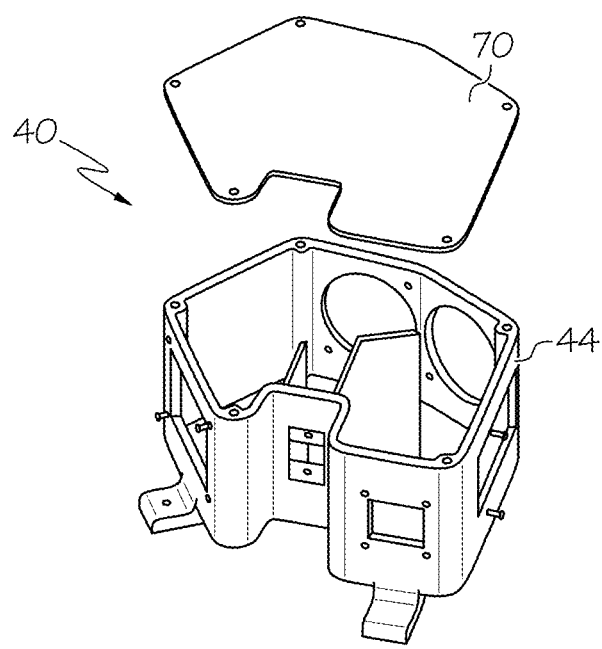
FIG. 46 is an embodiment of the optics bench assembly depicting the optics bench casing and top cover.

In this embodiment, the material selected for the optics bench assembly 40 is aluminum alloy A356. The geometric shape of the optics bench assembly 40 is decided by the optical layout of the detector system. The optics bench casing and cover is shown in FIG. 46. The optics bench casing is an irregular box shape structure with a plate as top cover. The weight of the optics bench casing with top cover as given by the CAD software is around 2.4 kg. The basic function of the optics bench assembly 40 is to precisely mount and locate optical components. The dimensional accuracy required is comparable to wavelength of light. Therefore manufacturing tolerance required in the mounting holes and locating pins are in order of ±0.01 mm. The annual manufacturing volume of the optics bench is expected to be around 1000 units. The design requirements and constraints for optics bench assembly 40 manufacturing are shown in Table 18.

TABLE 18

Design Requirements and Constraints for Optics Bench Manufacturing

| FUNCTION | Optics Bench |
|---|---|
| CONSTRAINTS | Material: Aluminum A356 |
| | Shape: 3D solid, dish shaped, flat plate top cover |
| | Mass: 2.4 kg |
| | Section thickness: 6.35 mm |

TABLE 18-continued

Design Requirements and Constraints
for Optics Bench Manufacturing

| FUNCTION | Optics Bench |
|---|---|
| OBJECTIVE | Minimum tolerance requirement: ±0.01 |
| | Annual production volume: 1000 |
| | Minimize manufacturing cost |
| FREE VARIABLES | Choice of manufacturing process/processes |

Figure 47:
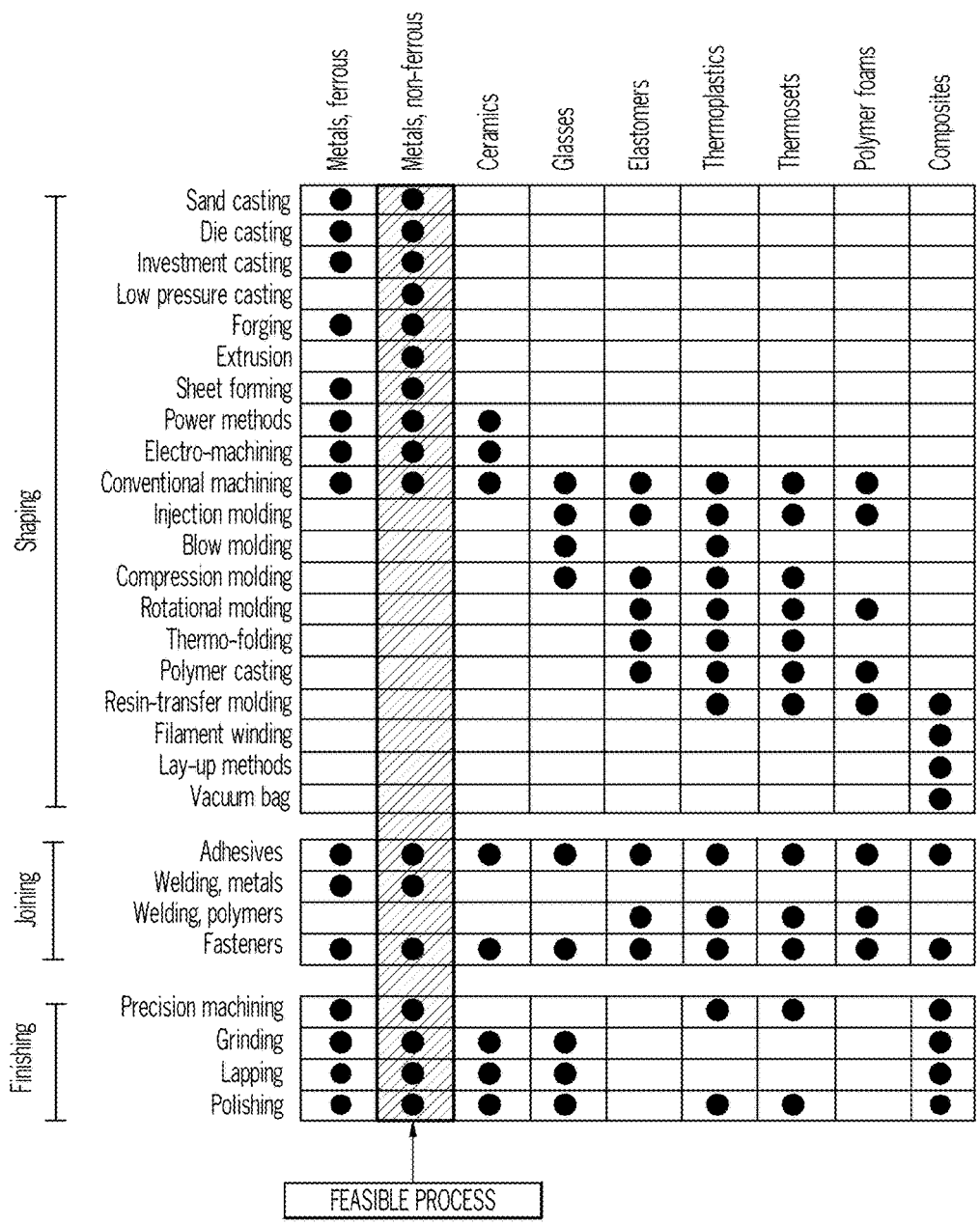
FIG. 47 is a process-material matrix for manufacturing process selection of an embodiment of the optics bench assembly based on material.

As shown by FIG. 47, aluminum can be shaped, joined and finished by a wide variety of processes but for polymer manufacturing processes such as thermoforming, injection molding, blow molding and the like.

Figure 48:
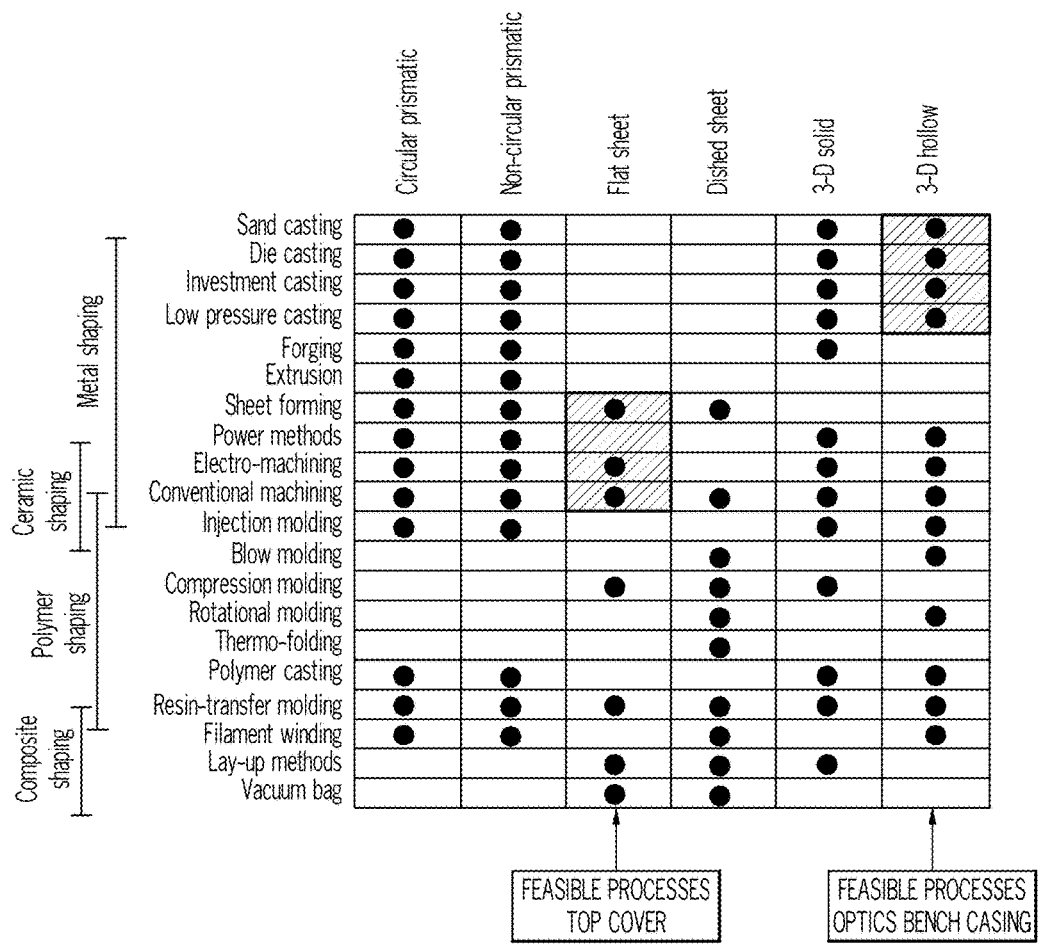
FIG. 48 is a process-material matrix for manufacturing process selection of an embodiment of the optics bench assembly based on shape.

The optics bench casing 44 has a shape of an irregular box with a flat top cover. As shown by FIG. 48, the bottom casing of the optics bench assembly 40 which is form of a 3D hollow solid can be manufactured by sand, die, investment or low pressure casting process. The top flat optics bench assembly cover 70 which is in form of a plate can be manufactured by sheet forming, electro machining or conventional machining process. Advanced manufacturing processes such as water jet, abrasive jet or laser cutting can also be used to cut the top cover profile from aluminum plates.

Figure 49:
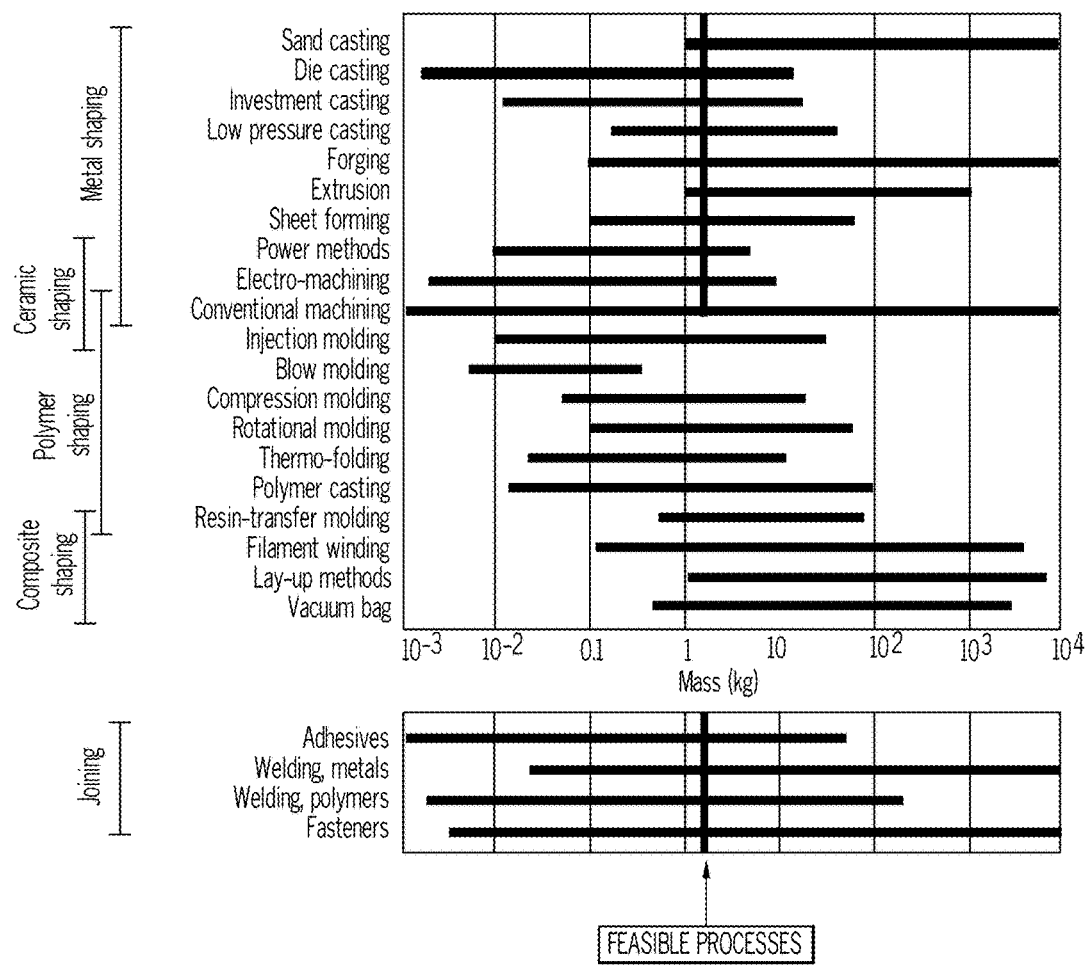
FIG. 49 is a process-mass range chart for manufacturing process selection of an embodiment of the optics bench assembly based on component mass.

The weight of the bottom casing of the optics bench assembly 40 is around 1.8 kg and the weight of the top cover is 0.5 kg. Given the weight, FIG. 49 shows most of the metal shaping process can be used for the bottom casing and for the top cover. Adhesives, metal welding and fasteners are suitable joining processes.

Figure 50:
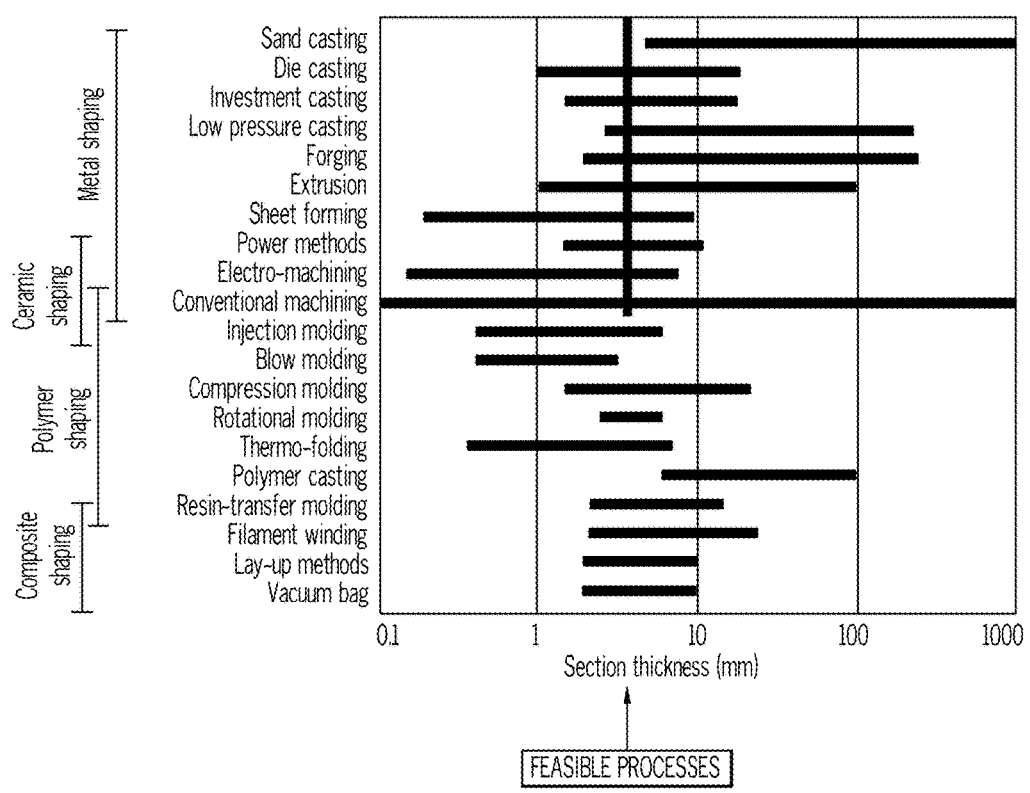
FIG. 50 is a process-section thickness chart for manufacturing process selection of an embodiment of the optics bench assembly based on component section thickness.

The optics bench casing 44 and top cover 70 has a maximum section thickness of 6.35 mm. In FIG. 50, the vertical black line shows all the feasible processes. The sand casting process is not feasible for this level of thickness since surface tension and heat flow limit the minimum section thickness. When only considering the section thickness, all other metal shaping process can be feasible for both bottom casing and the top cover of the optics bench.

Figure 51:
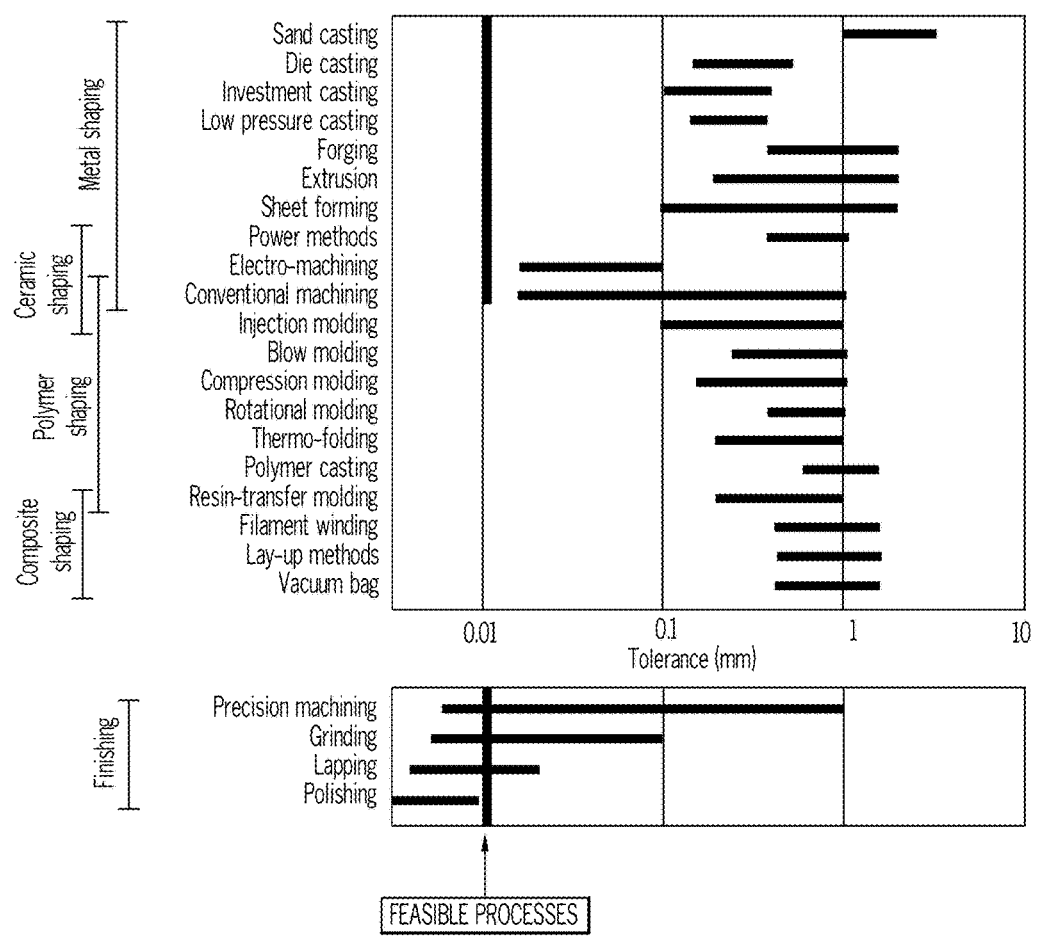
FIG. 51 is a process-tolerance chart for manufacturing process selection of an embodiment of the optics bench assembly based on tolerance requirement.

Achieving precise tolerance level of ±0.01 mm is one of the key constraint in selection of manufacturing process of optics bench assembly 40. As shown in FIG. 51, none of the metal shaping processes are capable of achieving the required tolerance level. Such tolerances can be achieved by finishing processes such as precision machining, lapping, grinding and polishing. Therefore the manufacturing of the optics bench assembly 40 has to be a two-step process. In the first step a near net shape is achieved by metal shaping process such as casting or extrusion followed by precision machining of features such as surfaces, holes, slots and pins, which has tight tolerance requirements.

Figure 52:
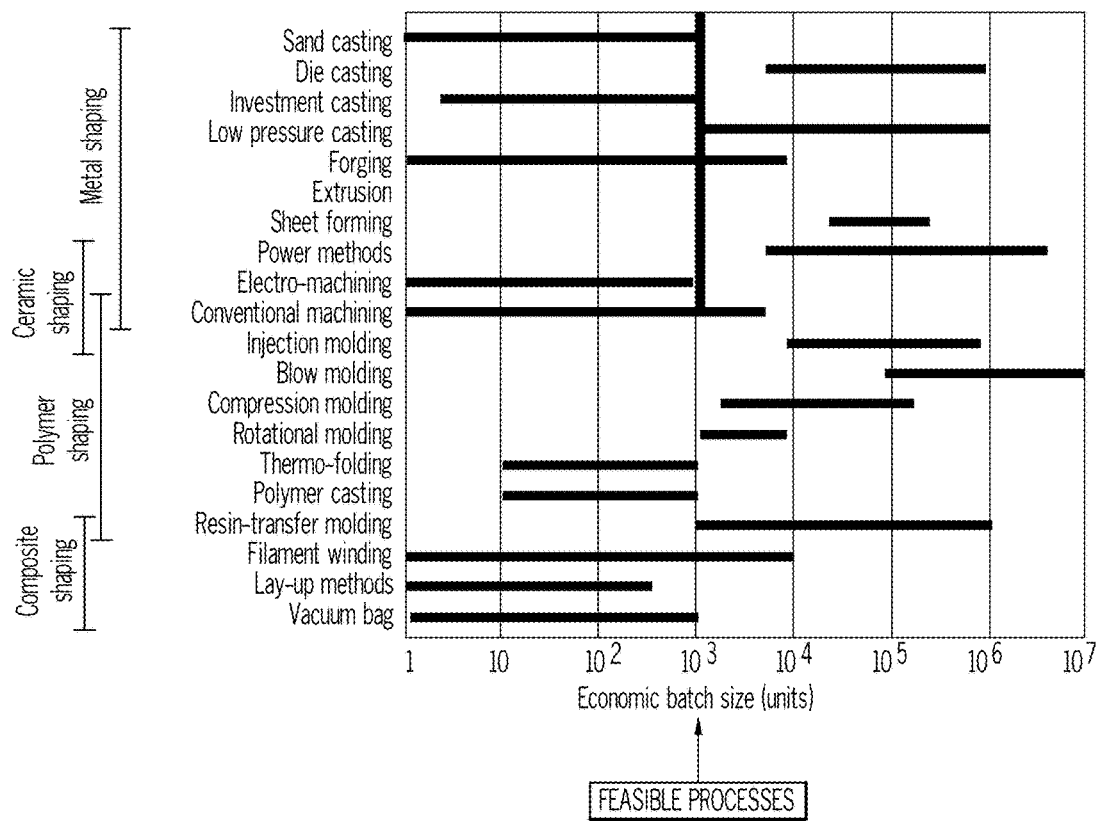
FIG. 52 is an economic batch size chart for manufacturing process selection of an embodiment of the optics bench assembly based on economic batch size.

One of the most important considerations and the final deciding criterion for manufacturing process selection is the cost. Usually, manufacturing cost depends on a number of variables such as tooling, overhead and equipment costs. The effect of all these variables can be captured by a single attribute called economic batch size. Ashby, M. F., *Materials Selection in Mechanical Design Third Edition*, 3$^{rd}$ ed., 2005. It helps in deciding which is the most cost effective manufacturing process based on the number of units of the part that is to be produced annually. The annual lot size of the optics bench assembly 40 is expected to be around a 1000 units. As shown in FIG. 52, for an economic batch size of 1000 units the manufacturing processes feasible for aluminum are sand casting, investment casting, lost foam casting, low pressure casting, forging and conventional machining process. Die casting and powder methods are not feasible manufacturing processes for a lot size of 1000 units.

Based on the analysis from the previous sections, it can be concluded that the best manufacturing process for the bottom casing of the optics bench assembly 40 is casting followed by precision machining. The top cover can be manufactured from stock aluminum sheets by water-jet machining process. Since the high precision and tolerance requirements in the bottom casing of optics bench assembly 40 can be only met by precision machining process, the choice of casting process is dictated by cost and complexity of the part. Since the optics bench geometry is fairly complex, the best suited casting process is lost foam or investment casting process. A high level of dimensional accuracy, good surface finish and near net shapes can be achieved by these processes.

EXAMPLE X

Manufacturing Design of Optics Bench Assembly

Figure 53:
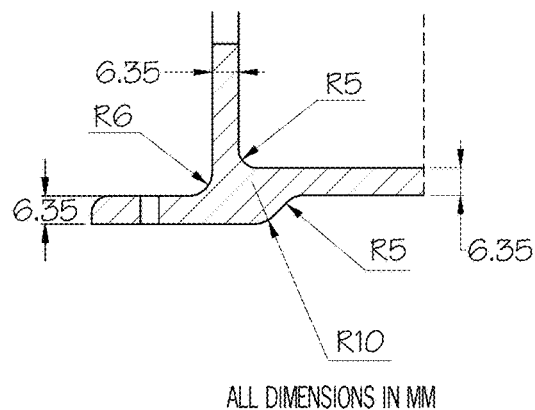
FIG. 53 depicts cross sectional view of an embodiment of the optics bench casing.

While designing the optics bench assembly 40, guidelines for lost foam casting are considered. As shown in FIG. 53, in the optics bench casing design, sharp corners are eliminated by fillet radius and there are no sharp angles. Whenever possible, the wall thickness is kept uniform at 6.35 mm and sharp transitions in the cross-sectional area are avoided Selection of Surface Coating Despite having some good mechanical properties such as good thermal conductivity, good electrical conductivity, good machinability characteristics; aluminum also has some drawbacks such as it is susceptible to oxidization, abrasion and it is relatively soft when compared to other metals. Therefore parts made of aluminum need to be surface coated to mitigate or eliminate the drawbacks, avoid degradation of performance, prevent any deterioration in appearance and increase the service life of the part. In addition to these functional requirements, the coating for the optics bench should absorb any stray light and prevent it from ricocheting off surfaces. Only black colored coatings appear suitable for this application because black objects are good absorber of radiation and blacker the material the more heat it radiates away. Dunbar, Brian, NASA-NASA Develops Super-Black Material That Absorbs Light Across Multiple Wavelength Bands.

Considerations for selecting an optical coating include the type of substrate material, spectral requirements, performance requirements, effects elsewhere in the system, manufacturability, environmental degradation, maintenance and cost. The surface coatings for the optics bench are preferably corrosion resistant, wear resistant, resistant to solvents and chemicals, have high absorption, and low reflectance of a wide range of light from UV to IR resistant to UV degradation. Suitable surface coatings preferably have high thermal stability in wide operating temperature range, high thermal conductivity, and excellent adhesion to aluminum substrate. Areas of electrical contact or that act as a reference surface for mating surfaces for high precision applications may be masked during the coating operation. Methods for surface coating aluminum include anodizing/plating/chemical films, painting, and vapor disposition. Traditional black paints are not suitable for optical applications. Black paints can absorb only 90% of the incident light. Anodizing is a popular surface coating method. Various anodized coating/hardcoat systems are used for UV, visible and IR light attenuation applications which are also compatible with aluminum over a wide spectral range. These coatings have micro protuberances and cavities that give rise to multiple reflections and scattering of radiation from surface irregularities. Yoder, P., *Opto-Mechanical Systems Design*, Fourth Edition, Volume 1: Design and Analysis of Opto-Mechanical Assemblies, Volume 1, vol. 1, CRC Press, 2015. Coatings suitable for the optics bench assembly 40 include low reflectance of light from low UV to high IR range; thin coatings, so it can conform to the sharp edges and enhances compliance with precise part tolerance including a wide range of thermal and vibration stability, highly resistant to UV degradation due to its inorganic nature Protection against Dust, Airborne Contaminants and Humidity Moisture and humidity have a damaging effect on the integrity and performance of optical equipment by condensing on optical surfaces or by corroding optical components. Other detrimental effects of water as a liquid or vapor inside optics bench assembly 40 include; acceleration of stress-related fracture propagation and obstruction of transmitted or reflected radiation due to absorption or scatter. High salt content in the moisture, especially in coastal areas, can accelerate the corrosion and failure of coating on optical and structural components.

Common sources of contamination of optical surfaces are fingerprints, oil from skin, smoke and dust. The contaminants reduce performance by reducing light transmission and intensity by scattering, reflection and absorption. Another typical contaminant usually found in tropical countries with warm climate and high humidity, is growth of localized deposits and films of fungus or molds. The microscopic spores of these microorganisms are ubiquitous and can germinate and grow on even thoroughly cleaned glass surfaces. These organic contaminants degrade optical performance by introducing scatter or can permanently damage optical surfaces by etching patterns into the material. Yoder, P., *Opto-Mechanical Systems Design*, Fourth Edition, Volume 1: Design and Analysis of Opto-Mechanical Assemblies, Volume 1, vol. 1, CRC Press, 2015.

Figure 54:
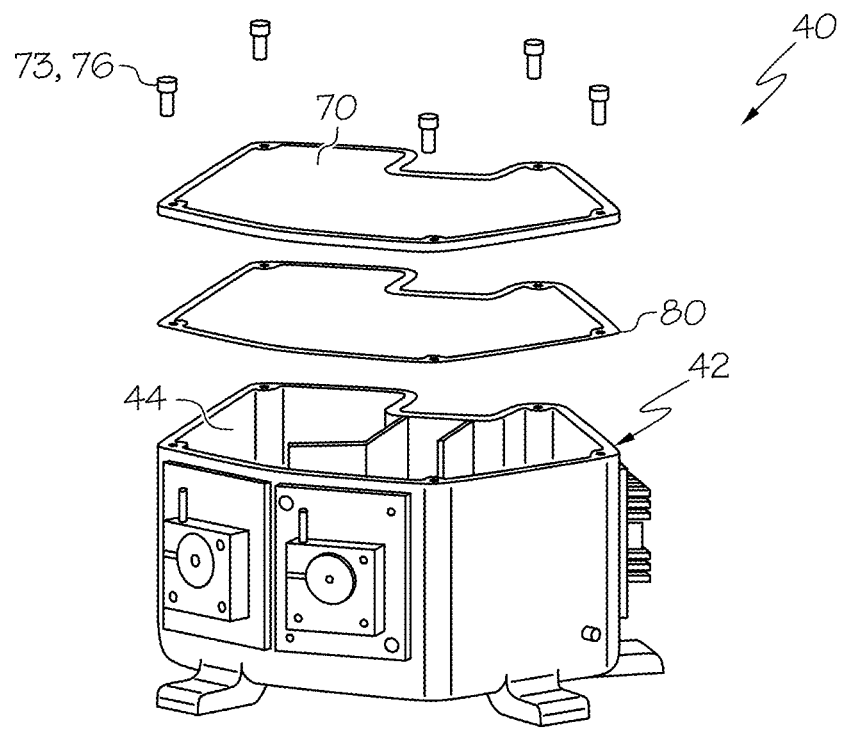
FIG. 54 shows a sealing gasket in an embodiment of the optics bench assembly.

There are many features in the optics bench assembly 40 design which can isolate the optical components from dust, humidity and airborne contaminants. The isolation and protection is at two levels, the detector module level and the optics bench assembly 40 level. First, the detector has filters of appropriate size at the fresh air inlet ports. The filters prevents large to medium size contaminants and dust particles from entering into the detector enclosure. Second, the thermal management system is designed so the detector chamber is pressurized by blowing air into the chamber keeping dust out of the system. Third, to counter humidity and moisture the optics bench chamber is sealed watertight by using elastomeric gaskets between the optics bench casing 44 and the cover 70. As shown in FIG. 54, the gasket 80 is shaped to the profile of the opening of optics bench. The gasket material can have a high chemical and UV resistance. Fluoroelastomer gaskets have high chemical inertness and outstanding UV resistance, and are suited for the above application. Fourth, dry gas purging is frequently used to create low dew points within sensitive equipment. The newly built optics bench assembly 40 can be purged of internal gaseous and fluid contaminants by using dry gas such as nitrogen or helium. The optics bench chamber can be then evacuated and backfilled with same fresh dry gas.

Figure 55:
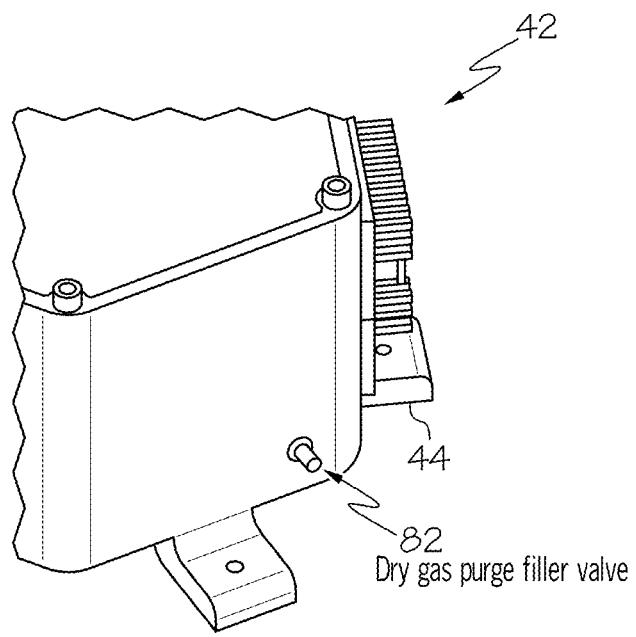
FIG. 55 shows a dry gas purge filler valve in an embodiment of the optics bench casing.

During periodic maintenance or servicing, the optics bench chamber 41 should be evacuated and re-pressurized with dry gas. As shown in FIG. 55, the optics bench casing 44 has a dry gas purge filler valve 82 which is used to purge or pressurize the optics bench chamber 41. Repeated and unnecessary cleaning of the optics bench is not recommended as cleaning unavoidably degrades the thin film coatings on optical instruments. When cleaned, only approved procedures, materials and solvents compatible with optical instruments can be used.

The performance of the optics bench assembly 40 is improved in a temperature controlled and stable environment. Therefore, the end users should be encouraged to operate the optics bench assembly 40 in lab environment with temperature and humidity controlled by HVAC systems for better performance and consistent results.

Error Budgeting

Figure 56:
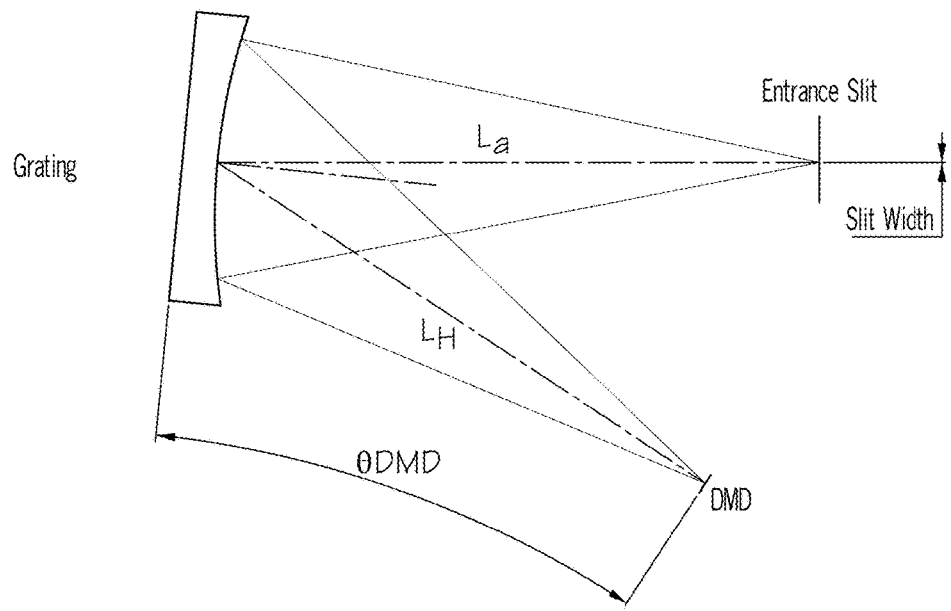
FIG. 56 is a schematic showing key dimensions of an optical layout and orientation of DMD with respect to a spectral plane of grating useful in an error budget analysis.

Error budgeting is the practice of assigning permissible error to various sources on the basis of functionality, feasibility and cost. It is useful for predicting the accuracy and repeatability of the components and optics bench assembly 40 to determine the appropriate tolerances that can be specified on the optics bench assembly 40 to provide adequate performance. In the optics bench assembly 40, the single most important measure of performance is the resolution. The major sources of error in the optics bench assembly 40 which affect the resolution are variations in: (1) the entrance slit width ($\Delta w_{slit}$); (2) the entrance slit 12 and the grating 14 ($\Delta L_\alpha$); the distance between the DMD 8 and the grating ($\Delta L_H$) and the angular alignment between the DMD and the spectral plane of the grating ($\Delta \theta_{DMD}$). The optical layout depicting the distances $L_\alpha$ and $L_H$, and the orientation of DMD 8 with respect to the spectral plane of grating, is shown in FIG. 56.

The variation in entrance slit width is wholly the result of manufacturing variability. Variation in distance between the entrance slit 12 and grating 14 and between the DMD 8 and grating 14 could be caused by manufacturing variability, thermal expansion and vibration disturbances. The vibration induced error is minimized by the use of vibration isolators as described herein, and is insignificant compared to the errors due to manufacturing variability and thermal expansion. Therefore it is not considered in the error budget. The angular misalignment of the DMD can mainly be attributed to the manufacturing variability.

Equations 47-50 give expressions for each of these variations in terms of the physical sources of the error. The maximum variation in the entrance slit width $\Delta w_{slit}$ and its relation with the bilateral manufacturing tolerance $t_{slit}$ is given by Equation 47.

$$\Delta w_{slit} = t_{slit} \tag{47}$$

The maximum variation in the angular alignment between the DMD and the spectral plane of the grating $\Delta\theta_{DMD}$ and its relation with the bilateral angular manufacturing tolerance $t_{\theta DMD}$ is given by Equation 48.

$$\Delta\theta_{DMD} = t_{\theta DMD} \tag{48}$$

The maximum variation in the distance between the slit and the grating $\Delta L_\alpha$, and its relation with the bilateral manufacturing tolerance $t_\alpha$ and thermal expansion is given by Equation 49, where $\alpha_{Al}$ is coefficient of thermal expansion of aluminum A356 and $\Delta T$ is the maximum allowable change in the temperature of the optics bench.

$$\Delta L_\alpha = t_\alpha + L_\alpha \alpha_{Al} \Delta T \tag{49}$$

The maximum variation in the distance between the DMD and the grating $\Delta L_H$, and its relation with the bilateral manufacturing tolerance $t_H$ and thermal expansion is given by Equation 50.

$$\Delta L_H = t_H + L_H \alpha_{Al} \Delta T \tag{50}$$

The resolution sensitivity as described herein is given by Equation 51, where NA is the numerical aperture, $d_l$ is the linear dispersion of the grating and $L_{DMD}$ is the length of the DMD array.

$$\frac{\partial R}{\partial L_\alpha \partial L_H \partial \theta_{DMD} \partial w_{slit}} = \qquad (51)$$
$$2NAd_l(\partial L_\alpha + \partial L_H) + \partial w_{slit}\partial_l + \partial \theta_{DMD}(L_{DMD}NAd_l)$$

Substituting expressions for the variations given in Equations 47-50 into Equation 51, we get the resolution sensitivity to manufacturing tolerances and variations in temperature, as shown in the Equation 52.

$$\frac{\partial R}{t_\alpha t_H t_{\theta DMD} t_{sw}} = \qquad (52)$$
$$2NAd_l(t_H + t_\alpha + \alpha_{Al}\partial T(L_H + L_\alpha)) + t_{slit}d_l + t\theta_{DMD}(L_{DMD}NAd_l)$$

The values of NA, dl, LDMD, LH and Lα are determined by the optical design of the detector as shown in Table 19.

TABLE 19

Numerical Values of NA, $d_l$, $L_{DMD}$, $L_H$ and $L_\alpha$

| NA | $d_l$ (nm/mm) | $L_H$ (mm) | $L_\alpha$ (mm) | $L_{DMD}$ (mm) |
|---|---|---|---|---|
| 0.21 | 24.3 | 131.45 | 137.1 | 5 |

The resolution of the optical system is the sum of the inherent resolution $R_o$, given by the micromirror pitch of the DMD, and the increase in resolution $\partial R$ due to error, as shown in Equation 53.

$$R = R_o + \partial R \qquad (53)$$

For optical design, inherent resolution is 0.135 nm. The objective of error budgeting is to find the optimal range of tolerances which will keep the error within specified limits. The target resolution of the optical system is 1 nm. Therefore, as Equation 53 shows, $\partial R$ can be less than or equal to 0.865 nm, which is the maximum permissible increase in resolution due to errors. The sensitivity of resolution with respect to manufacturing tolerances and change in temperature is derived from Equation 52 and depicted in FIG. 57. The error sources to which the resolution is not as sensitive are assigned looser tolerances to allow more flexibility in manufacturing and to reduce cost. The error sources which drastically effect the resolution even with small changes are assigned tighter tolerance values so that the functionality of the detector is not effected.

Figure 57:
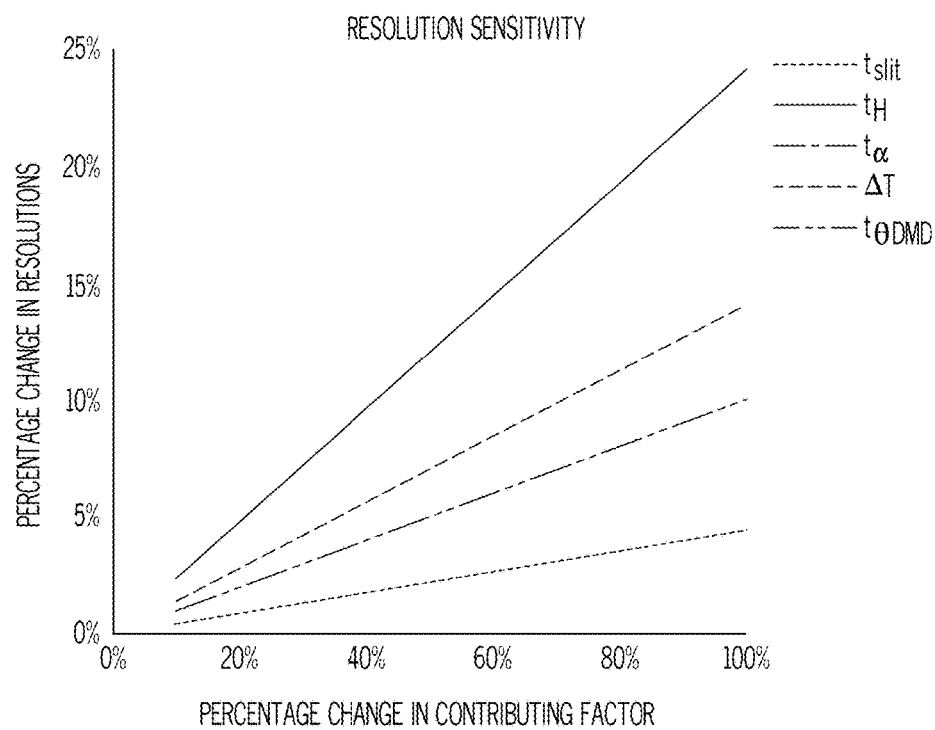
FIG. 57 shows resolution sensitivity with respect to manufacturing tolerances and change in temperature in the optical layout.

As shown in FIG. 57, the resolution is most sensitive to tH and tα. Both have similar effect on the resolution and thus overlap in FIG. 57. Therefore, the tolerance assigned to these factors can be tight, as a large variability will severely affect the resolution. After $t_H$ and $t_\alpha$, the resolution is most sensitive is the temperature change $\Delta T$. As a result, a thermal management system will be required to keep the temperature within the prescribed window. The resolution is not sensitive to $t_{slit}$ and $t_{\theta DMD}$, so conventional manufacturing tolerances are sufficient for these factors.

Using Equations 52 and 53, the tolerance values are budgeted keeping in view the target specifications, resolution sensitivity, the design, capabilities of manufacturing processes and expected operating conditions. Table 20 shows the error budget for the optics bench to achieve the target resolution of 1 nm for the optical system of the detector.

TABLE 20

Error Budget for the Factors Affecting Resolution

| $R_o$ (nm) | $\Delta R$ (nm) | $t_H$ (mm) | $t_\alpha$ (mm) | $\Delta T$ (K) | $t_{slit}$ (mm) | $t_{\theta DMD}$ (degree) |
|---|---|---|---|---|---|---|
| 0.135 | 0.835 | ±0.025 | ±0.025 | ±3 | ±0.002 | ±0.25 |

As shown in Table 20, tolerances $t_H$ and $t_\alpha$ are in the range ±0.025 mm. The angular misalignment of the DMD can be within ±0.25°. The entrance slit as specified by the optical design has a width of 40 microns. For this slit width a tolerance level of ±2 microns is specified by the manufacturer. The temperature variation can be kept within ±3K by a robust thermal management system. A combination of precision machining and calibration can be used to achieve the desired level of resolution and minimize the error. The optics bench casing can be manufactured using the lost foam investment casting process. The typical linear tolerances with lost foam investment casting are 0.005 mm/mm. The maximum linear dimension of optics bench is around 250 mm, so the tolerances on the casted bench will be around ±1.25 mm. This is well above the desired tolerance of ±0.025 mm.

Therefore, casting can be followed by precision machining. To accommodate post-machining steps, sufficient machining allowance can be incorporated in the design of the optics bench casting. The tolerances achieved by machining with a 5 axis milling machine range from ±0.01 mm to ±0.005 mm. Ashby, M. F., *Materials Selection in Mechanical Design Third Edition*, 3rd ed. 2005; Woldman, N. E. and Gibbons, R. C., *Machinability and Machining of Metals*, McGraw-Hill, 1951. The tolerances near the lower limit are more common and the tighter tolerances can be achieved by high precision, high cost machines. Therefore, post machining the optics bench with tolerances of ±0.025 mm, can be achieved. However this level of tolerance will come at an increased cost. If cost is a constraint, tolerances in machining can be relaxed by compromising on the resolution of the optical system. The order of operations for machining can be as follows: (1) the optics bench assembly 40 is clamped with the top opening facing downwards; (2) the four feet and their mounting holes are machined; (3) the bench is fixed to a rotary table with precision pins through the mounting holes and the mounting feet clamped against the table; and (4) the machining of critical surfaces and holes can be carried out with this setup on 5-axis mill.

Figure 58:
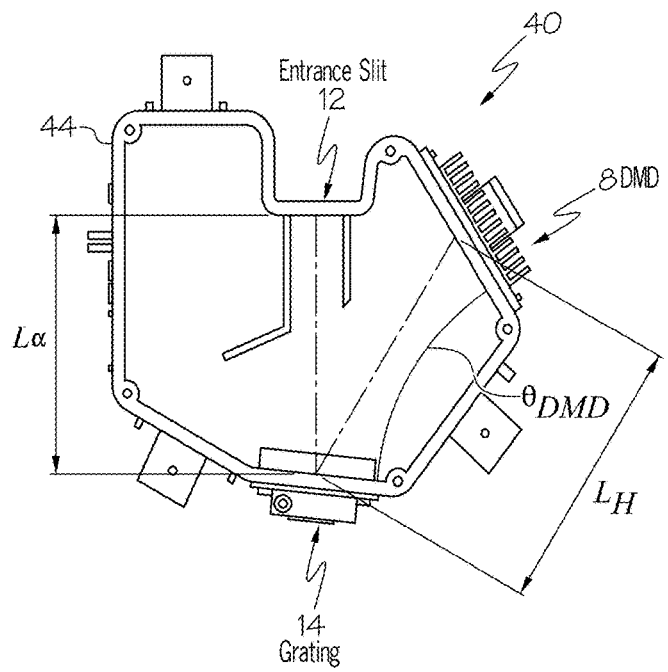
FIG. 58 is a schematic of an embodiment of the optics bench assembly with dimensions to be calibrated.

After machining, the optics bench can be assembled. The manufacturing tolerances for angular orientation are well within the design specifications. Using an oversized DMD will allow much of the calibration to take place automatically. To achieve the required tolerances for $L_H$ and $L_\alpha$, the optical system can be manually calibrated. Therefore, calibration effort and time should be focused on the linear distances $L_H$ and $L_\alpha$ as shown in FIG. 58.

Figure 59A:
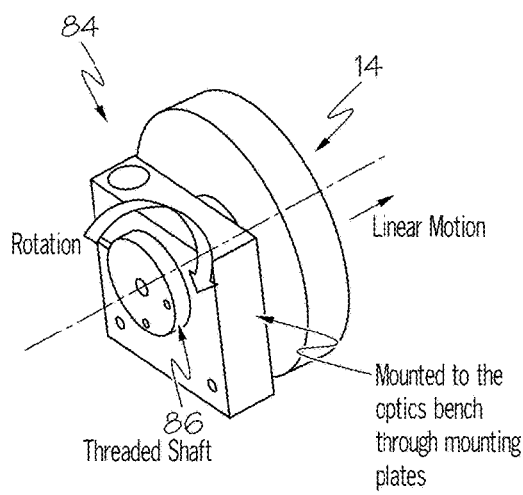
FIGS. 59A and 59B show the calibration for a spherical grating.
Figure 59B:
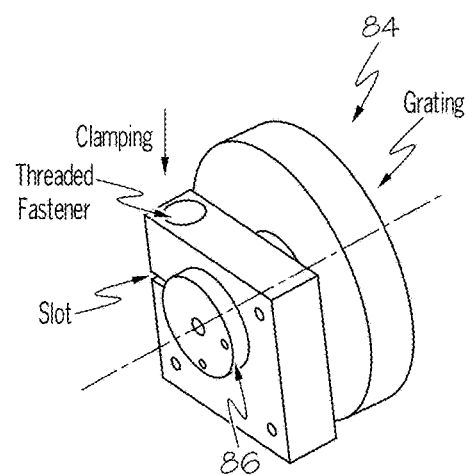

The calibration mechanism 84 is shown in FIG. 59. A threaded shaft 86 will allow the grating 14 to move linearly and adjust the distance $L_H$ and $L_\alpha$. The angle between the axis of the grating 14 and $L_H$ and between axis and $L_\alpha$, are small. Therefore, linear movement along the grating axis will result in 89% and 99% movement along $L_H$ and $L_\alpha$ respectively. After achieving the desired resolution, the grating can be locked down to the accurate location using the clamping mechanism or threaded fastener 88. The above proposals need to be tested and validated by prototyping and extensive testing.

EXAMPLE XI

Prophetic Prototype of Optics Bench Assembly

Figure 60A:
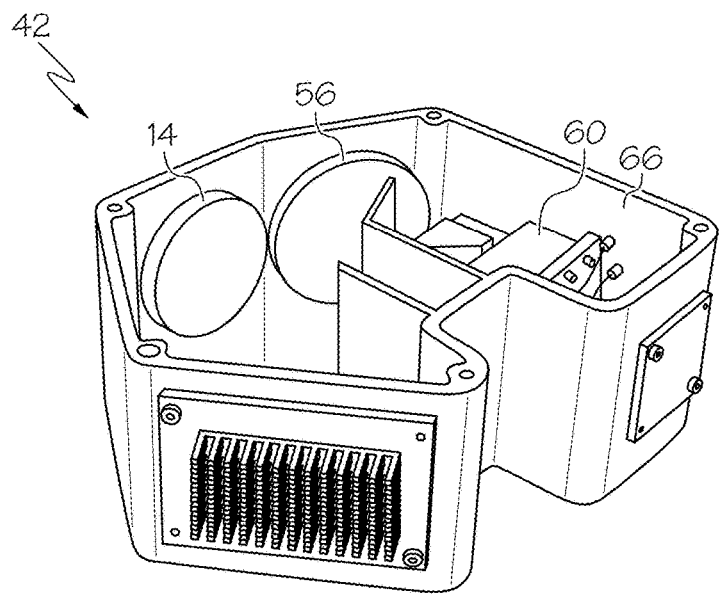
FIGS. 60A and 60B show a prototype of the optics bench assembly.
Figure 60B:
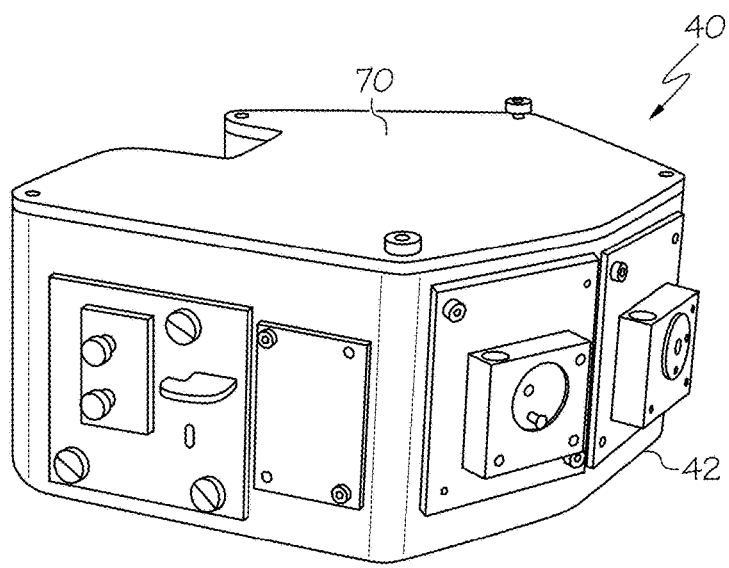

A looks-like physical prototype of the optics bench assembly 40 was 3D printed using a Fused Deposition Modeling (FDM) process to check any issues during assembly and service. The pictures of the prototype are shown in FIG. 60. The optics bench casing, cover and mounting brackets were all 3D printed. All other off the shelf and custom made optical components such as the mirror 56, grating 14, photodiodes 62,64, flow cell 66, light entrance slit 12 and beam splitter 60 were mounted on the printed parts. During assembly of components no major issues were observed. There was no clash of assembled components and assembly process was seamless. The slots in the optics bench 42 had sufficient clearance to allow unobstructed assembly path for optical components for entry in the optics bench 42 without scratch or damage. There was also unobstructed access to the tools used for assembly. But utmost care needs to be taken during the assembly process and it can be carried out in a clean room with dry environment to prevent contamination of optical components.

The mechanical design of the optic bench assembly is based on the optical layout of the UV-LED based Liquid Chromatography detector. The optic bench assembly is broken down into smaller subassemblies containing optical and structural components. The subassemblies are attached to the optics bench casing using fasteners and aligned and located using precision machined locating pins. All the subassemblies are designed to be independently replaceable to facilitate serviceability. The assembly is also designed so the thermal heat sources of the opto-electrical components are kept outside the optics bench casing.

Aluminum A356 was found to be a suited material for optics bench assembly 40 to minimize vibration sensitivity, thermal distortion and deformation during impact loading. The material is also resistant to UV degradation, easily available and is also cost effective. After drop test and vibration analysis, it was found that a uniform wall thickness of 6.35 mm (0.25 inches) increases the stiffness and natural frequency of the optics bench far above the disturbing frequencies and minimizes the stress during drop test. The weight of the assembly falls under acceptable limits.

To isolate the assembly from vibration disturbances and protect the optical components during shock loading, vibration and shock mounts were incorporated in the assembly. Thermal analysis showed that the thermal gradient in the optics bench due heat generated by opto-electrical devices and radiation absorption is not significant. But it was found that the optics bench temperature is sensitive to variation in the ambient temperature and thus a thermal management system is needed to decouple the effects of environmental temperature variation and maintain the temperature of the optics bench at a constant operating temperature.

Based on the selected material, complexity of design and functional requirements, lost foam casting or investment casting followed by precision machining and water jet cutting of aluminum plate was a suited manufacturing process for both the optics bench bottom casing and top cover. Coating the optics bench with Martin black dye anodized coating or vacuum deposited coating with Acktar optical Black™ prevents corrosion and wear, and also to absorb stray UV radiation. Features such as sealing the bench watertight using fluoroelastomer gaskets and dry gas purging to protect the optical components from contaminants, dust and moisture, were also incorporated.

The Diversity of Applications for the Detector

Figure 61:
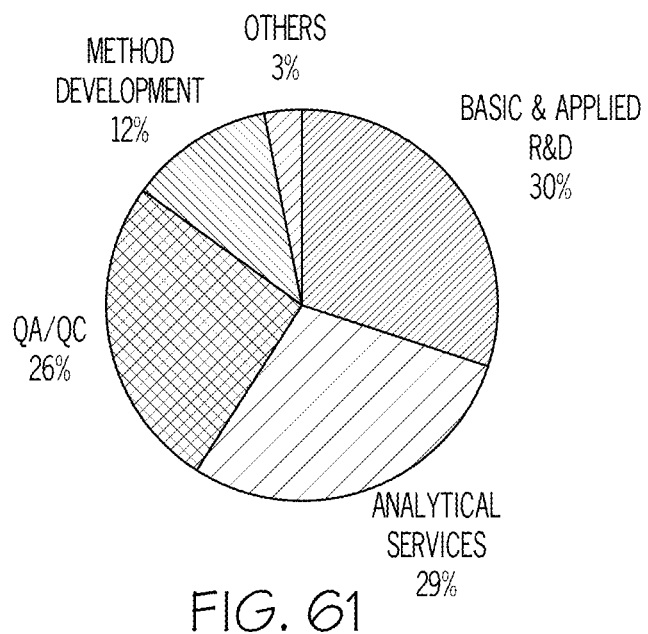
FIG. 61 provides a pie chart showing market demand of HPLC in 2013.

FIG. 61 provides a pie chart of 2013 market demand for HPLC systems. The chart was generated in part with data acquired from the U.S. Pharmacopeial Convention ("USP") via the marketing division of a leading liquid chromatography equipment manufacturer. The USP is a scientific non-profit organization that sets the standards for the identity, strength, quality and purity of medicine, food ingredients, dietary supplements and the like to be manufactured, distributed and consumed worldwide.

USP undertakes is to develop and maintain monographs for various medications, food ingredients, dietary supplements, etc. A monograph is a standard which details a substance and provides its name; its definition; packaging, storage and labeling requirements; and all the information on tests required to ensure that the substance is of appropriate strength, quality and purity States, et al., USP FACT SHEET, *USP Standards: Monographs (Written Standards) What is a Monograph?* (2008). Key information in these monographs includes a specific wavelength that is recommended to detect the substance (also referred to herein as a "constituent" or a "compound").

Figure 62:
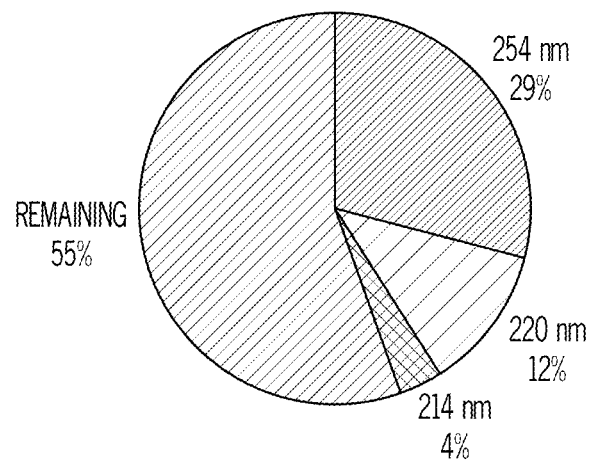
FIG. 62 provides a pie chart showing percentage of monographs with liquid chromatography broken down by different wavelengths.

As shown in FIG. 62, data shows that there are a number of testing methods that utilize specific wavelengths, e.g. nearly 30% of the registered LC methods are use a wavelength of 254 nm. A number of such preferred wavelengths exist and use of such wavelengths is most often established in standard tests for various substances. On the other hand, increasingly, companies are more interested in the response of new and unknown substances to the whole spectrum of light (UV-visible) and require more flexibility in wavelength selection. Current UV absorption detectors are generally designed for the wavelength range of 180 nm to 350 nm and many substances are known to absorb light in this range Scott, R. P. W., *Liquid Chromatography Detectors*, Journal of Chromatography Library, $1^{st}$ ed., vol. 11, Elsevier, 1986. On the basis of this gathered information and data, we identified three customer segments for the detector described herein as shown in Table 21.

TABLE 21

Proposed Customer Segmentation for the Detector

| S. No. | Customer Segment Requirment |
|---|---|
| 1 | Single Wavelength Requirement |
| 2 | Wavelength varying capability requirement in the UV range |
| 3 | Wavelength varying capability requirement in the UV-Visible Range |

Proposed Configurations for the Detector

Considering the customer segments, three configurations for the detector and estimated market share are provided in Table 22 below.

TABLE 22

Identified Configurations for the Detector

| S. No. | Configuration | Estimated Market Share |
|---|---|---|
| 1 | Single wavelength configuration, with ability to change wavelengths if needed | 50% |

TABLE 22-continued

Identified Configurations for the Detector

| S. No. | Configuration | Estimated Market Share |
|---|---|---|
| 2 | UV range scanning capability | 40% |
| 3 | UV-visible range light scanning capability | 10% |

For estimating the market share, we theorize that 90% of the QC/QA and the analytical service segment will be interested in the single wavelength configuration. Of the remaining customers, we surmise that 80% will have their demand met by the UV range scanning capability detectors and the rest will want the UV-visible range scanning capability. The estimated market share gives some indication of the possible sales scenario for the detectors.

Existing UV Light Detectors

Figure 63:
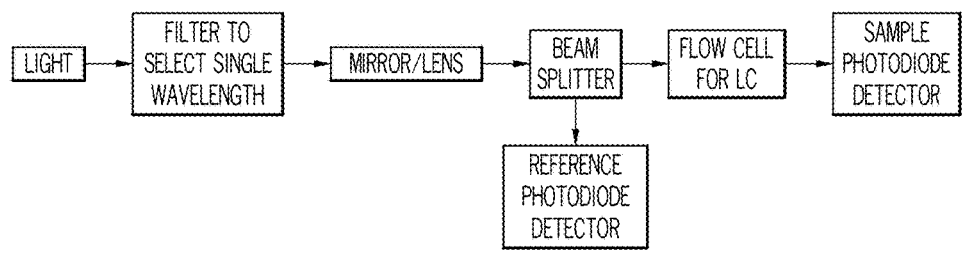
FIG. 63 is a schematic of a fixed wavelength detector.
Figure 64:
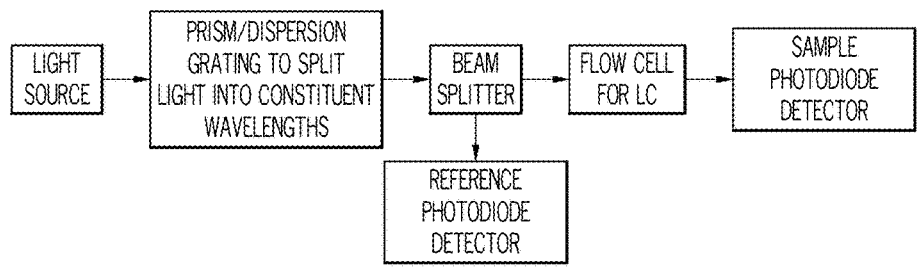
FIG. 64 is a schematic of a scanning type detector.

A fixed wavelength detector is relatively simple in design and construction, and the schematic for the light path in such a detector provided in FIG. 63. For the scanning detector, a basic schematic depicting its working is shown in FIG. 64. In this type of detector, the prism/dispersion grating is moved via a motorized mechanism for the purpose of selecting different wavelengths. However because of the inertia of the prism/grating and motorized mechanism, it is not to switch between wavelengths at high speeds.

Figure 65:
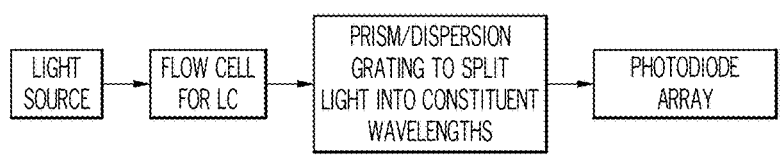
FIG. 65 is a schematic of a photodiode array detector.

For the photodiode array detector, the basic schematic is shown in FIG. 65. This detector appears to be the more costly of UV absorption detectors available in the market, with the key cost coming from the photodiode array.

Current Light Sources Used in UV detectors

As described herein, light sources for use with UV-Visible Light detectors for liquid chromatography have evolved over time. The earliest sources were metal-vapor discharge lamps, which produced a discrete spectrum. Common is the mercury-vapor lamp, which produces a peak wavelength at 253 nm and considered a legacy wavelength as it serves as the basis for a number of current chromatographic methods. Because these lamps had a discrete spectrum, they were favored in the construction of the fixed wavelength detectors. These are now superseded by gas discharge lamps and incandescent lamps, both of which produce a continuous spectrum and are used in scanning and photodiode array type detectors.

UV LEDs and Implications for Detector Architecture

The detector 4 described herein can use high powered UV LEDs as a light source 50. High power LEDs (in the milliwatt and higher range) emitting light in the near-ultraviolet range (300 to 400 nm) are currently available. They are manufactured by depositing Gallium-Nitride or Aluminum-Gallium-Nitride on a sapphire substrate. Deep UV LEDs with AlN—AlGaN based LEDs have already been demonstrated at wavelengths of 210 nm to 360 nm Hirayama, H., et al., *Development of 230-270 nm AlGaN-Based Deep-UV LEDs*, Electron. Commun. Japan, Vol. 93 (2010). However, this type of LED has considerably low efficiencies compared to traditional visible light LEDs. By using metal-organic chemical vapor deposition methods to grow high quality AlN buffers on sapphire substrates, LEDs at 261 nm and 227.5 nm with power 1.65 mW and 0.15 mW respectively were demonstrated. Id.

Figure 66:
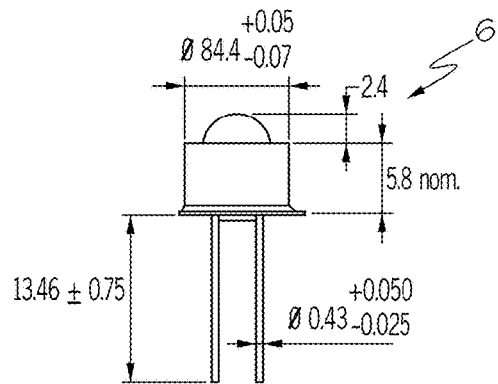
FIG. 66 shows an exemplary UV LED.

High power deep UV LED's are a relatively new product. The deep UV LEDs use AlN as the substrate itself and have an optical output of 0.5 mW or 1 mW. Because of the similarity of the material which results in lower density of dislocations, AlGaN UV LEDs grown on low density bulk AlN exhibit distinct improvements in light output and thermal management. Ren, Z., et al., *Heteroepitaxy of AlGaN on Bulk AlN Substrates for Deep Ultraviolet Light Emitting Diodes*, Appl. Phys. Lett., Vol. 91, No. 5, 90-92 (2007). Deep UV or UVC LEDs, as shown in FIG. 66, in peak wavelengths from 250 nm to 280 nm are currently available. However, because UV LEDs are a developing technology, these LEDs will play a more influential role in determining product architecture, especially modularity.

Figure 67:
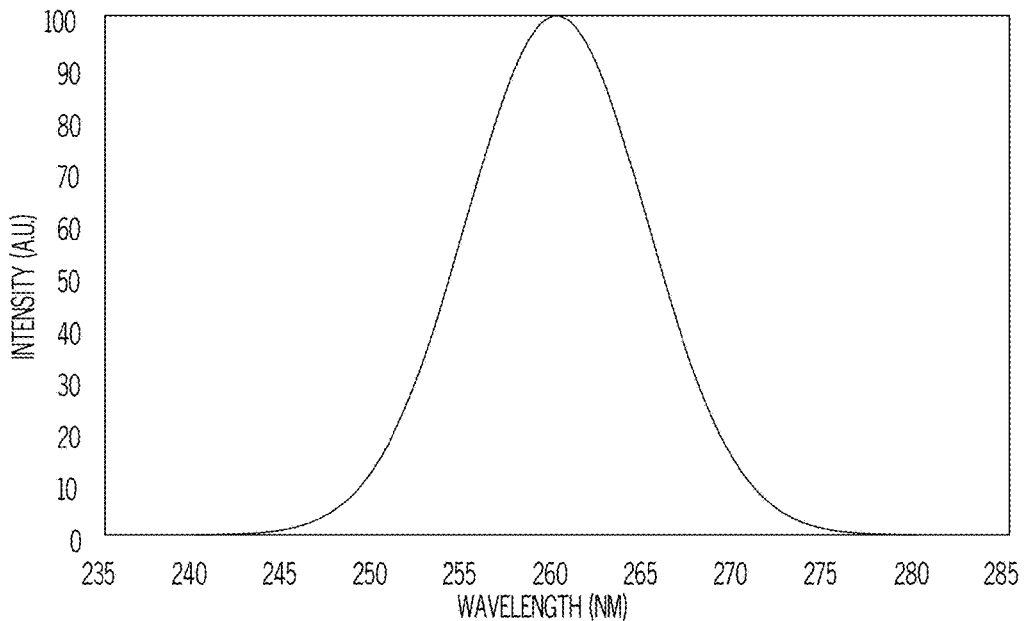
FIG. 67 shows spectral distribution of a UV LED with maxima at 260 nm.

While looking at the product architecture for the detector, a key aspect in LED usage is their limited range of wavelengths as compared to the deuterium UV lamp, making this a technological constraint. The half intensity range for these LEDs is essentially +/−6 nm from the peak wavelength of the LED, so a single LED would cover an band of 12 nms. As shown in FIG. 67, the approximate spectral distribution of a UV LED whose peak wavelength is 260 nm. The UV LEDs are also considerably smaller than UV lamps. They can be approximated as a cylinder with diameter 9 mm and height 6 mm. Crystal IS, *High Performance UVC LEDs for Instrumentation*.

The deep UV LED technology is currently at a nascent stage of its lifecycle and is expected to mature for the next few years. From a cost perspective, while the current iterations of the LEDs are expensive, they are expected to become cheap as the technology is established and mass production becomes the norm.

These two aspects: (1) the short spectrum range; and (2) the current state of the UV LED technology should be considered when designing the architecture for the detector 4. These two considerations move towards a modular approach for UV LEDS as a component in the detector 4. UV LEDS meet the criteria for modularity as described herein.

Optical Fibers for UV LEDs and Implications for Detector Architecture

The use of optical fibers as a light delivery mechanism allows for flexibility in the product architecture. With optical fibers, there is less need to place the light source 50 close to the remaining optical elements, as the fiber can easily route the light to them from the source.

For UV light applications down to the wavelengths of 200 nm, optical fibers made by using slica-glass as the core material and tetrafluoroethylene-hexafluoropropylene copolymer or methylpolysiloxane as the sheath material are appropriate. Such optical fiber systems are optically transparent between 200 nm to 2200 nm range with the only exception being at an absorption band at 1400 nm. These fibers are also thermally stable upto temperatures of 250° C. and show no loss of transmission efficiency. Dislich, H., et al., *Light Guide Systems for the Ultraviolet Region of the Spectrum*, Angew. CHEMIE Int. Ed. English, Vol. 12, No. 6, (1973).

Digital Micromirror Device

Figure 68:
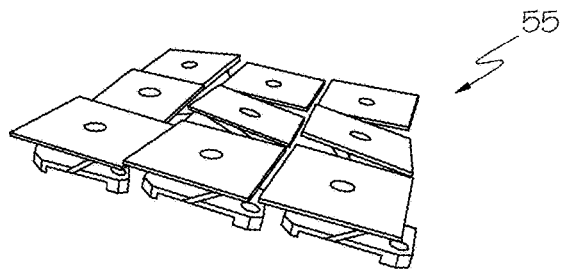
FIG. 68 depicts an embodiment of a digital micro-mirror array.

As described above, the DMD is essentially a light modulator, made up of an array of micro mirrors, each of which can be moved independently. The device has a memory cell below the mirror array where data is loaded to control the tilt angle of each individual mirror electrostatically. Each mirror has the two states, either +x degrees or −x degrees where x is usually 12 degrees or 17 degrees. This mirror array in a DMD is covered by a transparent window for protection as well as to control the incident light properties. The rate at which the orientation of the individual mirrors can be changed varies from about 4 kHz for the most basic variants to 32 kHz for the advanced variants. The first DMD was made by Texas Instruments, See e.g., U.S. Pat. No. 5,504,575, incorporated herein by reference. DMDs are a relatively mature technology, with Texas Instruments introducing DMD incorporating commercial products in 1996. DMDs are used in digital cameras, HD televisions, digital projectors. FIG. 68 shows the mirror array of the DMD.

While the currently available DMDs are specified to work in the visible light to infrared light region only, research is being done on how to adapt these devices for UV applications. This research is especially driven by the use of the DMDs in maskless lithography devices. DMDs with reliable operating characteristics down to 390 nm have already been demonstrated and Texas Instruments is working to develop DMD's capable of working down to the 200 nm ranges. Thompson, J., et al., *Digital Projection of UV Light for Direct Imaging Applications, DLP Technology is Enabling the Next Generation of Maskless Lithography,* 2008. Research in this area has also demonstrated viable operation of DMDs with specialized windows of sapphire or quartz down to 265 nm wavelength light. Fong, J. T., et al., *Advances in DMD-Based UV Application Reliability Below 230 nm,* Proc. SPIE, Vol. 7637 (2010). So it is reasonable to expect development of viable DMD's capable of operating in the deep UV region.

As noted herein, the detector can use a diffraction grating to shine the spectrum of light from a UV LED array on to a DMD, then select the required bandwidth of light by switching on the required micromirror rows and using the rest of the micromirror array in the off-position to direct the remaining light elsewhere. Because of the extremely small size of the micromirrors compared to a motor mounted diffraction grating, the detector can switch wavelengths at extremely high speeds. This capability is not present in current detectors.

Functional Schematic

Figure 69:
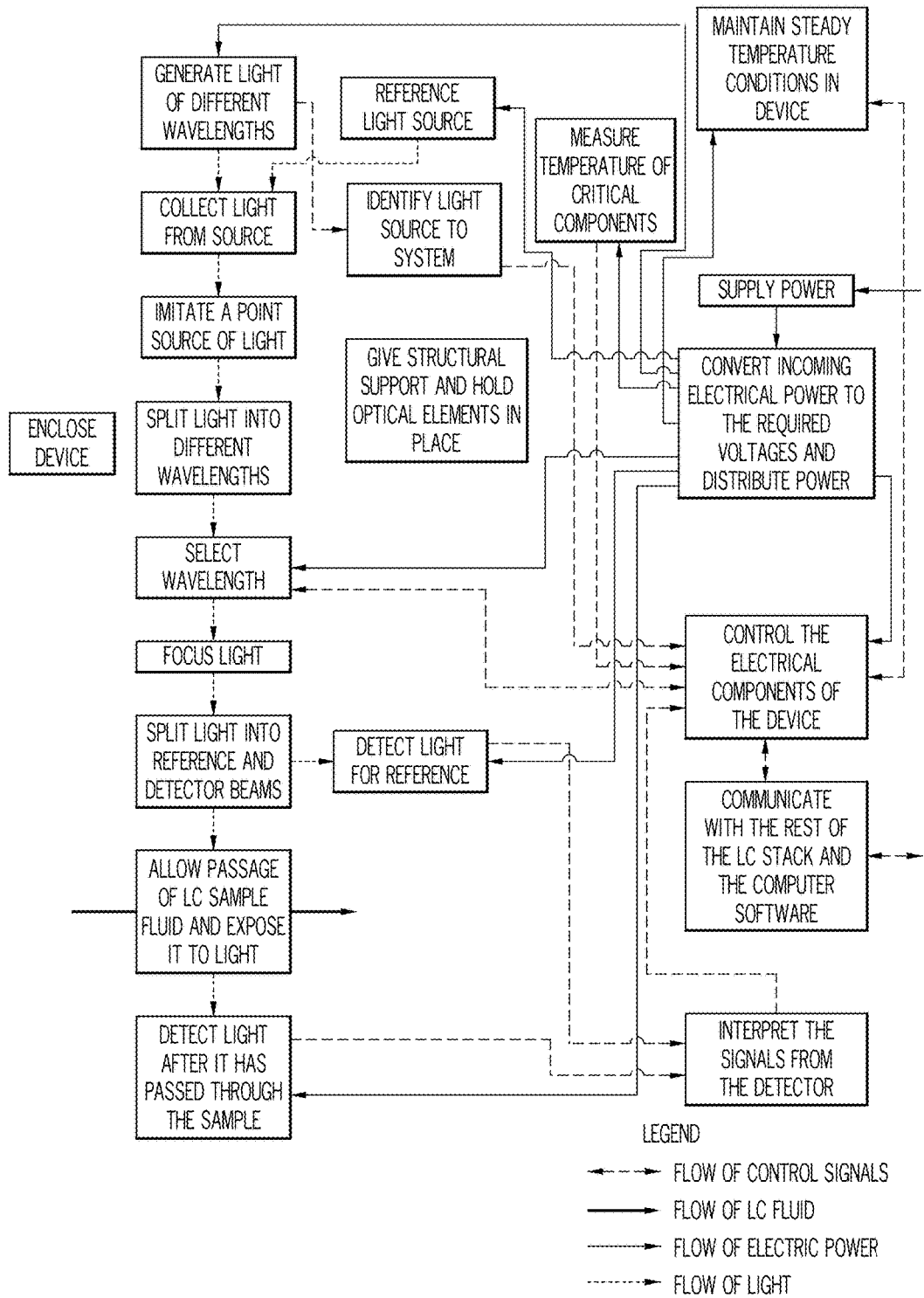
FIG. 69 provides a functional schematic of an embodiment of the detector described herein.

As shown in FIG. 69, after the decomposition process, the 21 identified functional elements are arranged in a functional schematic to show how the detector should work. FIG. 69 depicts the different type of interactions that can occur in the detector. There is a light source 50 to generate light of different wavelengths along with a reference wavelength light source 50. Light from these two sources is collected and sent through the system by imitating a point source. This is necessary for achieving good optical resolution as discussed herein. Light is then split into its constituent wavelengths and the required wavelengths are selected and focused. This focused light is split into a sample beam and a reference beam which is recorded for comparison to the sample beam after it has gone through the liquid chromatography sample.

To run the detector 4, power has to be supplied to it. The incoming power has to be converted to the required voltages for the different components to be distributed to them, and then the various components, especially the electrical ones have to be controlled. The light measurements have to be interpreted and this data has to be communicated to the control software as well as input from the rest of the liquid chromatography system.

EXAMPLE XII

Proposed Architecture Scheme for Configuration 1

Figure 70:
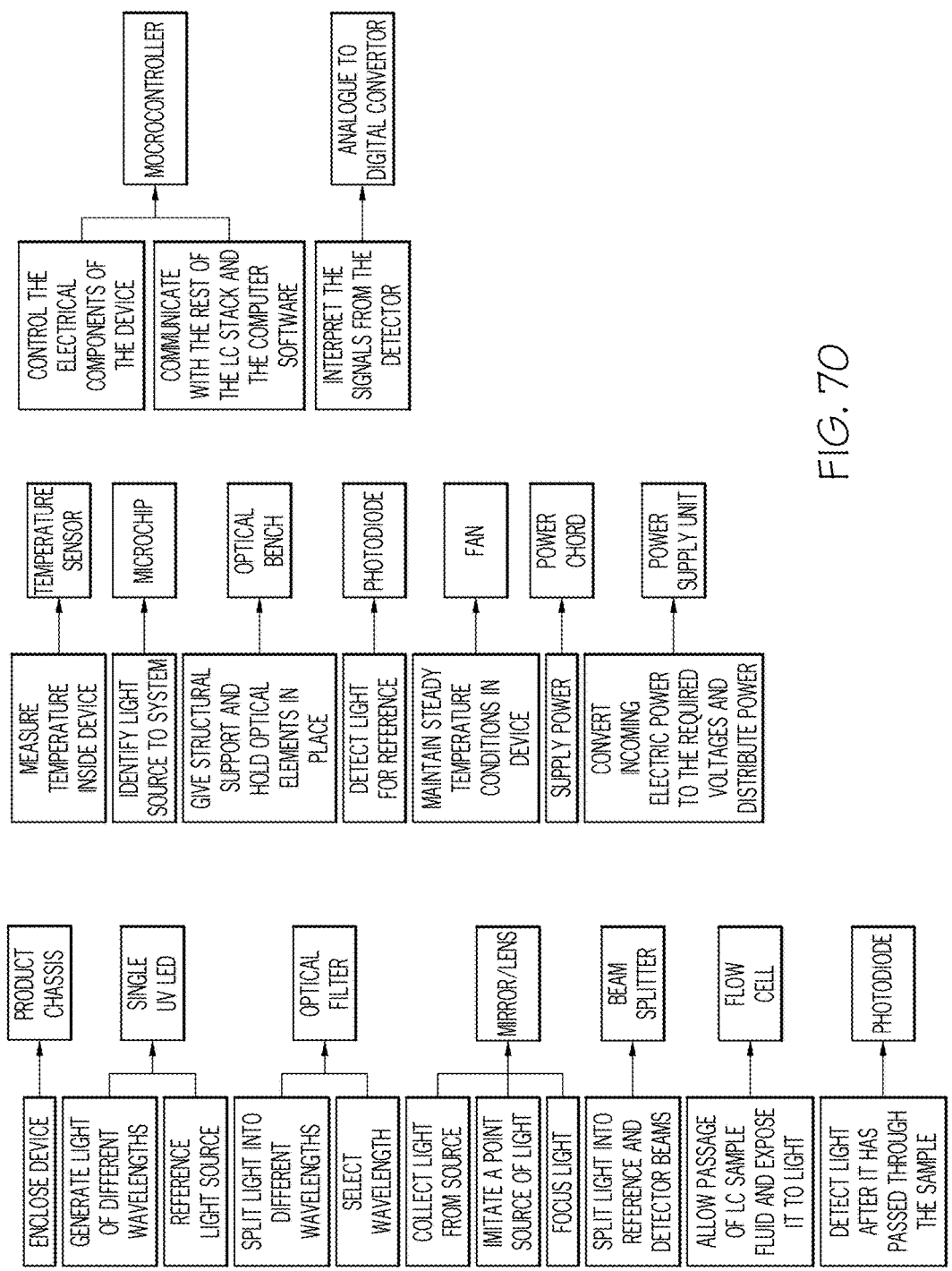
FIG. 70 shows functionality of the components of an embodiment of a fixed wavelength detector as provided in Configuration 1.
Figure 71:
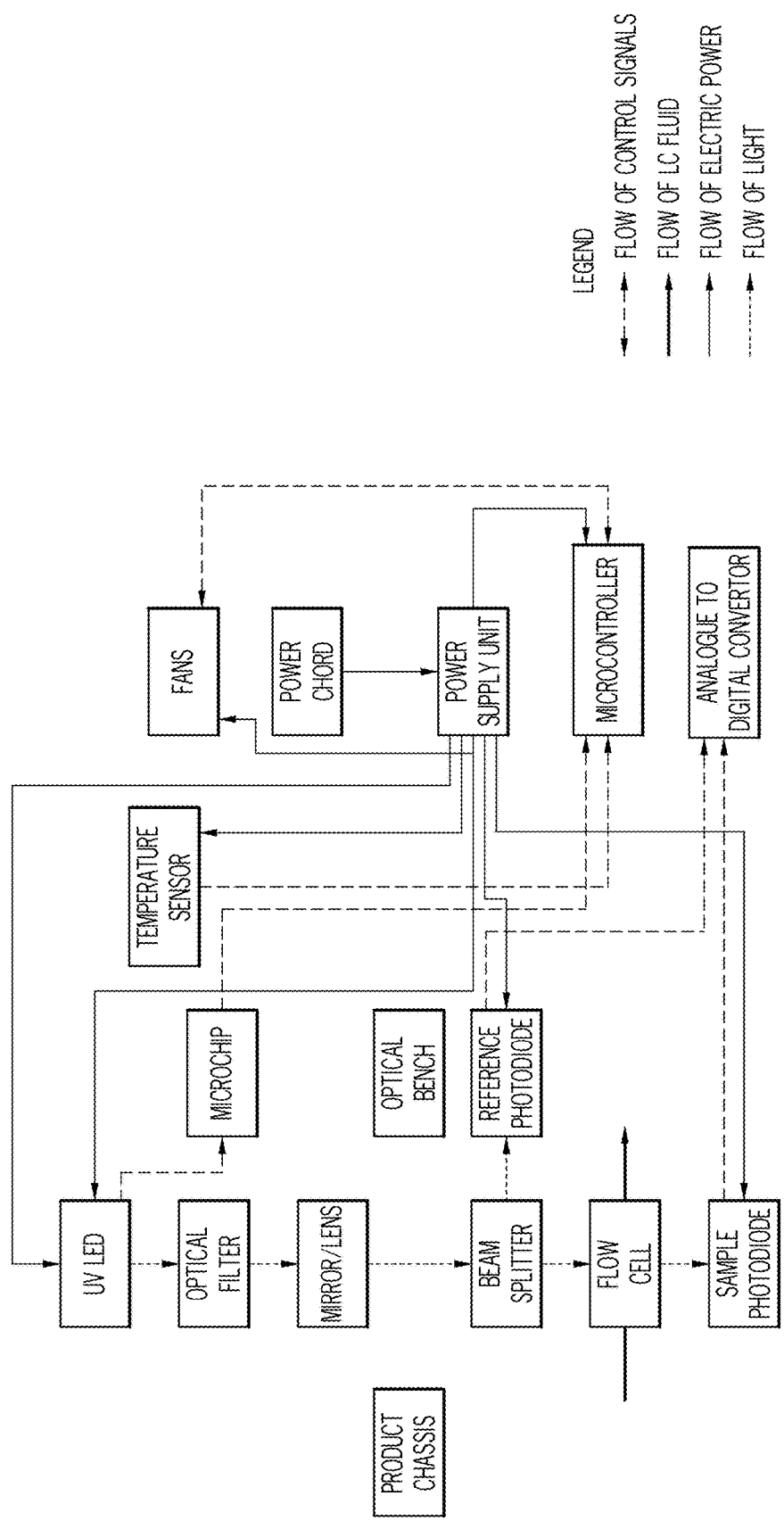
FIG. 71 depicts a schematic of an embodiment of the detector as provided by Configuration 1.

As described herein, configuration 1 is an embodiment of a single wavelength type detector which has the capability to switch wavelengths if required. This is suitable for the QC/QA and analytical customer who uses a single wavelength most of the time, yet would prefer the capability to change the wave length when needed. The functional components of the detector 4 are shown in FIG. 70. A schematic of an embodiment of the physical components of the detector 4 is provided in FIG. 71. Having a single LED 6, this architecture represents an efficient method of manipulating the light. In this embodiment of the detector 4, only a single UV LED is considered, which can have a half height wavelength range of about 12 nm. The range can be further narrowed to the required wavelength by the using narrow pass optical filters which can narrow the half height bandwidth up to 2 nms. The LED 6 can have a microchip to identify it to the system. Also, because this configuration works with a single wavelength, there is no need for a reference light source 50 as it would be redundant and linked with the LED itself. Then a mirror or a lens can be used to focus the light on a beam splitter, which would split the light into a reference beam for the reference photodiode and a sample beam which would go through the flow cell and be recorded by the sample photodiode. The optical bench assembly 40 can support and hold the optical components in place. Temperature sensors would measure the internal temperature of the detector 4 and appropriately placed fan(s) would regulate the temperature inside. Power would be supplied to the detector through a power cord and would be converted to the required voltages using a power supply unit, which could be an off-the-shelf component or a customized build. For the electronic control, circuitry incorporating a microcontroller with the requisite analogue to digital converters for the photodiodes will be used. The circuitry would also communicate with the rest of the liquid chromatography system and the control software. Finally, a product chassis would enclose the detector 4 to protect it from outside conditions. A key innovation is making the LEDs modular so as to allow the customer to change the wavelength if and when required.

EXAMPLE XIII

Proposed Architecture Scheme for Configuration 2 and 3

Figure 72:
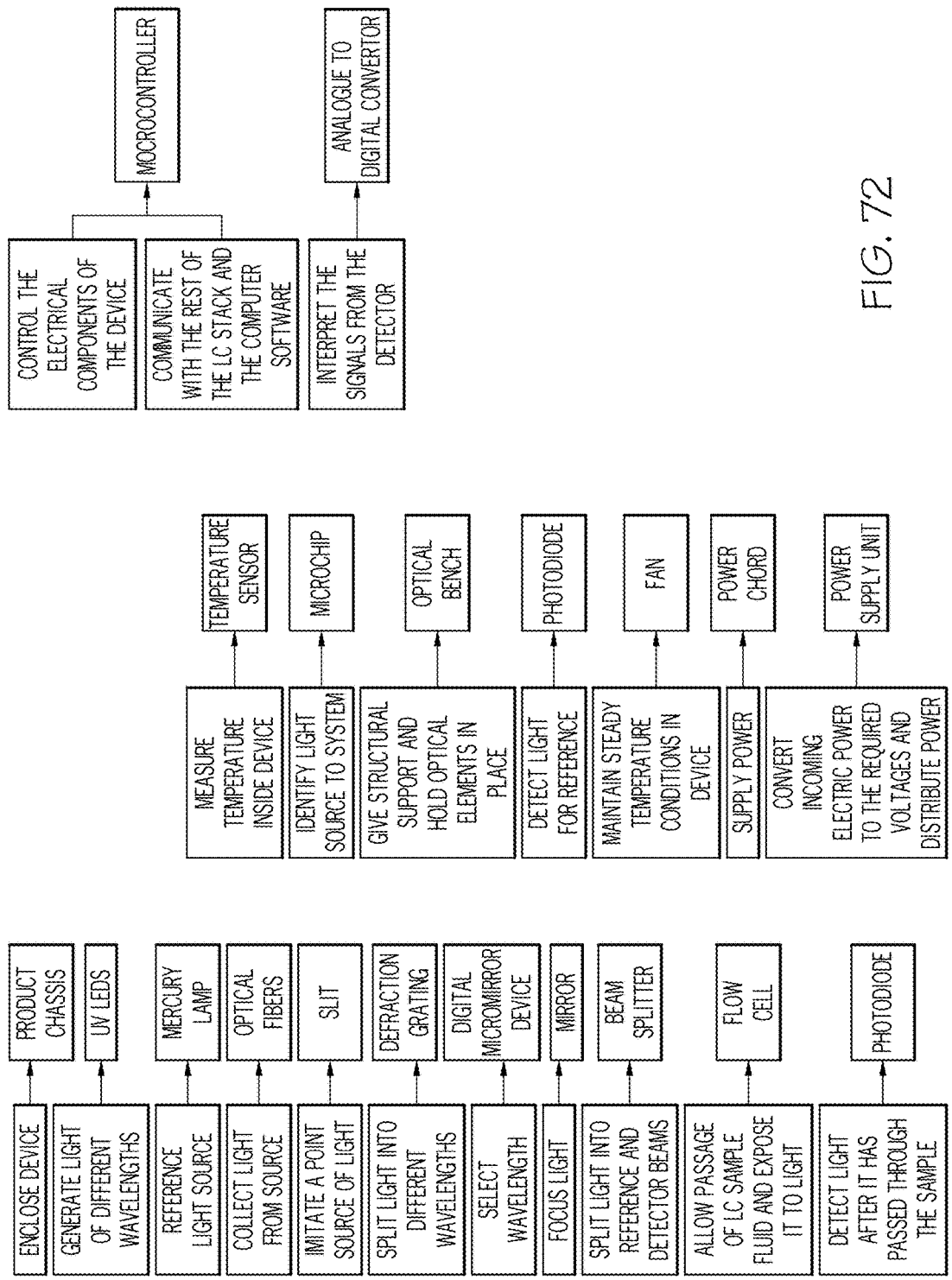
FIG. 72 shows functionality of the components of an embodiment of a fixed wavelength detector as provided in Configurations 2 and 3.
Figure 73:
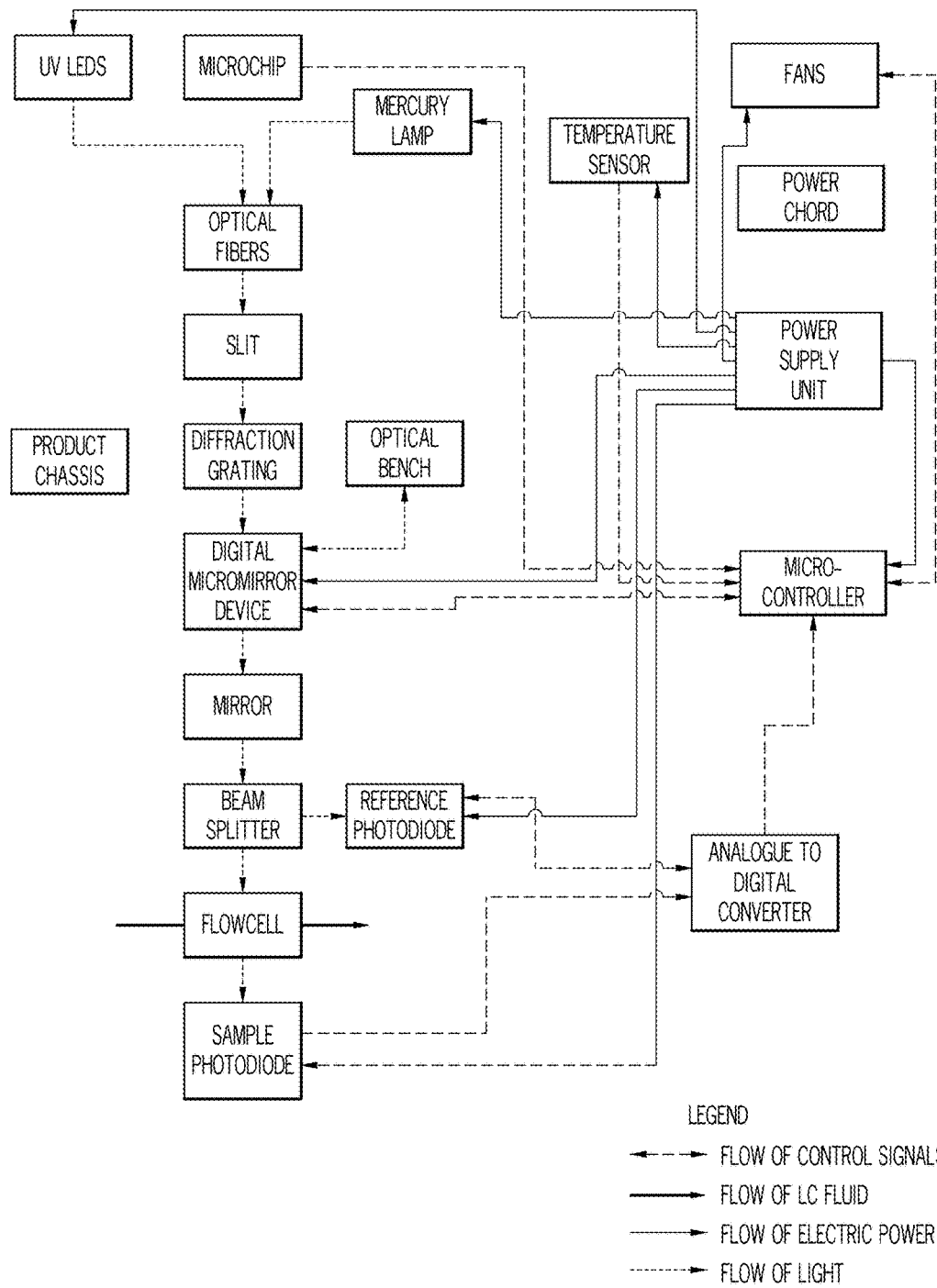
FIG. 73 is a schematic of an embodiment of the detectors provided by Configurations 2 and 3.

For Configurations 2 and 3, the linking of functional elements to physical components is shown in FIG. 72 and a schematic derived from this set of choices is shown in FIG. 73. Both configurations 1 and 2 allow scanning through a range of wavelengths with simultaneously measuring the response of the liquid chromatography sample to various wavelengths. As discussed herein, current methods employ either a turnable prism/grating or split the light on to a photodiode array after it has passed through the sample. Use of the digital micro-mirror device ("DMD") in combination with a diffraction grating to switch wavelengths at high speeds is proposed. As the range of wavelengths required for detectors would be more than what is provided by a single UV LED, an array of such LEDs would be needed. In this array, the LEDs would be modular and each would have a microchip to identify itself to the system.

For Configuration 2, the digital micro-mirror array would cover the UV light range while for Configuration 3, the digital micro-mirror array would cover the UV and visible light range both. To collect and combine the light from these LEDs, optical fibers would be used. These optical fibers would end on a slit, which would act as a point source and determine the lower limit on the resolution of the system. The light beam would then be split into its constituent wavelengths and made incident across the DMD 8. By controlling the digital micro-mirror array, it would be possible to select specific wavelengths as well as the bandwidth of wavelengths at high speed. The selected light would then be incident on a beam splitter and split into the reference beam and the sample beam. The reference beam would be recorded by the reference photodiode and the sample beam would pass through the flow cell 66 carrying the liquid chromatography sample. The rest of the functional elements are linked to similar physical elements as in Configuration 1. This schematic was mapped out on a design structure matrices ("DSM") for studying the key interactions to define product architecture at system level.

Clustering Through DSM for System Level Architecture

Key interactions in the detector for Configurations 2 and 3 are the light interaction and the spatial interactions. Configuration 1 was not considered for DSM analysis as it is a relatively simple design. As electric power and information can be easily transmitted through flexible wires, these interactions were not considered for system level grouping. It should be noted, that these clustering are not final but are a method to look at the effect of the proposed clustering on interactions between various sub-systems.

Suggested Clustering on the Basis of Light Interactions

The clustered DSM for light interactions in the detector 4 is shown in FIG. 74. The clustering has been done manually minding the various considerations discussed so far and since the UV LEDs have to be kept modular for technological considerations, they are not included in any cluster. Cluster 1 consists of the optical fibers and the reference light source, a small mercury lamp generating light at 254 nm. It will link with the UV LEDs. Cluster 2 consists of all the remaining optical elements and the optical bench holding the optical elements together. Such a grouping allows for internalization of a number of interactions and the design teams for each cluster will have to take special consideration of only 2 optical interactions—the LED to optical fiber interactions and the optical fibers to the slit in the optical bench.

Suggested Clustering on the Basis of Spatial Interactions

Figure 75:
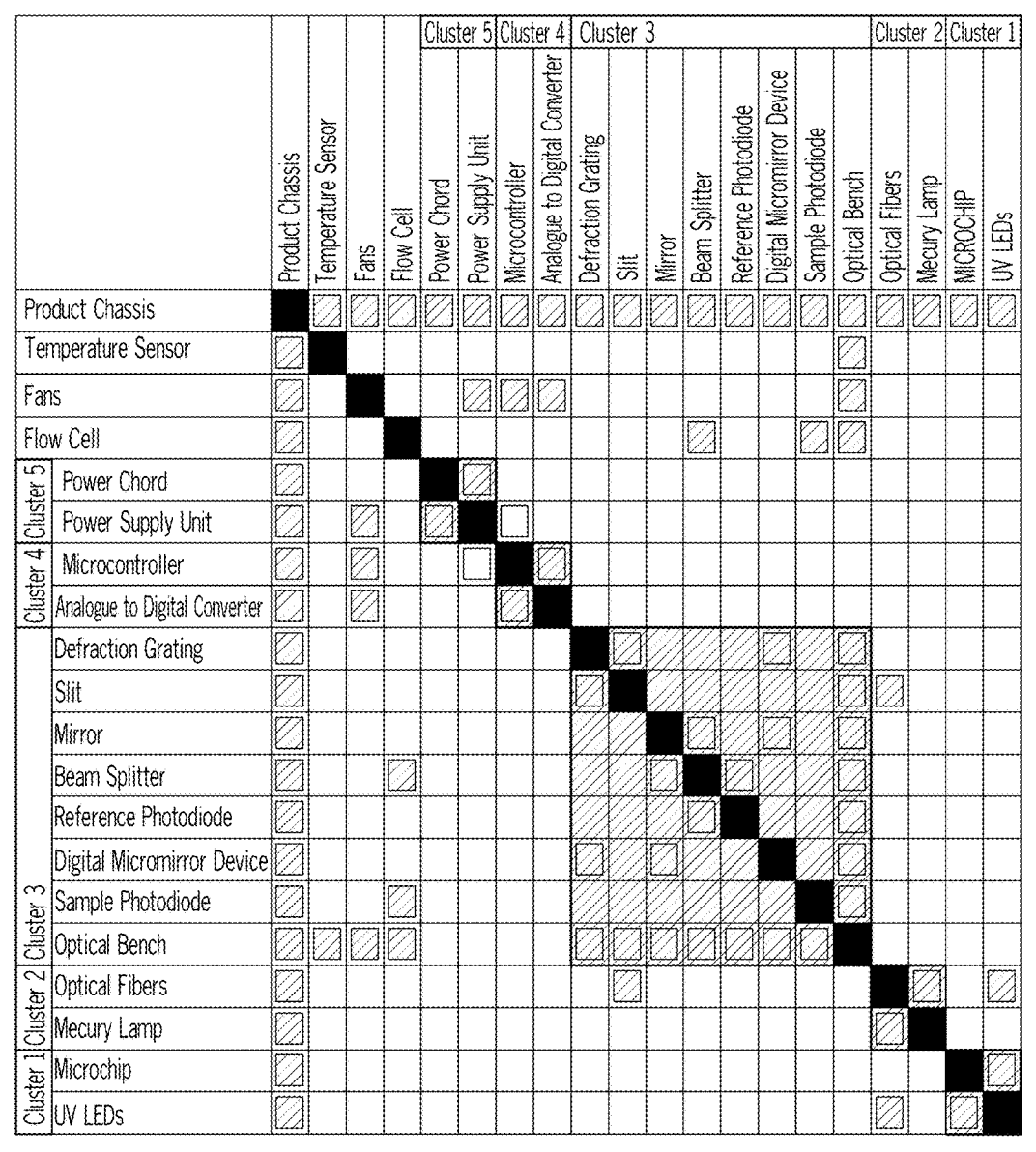

The spatial interaction for various components in the detector was mapped out on a DSM and the clustering was done as shown in FIG. 75. These interactions refer to the adjacency between the various components. The clustered DSM for spatial interactions shows that even with the suggested clustering, there are still numerous out-of-chunk interactions.

Taking into account the market, technology and the key interactions, the final architecture for each of the three configurations was developed.

Product Architecture for Configuration 1

Figure 76:
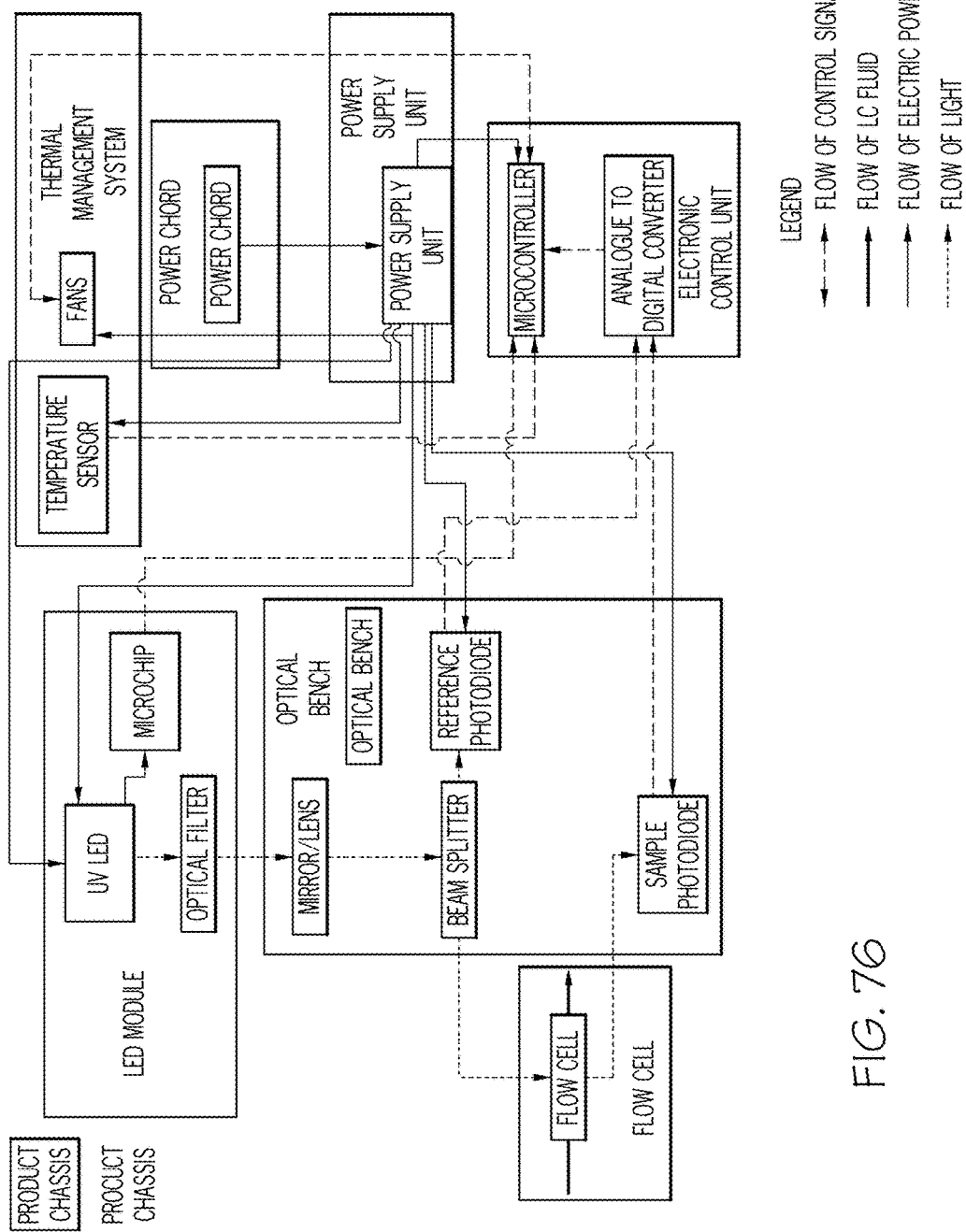
FIG. 76 shows an embodiment of an architecture scheme for Configuration 1.

The product architecture for Configuration 1 with the selected components and subsystems is shown in FIG. 76. This grouping was done keeping in mind the technological considerations and discussions with the optical and mechanical designers for such detectors as discussed herein.

Led Module

For Configuration 1, the LED module comprises the LED, a narrow pass optical filter to select a single wavelength and a microchip to identify the wavelength of the LED module to the system. This enables the customers to buy the LED module of the wavelength they are interested in.

Optics Bench Assembly 40

The optics bench assembly 40 comprises the optics bench casing to hold the remaining optical elements—the mirror/lens, the beam splitter, the reference photodiode & the sample photodiode. The optical casing will also have interfaces for the LED module and the flowcell module. The casing should be designed in such a manner to allow for easy replacement of the optical elements in case of wear.

Flow Cell

Each liquid chromatography system manufacturer has its own variety of flow cells, varying in optical path length and the volume of the sample exposed to the light. The flow cell can accommodate various flow cells as well as provide a standard interface for them to the optical bench.

Thermal Management System

The thermal management system will consist of temperature sensors and fan(s) to maintain a steady temperature inside the detector. It will have to be setup to be able to take into account heat from all sources.

Power Cord

The power cord has been kept as a separate module as its design will vary from country to country.

Power Supply Unit

The power supply unit can be a standard off-the-shelf component or a custom built unit which will convert the wall electrical power input to the various voltages required by the other components.

Electronic Control System

The electronic control system will comprise of the circuitry including the microcontroller, the analogue to digital converters and the various ancillary electronics to control the detector, and to communicate with the control software and the rest of the liquid chromatography system.

Product Chassis

The product chassis will enclose the entire detector and protect it from outside elements and should have an appropriate receptacle for the LED module in conjunction with optics bench.

Product Architecture for Configurations 2 and 3

Figure 77:
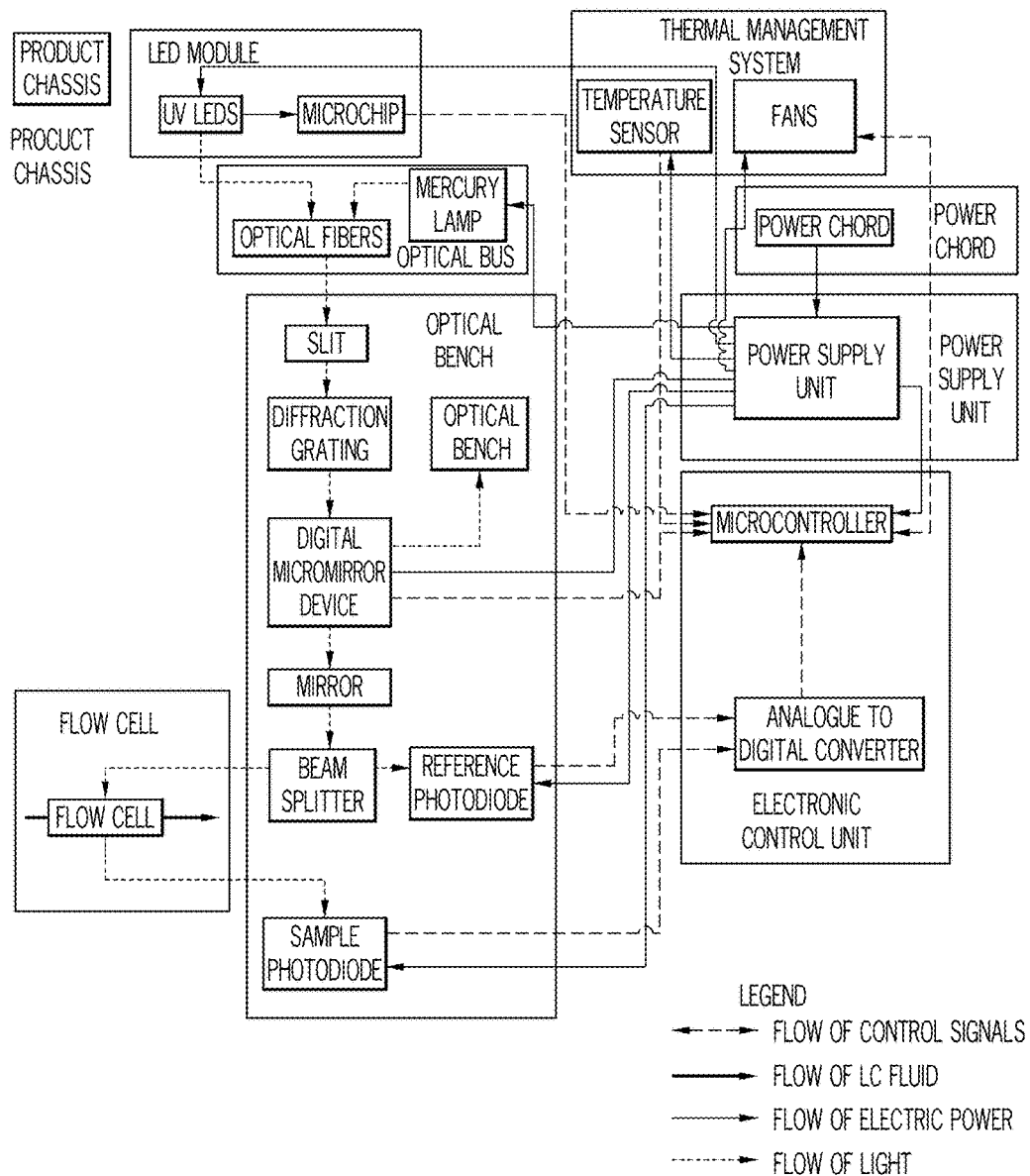
FIG. 77 shows embodiments of architecture schemes for Configurations 2 and 3.

For Configurations 2 and 3 of the detector 4, the developed product architecture is shown in FIG. 77.

Led Module

The LED module for Configuration 2 and 3 comprises the LED and the microchip identifying the specific LED to the system. The LED modules can have electrical and information interfaces for taking power and allowing the microchips to be read by the system.

Optical Bus

The optical bus is an LED array holder with receptacles that fit the LED modules. The optical bus can also have a small mercury lamp to act as a reference source for the system. Optical fibers from the receptacles and the mercury lamp can take the light to the entrance of the optical bench. It should be noted here that the receptacles in the optical bus have to be designed such that they can supply power to the LED modules as well as read the microchips in them to identify which wavelengths are they emitting. The optical bus can be the common bus chunk and the LED modules will have a bus-modular architecture with the optical bus. Configuration 2 can have about 11 LED receptacles to cover the UV range while Configuration 3 can have a greater number of receptacles to extend this range to the visible spectrum.

Optical Bench

The optical bench for Configurations 2 and 3 can be larger to accommodate more optical elements. The casing of the optical bench can hold the slit of the required width to determine the resolution of the system, the optical fibers from the optical bus will interface with this slit. It can also hold the remaining optical elements in place as required by the optical design, these being the diffraction grating, the DMD, the focusing mirror, the beam splitter, the reference and sample photodiode. It should be noted that in these two configurations, the optics bench assembly 40 also has to absorb the light that the DMD shunts away for the unselected wavelengths. Furthermore the optics bench assembly 40 will have the appropriate interface for the flow cell module. The casing is designed with the issues of assembly as well as serviceability in mind. It would be beneficial if a slot-modular architecture was followed in its design, with each optical element fitting into its own specific slot and being easily accessible for replacement.

Flow Cell

Each liquid chromatography system manufacturer has its own variety of flow cells, varying in optical path length and the volume of the sample exposed to the light. The flow cell chunk should be able to accommodate these various flow cells as well as provide a standard interface for them to the optical bench.

Thermal Management System

The thermal management system will consist of temperature sensors and fan(s) to maintain a steady temperature inside the detector 4. It will have to be setup in such a manner to account for all heat sources. This system will be more critical for Configurations 2 and 3 as the DMD will also generate heat in these.

Power Cord

The power cord will be a separate module as its design will vary from country to country.

Power Supply Unit

The power supply unit can be a standard off-the-shelf component or a custom built unit which will convert the wall electrical power input to the various voltages required by the other components.

Electronic Control System

The electronic control system will comprise of the circuitry including the microcontroller, the analogue to digital converters and the various ancillary electronics to control the detector 4, and to communicate with the control software and the rest of the liquid chromatography system.

Product Chassis

The product chassis will enclose the entire detector 4 and protect it from outside elements and will expose the optical bus to the customer for switching out the LED modules.

Implications of the Detector Architecture

Product Changes

There are two key elements that are likely to require upgrades in the detector 4 as their technology matures: the UV LEDs and the DMD. By making the LED chunk completely modular as shown in the architecture, it is possible for the company manufacturing such a detector to offer customer upgrades as soon as they are available. The DMD on the other hand is part of the optics bench assembly 40 and while the optical bench assembly should be designed keeping in mind serviceability issues any change involving the size of the DMD will lead to a redesign of the optical bench. A key feature in the DMD that is still in the developmental phase is the window covering the micromirror array, for their use in the UV region. Henceforth it may be possible to upgrade a same size DMD with an improved window in the detector.

Product Variety

As noted above, there are three key customer segments that have been identified and a suitable product architecture for three product configurations developed. Table 23 shows the differentiation plan for the three configurations and represents how the three products will be different for the customer and the market in terms of the various chunks.

TABLE 23

Differentiation Plan for Three Detector Configurations

| Differentiating Attributes | Single Wavelength | UV Region Scanning | UV-Visible Region Scanning |
|---|---|---|---|
| LED Module | LED with optical filter: optimized for single wavelength | LED with full possible emission spectrum | LED with full possible emmision spectrum |
| Optical Bus | Not applicable | Smaller optical bus to cover the UV range | Larger optical bus to cover the UV-visible range |
| Product Chassis | Smaller Chassis | Large Chassis | Large Chassis |

Component Standardization

Table 24 shows the commonality plan for the three detector 4 configurations. This plan considers all the chunks and shows how different chunks will be common or different across the three configurations. For each configuration, the type of the chunk that will be used in it is shown.

TABLE 24

Commonality Plant for Three Detector Configurations

| Chunk | Number of types | Single Wavelength | UV Region Scanning | UV-Visible Region Scanning |
|---|---|---|---|---|
| LED Module | 2(with multiple subtypes depending on wavelength) | Type I | Type II | Type II |
| Optical Bus | 2 | NA | Type I | Type II |
| Optical Bench | 3 | Type I | Type II | Type III |
| Flowcell | 1(with subtypes depending on the liquid chromatography system) | Type I | Type I | Type I |
| Electronic Control System | 2 | Type I | Type II | Type II |
| Thermal Management System | 1 | Type I | Type I | Type I |
| Power Chord | 1 | Type I | Type I | Type I |
| Power Supply Unit | 2 | Type I | Type II | Type II |
| Product Chassis | 2 | Type I | Type II | Type II |

After the architectural scheme was finalized, Configuration 2 was selected for detailed. Even though Configuration 1 has a simplified design and Configurations 2 and 3 have a complex design incorporating a digital micro-mirror device along with the UV LEDs and share similar chunks. Furthermore, it was estimated that this configuration would appeal to approximately 40% on the market as discussed herein.

Summary

To summarize, architecture for embodiments of the liquid chromatography detector using UV LEDs in instead of traditional deuterium lamps was developed. Three possible product configurations have been identified and two architectural schemes were developed and are described in the examples provided herein.

We claim:

1. A detector for liquid chromatography comprising:
   a light delivery system comprising a light source that emits light having a plurality of wavelengths; and
   a wavelength selection module optically coupled to the light delivery system, the wavelength selection module comprising:

a digital micro-mirror device configurable as a variable slit and having a plurality of micro-mirrors each controllable to direct light along a first optical path to a beam dump or to direct light along a second optical path, wherein dimensions of the variable slit are determined by the micro-mirrors directing light along the second optical path; and a spectrally dispersive optical element to receive light and provide diffracted light having a linear dispersion of the wavelengths.

2. The detector of claim 1 wherein the digital micro-mirror device is configurable as a variable entrance slit and wherein the spectrally dispersive optical element receives the light from the digital micro-mirror device that is directed along the second optical path.

3. The detector of claim 2 further comprising a flow cell disposed along an optical path between defined between the light delivery system and the wavelength selection module.

4. The detector of claim 1 wherein the digital micro-mirror device is configurable as a variable exit slit, wherein the spectrally dispersive optical element receives the light emitted from the light delivery system and wherein the digital micro-mirror device receives the diffracted light from the spectrally dispersive optical element.

5. The detector of claim 4 further comprising a flow cell disposed to receive the diffracted light from the spectrally dispersive optical element.

* * * * *